US012759983B2

(12) United States Patent
Shinohara et al.

(10) Patent No.: US 12,759,983 B2
(45) Date of Patent: Oct. 13, 2026

(54) HYDROGENATED QUINOXALINES

(71) Applicant: OTSUKA PHARMACEUTICAL CO., LTD., Tokyo (JP)

(72) Inventors: Tomoichi Shinohara, Osaka (JP); Tsuyoshi Nishiyama, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 432 days.

(21) Appl. No.: 18/579,051

(22) PCT Filed: Jul. 12, 2022

(86) PCT No.: PCT/JP2022/027396
§ 371 (c)(1),
(2) Date: Jan. 12, 2024

(87) PCT Pub. No.: WO2023/286768
PCT Pub. Date: Jan. 19, 2023

(65) Prior Publication Data
US 2024/0409519 A1 Dec. 12, 2024

(30) Foreign Application Priority Data
Jul. 13, 2021 (JP) ................................ 2021-115550

(51) Int. Cl.
*C07D 241/42* (2006.01)
*A61K 31/498* (2006.01)

(52) U.S. Cl.
CPC .......... *C07D 241/42* (2013.01); *A61K 31/498* (2013.01)

(58) Field of Classification Search
CPC ........................... C07D 241/42; A61K 31/498
See application file for complete search history.

(56) References Cited

FOREIGN PATENT DOCUMENTS

| | | | | |
|---|---|---|---|---|
| JP | 2010-505855 | A | 2/2010 | |
| JP | 2010-536713 | A | 12/2010 | |
| JP | 2012-012388 | A | 1/2012 | |
| JP | 2015-535275 | A | 12/2015 | |
| TW | I448289 | B | 8/1997 | |
| WO | 2008/063287 | A2 | 5/2008 | |
| WO | 2009/027820 | A2 | 3/2009 | |
| WO | 2010/064735 | A1 | 6/2010 | |
| WO | 2012/036253 | A1 | 3/2012 | |
| WO | WO-2013137479 | A1 * | 9/2013 | ................ A61P 9/00 |
| WO | 2014/072881 | A1 | 5/2014 | |

OTHER PUBLICATIONS

CRN2892708-27-7 (Year: 2023).*
International Search Report issued Oct. 4, 2022 in Application No. PCT/JP2022/027396.
International Preliminary Report on Patentability with Written Opinion issued Jan. 16, 2024 in Application No. PCT/JP2022/027396.
Jonathan Posner, et al., "Attention-deficit hyperactivity disorder," Lancet, Jan. 23, 2020, vol. 395, pp. 450-462 (13 pages total).
Stephen V. Faraone, et al., "The age-dependent decline of attention deficit hyperactivity disorder: a meta-analysis of follow-up studies," Psychological Medicine, 2006, vol. 36, 159-165 (7 pages total).
Shuntaro Itagaki, et al., "Neurobiology and Pharmacotherapy of Adult Attention Deficit Hyperactivity Disorder (ADHD): Comparison with Childhood," Clinical Psychopharmacology, vol. 17, No. 9, 2014, pp. 1229-1236 (22 pages total).
Shun Okada, "Clinical Profile of ADHD in Adulthood," Clinical Psychopharmacology, vol. 15, No. 11, 2012, pp. 1811-1820 (29 pages total).
Narong Maneeton, et al., "A systematic review of randomized controlled trials of bupropion versus methylphenidate in the treatment of attention-deficit/hyperactivity disorder," Neuropsychiatric Disease and Treatment, Dovepress, vol. 10, Aug. 1, 2014, pp. 1439-1449 (11 pages total).
Emili Banerjee, et al., "Does serotonin deficit mediate susceptibility to ADHD?," Neurochemistry International 82, 2015, pp. 52-68 (17 pages total).
Sachiko Hiraide, et al., "Behavioural effects of monoamine reuptake inhibitors on symptomatic domains in an animal model of attention-deficit/hyperactivity disorder," Pharmacology, Biochemistry and Behavior 105, 2013, pp. 89-97 (9 pages total).
Communication dated Dec. 18, 2025 in Taiwanese Application No. 111126028.

* cited by examiner

*Primary Examiner* — Jeffrey S Lundgren
*Assistant Examiner* — Ibrahim D Bori
(74) *Attorney, Agent, or Firm* — Sughrue Mion, PLLC

(57) ABSTRACT

Provided is a therapeutic agent for ADHD having an efficacy comparable to that of central nervous system stimulants and the same low risk of drug dependence and abuse as existing non-central nervous system stimulants, more particularly a compound represented by formula [I]:

[I]

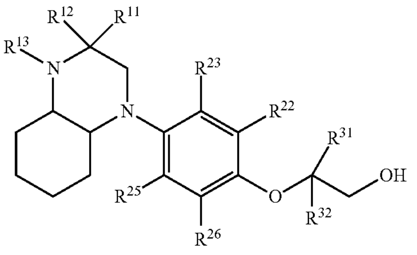

wherein each symbol is as defined in the description, or a salt thereof.

35 Claims, No Drawings

HYDROGENATED QUINOXALINES

CROSS REFERENCE TO RELATED APPLICATIONS

This application is a National Stage of International Application No. PCT/JP2022/027396 filed Jul. 12, 2022, claiming priority based on Japanese Patent Application No. 2021-115550 filed Jul. 13, 2021.

TECHNICAL FIELD

The present invention relates to a heterocyclic compound, more particularly a heterocyclic compound having serotonin, norepinephrine and/or dopamine reuptake inhibitory activity.

BACKGROUND TECHNOLOGY

Attention-deficit hyperactivity disorder (ADHD) is a developmental disorder with inattention, hyperactivity and impulsivity as its core symptoms. The prevalence is estimated to be 5% in children and 2.5% in adults (NPL 1), and it has been reported that more than 65% of patients diagnosed with ADHD in childhood continue to have ADHD symptoms in adult life (NPL 2).

It has been reported that ADHD may cause various secondary and comorbid disorders, in addition to its core symptoms, as the patients grow (NPL 3). In general, ADHD patients have higher prevalence of mood disorders, anxiety disorders, exter-nalizing disorders, or substance use disorders, and many difficulties in daily life in terms of independence, education, employment status, economic status, and the like (NPL 4).

In order to overcome such disorders, it is considered necessary to establish the diagnosis and to engage in treatment at an early stage.

Monoaminergic nervous systems, such as dopamine nervous system, are considered to be involved in the pathogenesis of ADHD, and drug therapy for ADHD mainly uses drugs acting on monoamine nervous systems, such as central nervous system stimulants (amphetamine, methamphetamine, methylphenidate, and their derivatives, etc.) and non-central nervous system stimulants (atomoxetine, guanfacine, clonidine, etc.).

Central nervous system stimulants show excellent efficacy (prompt efficiency, effect), but have the risk of drug dependence and abuse, and its duration of effectiveness is short. Non-central nervous system stimulants have low risk of drug dependence and abuse, but require time for their efficacy to stabilize.

For non-central nervous system stimulants, atomoxetine (norepinephrine reuptake inhibitor) is used as a first-line drug or as a second-line drug when central nervous system stimulants are ineffective or their side effects are intolerable. The antidepressant bupropion (norepinephrine-dopamine reuptake inhibitor) may also be used (NPL 5). In addition, serotonin nervous system has been reported to be involved in impulsivity, which is one of the core symptoms of ADHD (NPL 6), and it has been reported that an impulsivity-like symptom in an animal model of ADHD is suppressed by a serotonin reuptake inhibitor (NPL 7).

PTL 1 and PTL 2 disclose heterocyclic compounds as therapeutic drugs for diseases associated with central nervous system.

CITATION LIST

Patent Literature

[PTL 1] WO2012/036253
[PTL 2] WO2013/137479

Non Patent Literature

[NPL 1] Lancet, 395, 450-462, 2020
[NPL 2] Psycho Med., 36(2), 159-65, 2006
[NPL 3] Japanese journal of clinical psychopharmacology, 17(09), 1229-1236, 2014
[NPL 4] Japanese journal of clinical psychopharmacology, 15(11), 1811-1820, 2012
[NPL 5] Neuropsychiatr Dis Treat. 2014 Aug. 1; 10:1439-49
[NPL 6] Neurochemistry International 82 (2015) 52-68
[NPL 7] Pharmacol Biochem Behav., 105, 89-97, 2013

SUMMARY OF INVENTION

Technical Problem

An object of the present invention is to provide a therapeutic agent for ADHD having an efficacy comparable to that of central nervous system stimulants and the same low risk of drug dependence and abuse as existing non-central nervous system stimulants.

Another object of the present invention is to provide a drug with excellent pharma-cokinetic properties (high metabolic stability, long effective blood concentration retention time, low protein binding rate, low CYP inhibition rate) and sustained pharmacological actions, resulting in a long-lasting effect in less drug interaction, less dose and lower drug blood concentration.

Solution to Problem

As a result of conducting extensive studies to solve the above-mentioned problems, the inventors of the present invention have succeeded in synthesizing a heterocyclic compound having a structure represented by the following general formula, in which a hydroxyethoxy group is attached to the aryl moiety, which can be used for the production of the desired drug.

The present invention was completed based on these findings.

Namely, the present invention includes the following embodiments.

[1-1] A compound represented by formula [I]:

[I]

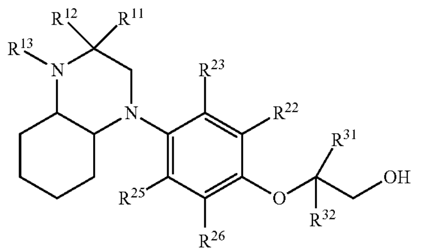

wherein $R^{11}$, $R^{12}$ and $R^{13}$ are the same or different and each independently represents hydrogen or $C_{1-6}$ alkyl, or $R^{11}$ and $R^{12}$ together with the adjacent carbon atom form a 3- to 8-membered cycloalkane;

$R^{22}$, $R^{23}$, $R^{25}$ and $R^{26}$ are the same or different and each independently represents hydrogen, halogen, $C_{1-6}$ alkyl or $C_{1-6}$ alkoxy, or $R^{22}$ and $R^{23}$ form a 9- to 10-membered bicyclic ring system containing oxygen atom as ring-constituting atom together with a benzene ring adjacent to them;

$R^{31}$ and $R^{32}$ are the same or different and each independently represents hydrogen or halogen, or a salt thereof.

[1-2] The compound according to [1-1], wherein the formula [I] is selected from the following formula [Ia], formula [Ib], formula [Ic] or formula [Id]:

[Ia]

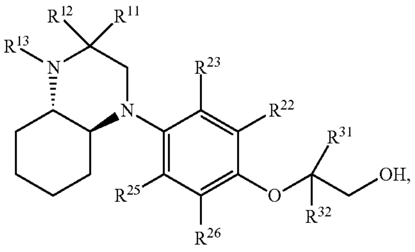

[Ib]

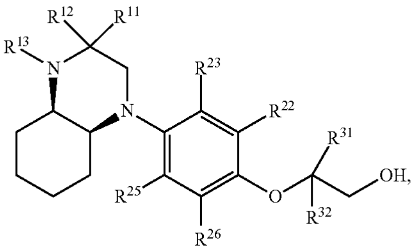

[Ic]

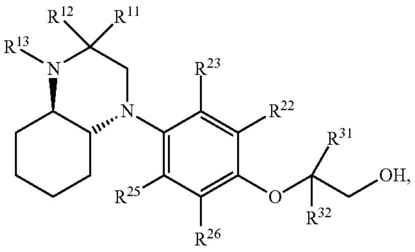

[Id]

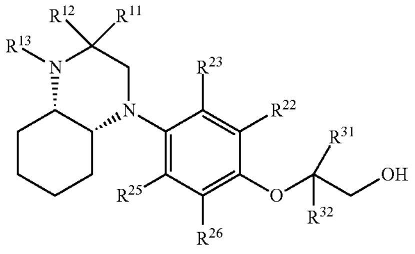

wherein each symbol is as defined above, or a salt thereof.

[1-3] The compound according to [1-1] or [1-2], wherein in the formula [I], $R^{11}$, $R^{12}$ and $R^{13}$ are the same or different and each independently represents hydrogen or methyl, or $R^{11}$ and $R^{12}$ together with the adjacent carbon atom form cyclobutyl;

$R^{22}$, $R^{23}$, $R^{25}$ and $R^{26}$ are the same or different and each independently represents hydrogen, fluorine, chlorine, methyl or methoxy, or $R^{22}$ and $R^{23}$ together with the adjacent benzene ring form a benzofuran;

$R^{31}$ and $R^{32}$ are the same or different and each independently represents hydrogen or fluorine;

or a salt thereof.

[1-4] The compound according to any one of [1-1] to [1-3], wherein in the formula [I], two or more of $R^{22}$, $R^{23}$, $R^{25}$ and $R^{26}$ are hydrogen, or a salt thereof.

[1-5] The compound according to any one of [1-1] to [1-4], which is selected from the group consisting of the following compounds:

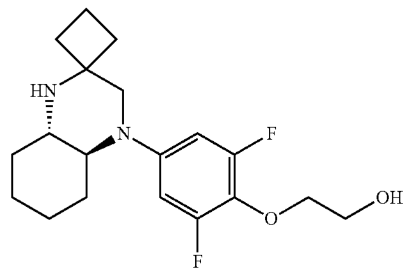

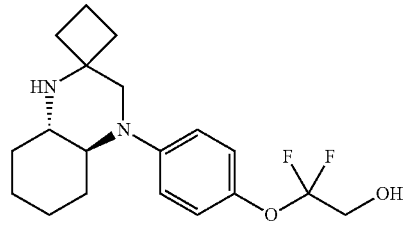

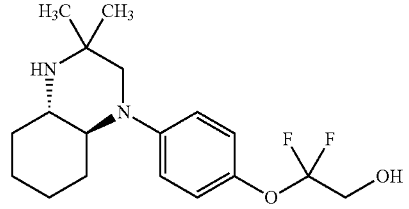

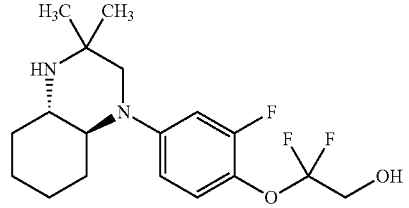

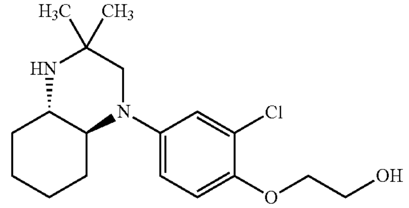

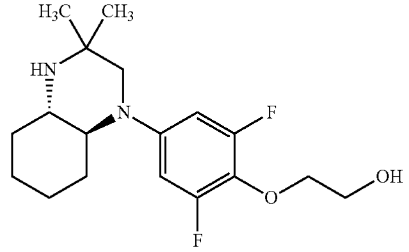

-continued

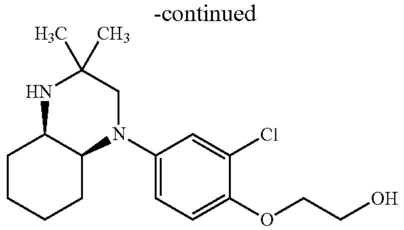

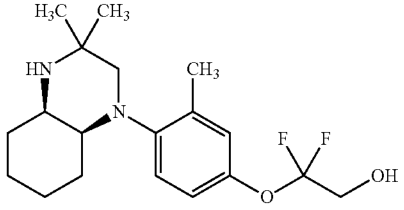

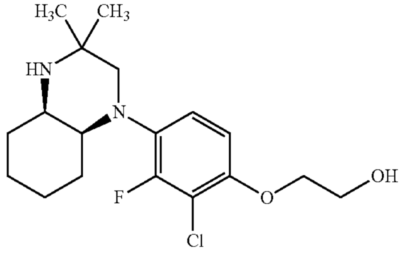

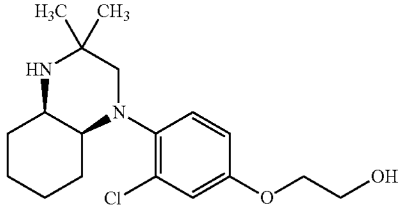

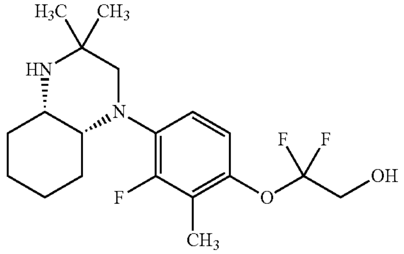

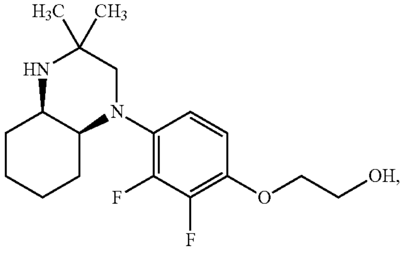

or a salt thereof.

[2] A pharmaceutical composition comprising the compound according to any one of [1-1] to [1-5] or a salt thereof as active ingredient, and a pharmaceutically acceptable carrier.

[3-1] A therapeutic, preventative and/or diagnostic agent for a disorder associated with serotonin, norepinephrine and/or dopamine nerve dysfunction, comprising the compound according to any one of [1-1] to [1-5] or a salt thereof as active ingredient.

[3-2] The therapeutic, preventative and/or diagnostic agent according to [3-1], wherein the disorder is selected from the group consisting of attention-deficit hyperactivity disorder (ADHD), Tourette's disorder, autism spectrum disorder, Asperger's syndrome, depression; depressive symptoms in adjustment disorder; anxiety in adjustment disorder, anxiety associated with various disorders, generalized anxiety disorder, phobias, obsessive-compulsive disorder, panic disorder, post-traumatic stress disorder, acute stress disorder, hypochondriac, dissociative amnesia, avoidant personality disorder, body dysmorphic disorder, eating disorder, obesity, chemical dependence, pain, fibromyalgia, apathy, Alzheimer's disease, memory impairment, Parkinson's disease, restless leg syndrome, endocrine disorder, hypertension, vasospasm, cerebellar ataxia, gastrointestinal tract disorder, negative symptoms in schizophrenia, affective disorders in schizophrenia, cognitive dysfunction in schizophrenia, premenstrual syndrome, stress urinary incontinence, urge urinary incontinence, impulse control disorders, trichotillomania, kleptomania, gambling addiction, cluster headache, migraine, chronic paroxysmal hemicrania, chronic fatigue, premature ejaculation, male impotence, narcolepsy, primary hypersomnia, atonic seizure, sleep apnea syndrome and headache.

[3-3] The therapeutic, preventative and/or diagnostic agent according to [3-2], wherein the depression is selected from the group consisting of major depressive disorder; bipolar I disorder; bipolar II disorder; mixed bipolar disorder; dysthymic disorder; rapid cycler; atypical depression; seasonal affective disorder; postpartum depression; mild depression; recurrent brief depressive disorder; refractory depression-chronic depression; treatment-resistant depression; alcohol-induced mood disorder; mixed anxiety-depressive disorder; depressions associated with various disorders such as Cushing's syndrome, hypothyroidism, hyperparathyroidism, Addison's disease, amenorrhea-galactorrhea syndrome, Parkinson's disease, Alzheimer's disease, cerebrovascular dementia, cerebral infarction, cerebral hemorrhage, subarachnoid hemorrhage, diabetes, viral infection, multiple sclerosis, chronic fatigue syndrome, coronary artery disease, pain, and cancer; middle-age depression; elderly depression; childhood and adolescent depression; and depression induced by a drug such as interferon.

[3-4] The therapeutic, preventative and/or diagnostic agent according to [3-2], wherein the anxiety associated with various disorders is selected from the group consisting of head trauma, brain infection, inner ear disorder, heart failure, arrhythmia, hyperepinephry, hyperthyroidism, asthma and chronic obstructive pulmonary disease.

[3-5] The therapeutic, preventative and/or diagnostic agent according to [3-2], wherein the pain is selected from the group consisting of chronic pain, psychogenic pain, neuropathic pain, phantom pain, postherpetic neuralgia, traumatic neck syndrome, spinal cord injury pain, trigeminal neuralgia and diabetic neuropathy.

[4-1] A therapeutic, preventative and/or diagnostic pharmaceutical composition for a disorder associated with serotonin, norepinephrine and/or dopamine nerve dysfunction, comprising the compound according to any one of [1-1] to [1-5] or a salt thereof as active ingredient.

[4-2] The therapeutic, preventative and/or diagnostic pharmaceutical composition according to [4-1], wherein the disorder is selected from the group consisting of attention-deficit hyperactivity disorder (ADHD), Tourette's disorder, autism spectrum disorder, Asperger's syndrome, depression; depressive symptoms in adjustment disorder; anxiety in adjustment disorder, anxiety associated with various disorders, generalized anxiety disorder, phobias, obsessive-compulsive disorder, panic disorder, post-traumatic stress disorder, acute stress disorder, hypochondriac, dissociative amnesia, avoidant personality disorder, body dysmorphic disorder, eating disorder, obesity, chemical dependence, pain, fibromyalgia, apathy, Alzheimer's disease, memory impairment, Parkinson's disease, restless leg syndrome, endocrine disorder, hypertension, vasospasm, cerebellar ataxia, gastrointestinal tract disorder, negative symptoms in schizophrenia, affective disorders in schizophrenia, cognitive dysfunction in schizophrenia, premenstrual syndrome, stress urinary incontinence, urge urinary incontinence, impulse control disorders, trichotillomania, kleptomania, gambling addiction, cluster headache, migraine, chronic paroxysmal hemicrania, chronic fatigue, premature ejaculation, male impotence, narcolepsy, primary hypersomnia, atonic seizure, sleep apnea syndrome and headache.

[4-3] The therapeutic, preventative and/or diagnostic pharmaceutical composition according to [4-2], wherein the depression is selected from the group consisting of major depressive disorder; bipolar I disorder; bipolar II disorder; mixed bipolar disorder; dysthymic disorder; rapid cycler; atypical depression; seasonal affective disorder; postpartum depression; mild depression; recurrent brief depressive disorder; refractory depression-chronic depression; treatment-resistant depression; alcohol-induced mood disorder; mixed anxiety-depressive disorder; depressions associated with various disorders such as Cushing's syndrome, hypothyroidism, hyperparathyroidism, Addison's disease, amenorrhea-galactorrhea syndrome, Parkinson's disease, Alzheimer's disease, cerebrovascular dementia, cerebral infarction, cerebral hemorrhage, subarachnoid hemorrhage, diabetes, viral infection, multiple sclerosis, chronic fatigue syndrome, coronary artery disease, pain, and cancer; middle-age depression; elderly depression; childhood and adolescent depression; and depression induced by a drug such as interferon.

[4-4] The therapeutic, preventative and/or diagnostic pharmaceutical composition according to [4-2], wherein the anxiety associated with various disorders is selected from the group consisting of head trauma, brain infection, inner ear disorder, heart failure, arrhythmia, hyperepinephry, hyperthyroidism, asthma and chronic obstructive pulmonary disease.

[4-5] The therapeutic, preventative and/or diagnostic pharmaceutical composition according to [4-2], wherein the pain is selected from the group consisting of chronic pain, psychogenic pain, neuropathic pain, phantom pain, postherpetic neuralgia, traumatic neck syndrome, spinal cord injury pain, trigeminal neuralgia and diabetic neuropathy.

[5-1] A method for treating, preventing and/or diagnosing a disorder associated with serotonin, norepinephrine and/or dopamine nerve dysfunction, which comprises administering to a subject an effective amount of the compound according to any one of [1-1] to [1-5] or a salt thereof.

[5-2] The method according to [5-1], wherein the disorder is selected from the group consisting of attention-deficit hyperactivity disorder (ADHD), Tourette's disorder, autism spectrum disorder, Asperger's syndrome, depression; depressive symptoms in adjustment disorder; anxiety in adjustment disorder, anxiety associated with various disorders, generalized anxiety disorder, phobias, obsessive-compulsive disorder, panic disorder, post-traumatic stress disorder, acute stress disorder, hypochondriac, dissociative amnesia, avoidant personality disorder, body dysmorphic disorder, eating disorder, obesity, chemical dependence, pain, fibromyalgia, apathy, Alzheimer's disease, memory impairment, Parkinson's disease, restless leg syndrome, endocrine disorder, hypertension, vasospasm, cerebellar ataxia, gastrointestinal tract disorder, negative symptoms in schizophrenia, affective disorders in schizophrenia, cognitive dysfunction in schizophrenia, premenstrual syndrome, stress urinary incontinence, urge urinary incontinence, impulse control disorders, trichotillomania, kleptomania, gambling addiction, cluster headache, migraine, chronic paroxysmal hemicrania, chronic fatigue, premature ejaculation, male impotence, narcolepsy, primary hypersomnia, atonic seizure, sleep apnea syndrome and headache.

[5-3] The method according to [5-2], wherein the depression is selected from the group consisting of major depressive disorder; bipolar I disorder; bipolar II disorder; mixed bipolar disorder; dysthymic disorder; rapid cycler; atypical depression; seasonal affective disorder; postpartum depression; mild depression; recurrent brief depressive disorder; refractory depression-chronic depression; treatment-resistant depression; alcohol-induced mood disorder; mixed anxiety-depressive disorder; depressions associated with various disorders such as Cushing's syndrome, hypothyroidism, hyperparathyroidism, Addison's disease, amenorrhea-galactorrhea syndrome, Parkinson's disease, Alzheimer's disease, cerebrovascular dementia, cerebral infarction, cerebral hemorrhage, subarachnoid hemorrhage, diabetes, viral infection, multiple sclerosis, chronic fatigue syndrome, coronary artery disease, pain, and cancer; middle-age depression; elderly depression; childhood and adolescent depression; and depression induced by a drug such as interferon.

[5-4] The method according to claim [5-2], wherein the anxiety associated with various disorders is selected from the group consisting of head trauma, brain infection, inner ear disorder, heart failure, arrhythmia, hyperepinephry, hyperthyroidism, asthma and chronic obstructive pulmonary disease.

[5-5] The method according to claim [5-2], wherein the pain is selected from the group consisting of chronic pain, psychogenic pain, neuropathic pain, phantom pain, postherpetic neuralgia, traumatic neck syndrome, spinal cord injury pain, trigeminal neuralgia and diabetic neuropathy.

[6-1] A compound according to any one of [1-1] to [1-5] or a salt thereof, for use in treating, preventing and/or diagnosing a disorder associated with serotonin, norepinephrine and/or dopamine nerve dysfunction.

[6-2] The compound according to [6-1] or a salt thereof, wherein the disorder is selected from the group consisting of attention-deficit hyperactivity disorder (ADHD), Tourette's disorder, autism spectrum disorder, Asperger's syndrome, depression; depressive symptoms in adjustment disorder; anxiety in adjustment disorder, anxiety associated with various disorders, generalized anxiety disorder, phobias, obsessive-compulsive disorder, panic disorder, post-traumatic stress disorder, acute stress disorder, hypochondriac, dissociative amnesia, avoidant personality disorder, body dysmorphic disorder, eating disorder, obesity, chemical dependence, pain, fibromyalgia, apathy. Alzheimer's disease, memory impairment, Parkinson's disease, restless leg syndrome, endocrine disorder, hypertension, vasospasm, cerebellar ataxia, gastrointestinal tract disorder, negative symptoms in schizophrenia, affective disorders in schizophrenia, cognitive dysfunction in schizophrenia, premenstrual syndrome, stress urinary incontinence, urge urinary incontinence, impulse control disorders, trichotillomania, kleptomania, gambling addiction, cluster headache, migraine, chronic paroxysmal hemicrania, chronic fatigue, premature ejaculation, male impotence, narcolepsy, primary hypersomnia, atonic seizure, sleep apnea syndrome and headache.

[6-3] The compound according to [6-2] or a salt thereof, wherein the depression is selected from the group consisting of major depressive disorder; bipolar I disorder; bipolar II disorder; mixed bipolar disorder; dysthymic disorder; rapid cycler; atypical depression; seasonal affective disorder; postpartum depression; mild depression; recurrent brief depressive disorder refractory depression-chronic depression; treatment-resistant depression; alcohol-induced mood disorder; mixed anxiety-depressive disorder; depressions associated with various disorders such as Cushing's syndrome, hypothyroidism, hyperparathyroidism, Addison's disease, amenorrhea-galactorrhea syndrome, Parkinson's disease, Alzheimer's disease, cerebrovascular dementia, cerebral infarction, cerebral hemorrhage, subarachnoid hemorrhage, diabetes, viral infection, multiple sclerosis, chronic fatigue syndrome, coronary artery disease, pain, and cancer; middle-age depression; elderly depression; childhood and adolescent depression; and depression induced by a drug such as interferon.

[6-4] The compound according to [6-2] or a salt thereof, wherein the anxiety associated with various disorders is selected from the group consisting of head trauma, brain infection, inner ear disorder, heart failure, arrhythmia, hyperepinephry, hyperthyroidism, asthma and chronic obstructive pulmonary disease.

[6-5] The compound according to [6-2] or a salt thereof, wherein the pain is selected from the group consisting of chronic pain, psychogenic pain, neuropathic pain, phantom pain, postherpetic neuralgia, traumatic neck syndrome, spinal cord injury pain, trigeminal neuralgia and diabetic neuropathy.

[7-1] Use of a compound according to any one of [1-1] to [1-5] or a salt thereof in the manufacture of a medicament for treating, preventing and/or diagnosing a disorder associated with serotonin, norepinephrine and/or dopamine nerve dysfunction.

[7-2] The use according to [7-1], wherein the disorder is selected from the group consisting of attention-deficit hyperactivity disorder (ADHD), Tourette's disorder, autism spectrum disorder, Asperger's syndrome, depression; depressive symptoms in adjustment disorder; anxiety in adjustment disorder, anxiety associated with various disorders, generalized anxiety disorder, phobias, obsessive-compulsive disorder, panic disorder, post-traumatic stress disorder, acute stress disorder, hypochondriac, dissociative amnesia, avoidant personality disorder, body dysmorphic disorder, eating disorder, obesity, chemical dependence, pain, fibromyalgia, apathy, Alzheimer's disease, memory impairment, Parkinson's disease, restless leg syndrome, endocrine disorder, hypertension, vasospasm, cerebellar ataxia, gastrointestinal tract disorder, negative symptoms in schizophrenia, affective disorders in schizophrenia, cognitive dysfunction in schizophrenia, premenstrual syndrome, stress urinary incontinence, urge urinary incontinence, impulse control disorders, trichotillomania, kleptomania, gambling addiction, cluster headache, migraine, chronic paroxysmal hemicrania, chronic fatigue, premature ejaculation, male impotence, narcolepsy, primary hypersomnia, atonic seizure, sleep apnea syndrome and headache.

[7-3] The use according to [7-2], wherein the depression is selected from the group consisting of major depressive disorder; bipolar I disorder; bipolar II disorder; mixed bipolar disorder; dysthymic disorder; rapid cycler; atypical depression; seasonal affective disorder; postpartum depression; mild depression; recurrent brief depressive disorder; refractory depression-chronic depression; treatment-resistant depression; alcohol-induced mood disorder; mixed anxiety-depressive disorder; depressions associated with various disorders such as Cushing's syndrome, hypothyroidism, hyperparathyroidism, Addison's disease, amenorrhea-galactorrhea syndrome, Parkinson's disease, Alzheimer's disease, cerebrovascular dementia, cerebral infarction, cerebral hemorrhage, subarachnoid hemorrhage, diabetes, viral infection, multiple sclerosis, chronic fatigue syndrome, coronary artery disease, pain, and cancer; middle-age depression; elderly depression; childhood and adolescent depression; and depression induced by a drug such as interferon.

[7-4] The use according to [7-2], wherein the anxiety associated with various disorders is selected from the group consisting of head trauma, brain infection, inner ear disorder, heart failure, arrhythmia, hyperepinephry, hyperthyroidism, asthma and chronic obstructive pulmonary disease.

[7-5] The use according to [7-2], wherein the pain is selected from the group consisting of chronic pain, psychogenic pain, neuropathic pain, phantom pain, postherpetic neuralgia, traumatic neck syndrome, spinal cord injury pain, trigeminal neuralgia and diabetic neuropathy.

[8] Use of a compound according to any one of [1-1] to [1-5] or a salt thereof as serotonin reuptake inhibitor, norepinephrine reuptake inhibitor and/or dopamine reuptake inhibitor.

Effect of the Invention

Drugs inhibiting reuptake of serotonin, norepinephrine and/or dopamine with appropriate strength and rate are expected to be therapeutic drugs having a combination of excellent properties of both stimulants and non-stimulants.

The present compound inhibits the reuptake of the three monoamines mentioned above in a potent and optimal ratio in vitro studies. Also, the present compound has an effect to continuously increase extracellular monoamine levels in the prefrontal cortex and striatum from low doses by oral administration in an in vivo microdialysis study in rats. Furthermore, the present compound shows an improvement effect from low doses by oral administration in the evaluation of improvement of hyperactivity-like and impulsivity-like symptom in stroke-prone spontaneously hypertensive rats (SHRSP).

DESCRIPTION OF EMBODIMENTS

The terms and phrases used in the present description will be described in detail below.

In the present description, the "halogen" is fluorine, chlorine, bromine, or iodine. It is preferably fluorine, chlorine, or bromine, and more preferably fluorine or chlorine.

In the present description, the "$C_{1-6}$ alkyl" is linear or branched alkyl having 1 to 6 carbon atoms ($C_{1-6}$), and specific examples thereof include methyl, ethyl, n-propyl, isopropyl, n-butyl, isobutyl, sec-butyl, tert-butyl, n-pentyl, isopentyl, neopentyl, n-hexyl, isohexyl, 3-methylpentyl, and the like.

In addition, the "$C_{1-6}$ alkyl" includes $C_{1-6}$ alkyl in which 1 to 7 hydrogen atoms are substituted by deuterium atoms.

In the present description, the "$C_{1-6}$ alkoxy" is linear or branched alkoxy having 1 to 6 carbon atoms ($C_{1-6}$), and specific examples thereof include methoxy, ethoxy, n-propoxy, isopropoxy, n-butoxy, isobutoxy, sec-butoxy, tert-butoxy, n-pentoxy, isopentoxy, neopentoxy, n-hexyloxy, isohexyloxy, 3-methylpentoxy, and the like.

In the present description, the "$C_{3-8}$ cycloalkane" is cycloalkane having 3 to 8 carbon atoms ($C_{3-8}$), and specific examples thereof include cyclopropane, cyclobutane, cyclopentane, cyclohexane, cycloheptane, cyclooctane, and the like.

In the present description, the "9- to 10-membered bicyclic ring system containing oxygen atom as ring-constituting atom together with a benzene ring" is a fused ring composed of a saturated or unsaturated 5- to 6-membered heterocyclic ring containing one oxygen atom as ring-constituting atom and a benzene ring, and specific examples thereof include benzofuran, dihydrobenzofuran, benzopyran, dihydrobenzopyran, etc.

In the present description, the "protecting group" is not particularly limited as long as it functions as a protecting group, and examples thereof include alkyl groups (e.g., methyl, ethyl, isopropyl, tert-butyl, trifluoromethyl, hydroxymethyl, 2-hydroxyethyl, and acetylmethyl); alkyl (alkenyl)carbonyl groups (e.g., acetyl, propionyl, butyryl, isobutyryl, pentanoyl, pivaloyl, valeryl, isovaleryl, chloroacetyl, dichloroacetyl, trichloroacetyl, trifluoroacetyl, methoxyacetyl, acryloyl, propioloyl, methacryloyl, crotonoyl, isocrotonoyl, and (E)-2-methyl-2-butenoyl); arylcarbonyl groups (e.g., benzoyl, α-naphthoyl, β-naphthoyl, 2-bromobenzoyl, 4-chlorobenzoyl, 2,4,6-trimethylbenzoyl, 4-toluoyl, 4-anisoyl, 4-nitrobenzoyl, 2-nitrobenzoyl, 2-(methoxycarbonyl)benzoyl, and 4-phenylbenzoyl); tetrahydro(thio)pyranyl(furanyl) groups (e.g., tetrahydropyran-2-yl and 3-bromotetrahydropyran-2-yl); silyl groups (e.g., trimethylsilyl, triethylsilyl, isopropyldimethylsilyl, tert-butyldimethylsilyl, tert-butyldiphenylsilyl, methyldiisopropylsilyl, methyl-di-tert-butylsilyl, triisopropylsilyl, diphenylmethylsilyl, diphenylbutylsilyl, diphenylisopropylsilyl, phenyldiisopropylsilyl, triphenylsilyl, and di-tert-butyl-isobutylsilyl); alkoxymethyl groups (e.g., methoxymethyl, 1,1-dimethyl-1-methoxymethyl, ethoxymethyl, propoxymethyl, iso-propoxymethyl, butoxymethyl, tert-butoxymethyl, 2-methoxyethoxymethyl, 2,2,2-trichloroethoxymethyl, and bis(2-chloroethoxy)methyl); aralkyl groups (e.g., benzyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, and 4-cyanobenzyl); carbamate groups (e.g., tert-butylcarbamate, allylcarbamate, and benzylcarbamate); and the like.

In the present description, the "silyl protecting group" is not particularly limited as long as it functions as a protecting group containing silicon, and examples thereof include trimethylsilyl, triethylsilyl, isopropyldimethylsilyl, tert-butyldimethylsilyl, tert-butyldiphenylsilyl, methyldiisopropylsilyl, methyldi-tert-butylsilyl, triisopropylsilyl, diphenylmethylsilyl, diphenylbutylsilyl, diphenylisopropylsilyl, phenyldiisopropylsilyl, triphenylsilyl, di-tert-butylisobutylsilyl, and the like.

In the present description, the "protecting agent" is not particularly limited as long as it can introduce a protecting group to a target functional group, and examples thereof include alkylating agents (e.g., dimethyl sulfate, diazomethane, methyl bromide, methyl iodide, Meerwein's reagent, methyl trifluoromethanesulfonate, ethyl bromide, isobutylene, 2-hydroxyethyl bromide); alkyl(alkenyl) carbonylating agents (e.g., acetic anhydride, acetyl chloride, ketene, propionyl chloride, butyryl chloride, pivaloyl chloride, chloroacetyl chloride, trifluoroacetic anhydride); aryl carbonylating agents (e.g., benzoyl chloride, benzoic anhydride, benzoyl cyanide, α-naphthoyl chloride); tetrahydro(thio) pyranylating(furanylating) agents (3,4-dihydro-2H-pyran, 2,3-dihydrofuran, 2-chlorotetrahydrofuran); silylating agent (e.g., trimethylsilyl chloride, triethylsilyl chloride, isopropyldimethylsilyl chloride, tert-butyldimethylsilyl chloride, methyldiisopropylsilyl chloride, methyldi-tert-butylsilyl chloride, triisopropylsilyl chloride, diphenylmethylsilyl chloride, diphenylbutylsilyl chloride, diphenylisopropylsilyl chloride, phenyldiisopropylsilyl chloride, triphenylsilyl chloride, or di-tert-butylisobutylsilyl triflate is used with base such as imidazole, pyridine, 2,6-rutidine, etc.); alkoxymethylating agents (e.g., methoxymethyl chloride, methoxymethyl bromide, di-dimethoxymethane, ethoxymethyl chloride, 2-methoxyethoxymethyl chloride, 2,2,2-trichloroethoxymethyl chloride, 2-trimethylsilylethoxymethyl chloride, benzyloxyethoxymethyl chloride, ethyl vinyl ether); aralkylating agents (e.g., benzyl chloride, benzyl bromide, benzyl 2,2,2-trichloroacetimidate, 4-methoxybenzyl chloride, triphenylmethyl chloride, triphenylmethyl bromide); carbamates (e.g., di-tert-butyl dicarbonate, allyl chloroformate, diallyl dicarbonate, benzyl chloroformate, benzyl dicarbonate); and the like.

In the present description, the "deprotecting agent" is not particularly limited as long as it can deprotect a protecting group, and examples thereof include alkyl groups (e.g., trimethylsilyl iodide, boron tribromide, aluminum chloride/ethanethiol); alkyl(alkenyl)carbonyl groups (e.g., strong alkaline aqueous solution, aqueous ammonia, methylamine, 2-aminoethanethiol, thiourea, tetrabutylammonium hydroxide, diisobutyl aluminum hydride, lithium aluminum hydride, hydrazine, boron trifluoride diethyl ether complex/dimethyl sulfide); arylcarbonyl groups [deprotecting agents for alkyl(alkenyl)carbonyl groups can be used]; tetrahydropyranyl(furanyl) groups (e.g. pyridinium p-toluene sulfonate, p-toluenesulfonic acid, acetic acid, hydrochloric acid, trifluoroacetic acid); silyl groups (e.g., tetra-n-butylammonium fluoride/tetrahydrofuran, potassium carbonate/methanol, 2% hydrofluoric acid, hydrofluoric acid/pyridine); alkoxymethyl groups (e.g., pyridinium p-toluene sulfonate, thiophenol/boron trifluoride diethyl ether complex, catechol boron bromide, trimethylsilyl bromide, bromodimethylborane, lithium tetrafluoroborate, hydrochloric acid, trifluoroacetic acid, zinc dibromide, titanium tetrachloride, trimethylsilyl chloride/sodium iodide, tetrafluoroboric acid, zinc, zinc/copper, lithium/ammonia); allyl groups (e.g., hydrogen/palladium carbon, ammonium formate/palladium carbon, Raney nickel, trimethylsilyl iodide, boron tribromide, boron trichloride, dichlorodicyanoquinone, cerium ammonium nitrite); carbamates (examples of deprotecting agent for tert-butyl carbamate group include hydrochloric acid/ethyl acetate, trifluoroacetic acid, trimethylsilyl iodide, aluminum chloride/anisole, etc.; examples of deprotecting agent for allylcarbamate group include palladium(0) catalysts (e.g., tetrakis(triphenylphosphine)palladium, tris(dibenzylideneacetone)dipalladium, etc.) in combination with nucleophiles (morpholine, dimedone, formic acid, 2-ethylhexanoic acid, etc.), iodine/aqueous acetonitrile, etc.; examples of deprotecting agent for benzylcarbamate group include contact hydrolysis with palladium carbon, trimethylsilyl iodide, trifluoroacetic acid, etc.); and the like.

In the present description, the "silyl protecting agent" is not particularly limited as long as it can introduce a silyl protecting group to a target functional group, and examples thereof include trimethylsilyl chloride, triethylsilyl chloride, isopropyldimethylsilyl chloride, tert-butyldimethylsilyl chloride, methyldiisopropylsilyl chloride, methyldi-tert-butylsilyl chloride, triisopropylsilyl chloride, diphenylmethylsilyl chloride, diphenylbutylsilyl chloride, diphenylisopropylsilyl chloride, phenyldiisopropylsilyl chloride, triphenylsilyl chloride, di-tert-butylisobutylsilyltriflate, and the like.

In the present description, the "silyl deprotecting agent" is not particularly limited as long as it can deprotect a silyl protecting group, and examples thereof include formic acid, acetic acid, hydrochloric acid, trifluoroacetic acid, hydrofluoric acid, tetra-n-butylammonium fluoride, and the like.

In the present description, the "alkylating agent" is not particularly limited as long as it can alkylate a target functional group, and examples thereof include dimethyl sulfate, diazomethane, methyl bromide, methyl iodide, Meerwein's reagent, methyl trifluoromethanesulfonate, ethyl bromide, isobutylene, 2-hydroxyethyl bromide, and the like.

In the present description, the "peroxide" is not particularly limited as long as it can form oxide, and examples thereof include potassium peroxymonosulfate (Oxone (registered trademark)), m-chloroperbenzoic acid (MCPBA), perbenzoic acid, peracetic acid, trifluoroperacetic acid, sodium periodate, hydrogen peroxide, 3,3-dimethyldioxirane, N-(benzenesulfonyl)-3-phenyloxaziridine, magnesium monoperoxyphthalate hexahydrate, tert-butylhydroperoxide, sodium bromate, potassium permanganate, manganese dioxide, selenium dioxide, chromium trioxide, sodium perborate, tetrapropylammonium perruthenate, and the like.

In the present description, the "palladium reagent" is not particularly limited, and examples thereof include tetravalent palladium catalysts such as sodium hex-achloropalladium(IV) acid tetrahydrate and potassium hexachloropalladium(IV) acid; divalent palladium catalysts such as [1,1'-bis(diphenylphosphino)ferrocene]palladium(II) dichloride dichloromethane adduct ($Pd(dppf)Cl_2 \cdot CH_2Cl_2$), (2-dicyclohexylphosphino-2',4',6'-triisopropyl-1,1'-biphenyl)[2-(2'-amino-1,1'-biphe nyl)]palladium(II) methanesulfonate (XPhos Pd G3), palladium(II) chloride, palladium(II) bromide, palladium(II) acetate, palladium(II) acetylacetonate, dichlorobis(benzonitrile)palladium(II), dichlorobis(acetonitrile)palladium(II), dichlorobis(triphenylphosphine)palladium(II), dichlorotetraammine palladium(II), dichloro(cycloocta-1,5-diene)palladium(II), and palladium(II) trifluoroacetate, and 1,1'-bis(diphenylphosphino)ferrocene dichloropalladium(II) dichloromethane complex; and zerovalent palladium catalysts such as tris(dibenzylideneacetone)dipalladium(0) ($Pd_2(dba)_3$), tris(dibenzylideneacetone)dipalladium(0)-chloroform complex, and tetrakis(triphenylphosphine)palladium(0) ($Pd(PPh_3)_4$). These palladium reagents are used alone or as a mixture of two or more of them.

In the present description, the "phosphine ligand" is not particularly limited, and examples thereof include triphenylphosphine, tri(o-tolyl)phosphine, tri-tert-butylphosphonium tetrafluoroborate, tricyclohexylphosphonium tetrafluoroborate, pentaphenyl(di-tert-butylphosphino) ferrocene, 4,5-bis(diphenylphosphino)-9,9-dimethylxanthene (Xantphos), bis[2-(diphenylphosphino)phenyl]ether (DPEPhos), 2,2'-bis(diphenylphosphino)-1,1'-binaphthyl (BINAP), 1,1'-bis(diphenylphosphino)ferrocene (dppf), 2-dicyclohexylphosphino-2',4',6'-triisopropyl-1,1'-biphenyl (XPhos), 2-dicyclohexylphosphino-2',6'-diisopropoxy-1,1'-biphenyl (RuPhos), and the like.

In the present description, the "reducing agent" is not limited as long as it can reduce a target functional group, and examples thereof include lithium aluminum hydride, diisobutyl aluminum hydride, sodium dihydrobis(2-methoxyethoxy)aluminate, lithium borohydride, and the like.

In the present description, examples of the "base" include an inorganic base, an organic base, and the like. Examples of the "inorganic base" include an alkali metal hydroxide (e.g., sodium hydroxide and potassium hydroxide), an alkaline earth metal hydroxide (e.g., magnesium hydroxide and calcium hydroxide), an alkali metal carbonate (e.g., sodium carbonate and potassium carbonate), an alkaline earth metal carbonate (e.g., magnesium carbonate and calcium carbonate), an alkali metal hydrogen carbonate (e.g., sodium hydrogen carbonate and potassium hydrogen carbonate), an alkali metal phosphate (e.g., sodium phosphate and potassium phosphate), an alkaline earth metal phosphate (e.g., magnesium phosphate and calcium phosphate), and the like. Examples of the "organic base" include trialkylamines (e.g., trimethylamine, triethylamine, and diisopropylethylamine), picoline, 1,5-diazabicyclo[4.3.0]non-5-ene, 1,4-diazabicyclo[2.2.2]octane, 1,8-diazabicyclo[5.4.0]undec-7-ene, and the like.

In the present description, examples of the "leaving group" include halogen, $C_{1-18}$ alkanesulfonyl, lower alkanesulfonyloxy, arylsulfonyloxy, aralkylsulfonyloxy, perhaloalkanesulfonyloxy, sulfonio, toluenesulfoxy, and the like. A preferable leaving group is halogen.

The "halogen" is fluorine, chlorine, bromine, or iodine.

Examples of the "$C_{1-18}$ alkanesulfonyl" include linear or branched alkanesulfonyl having 1 to 18 carbon atoms ($C_{1-18}$), and specific examples thereof include methanesulfonyl, 1-propanesulfonyl, 2-propanesulfonyl, butanesulfonyl, cyclohexanesulfonyl, dodecanesulfonyl, octadecanesulfonyl, and the like.

Examples of the "lower alkanesulfonyloxy" include linear or branched alkanesulfonyloxy having 1 to 6 carbon atoms ($C_{1-6}$), and specific examples thereof include methanesulfonyloxy, ethanesulfonyloxy, 1-propanesulfonyloxy, 2-propanesulfonyloxy, 1-butanesulfonyloxy, 3-butanesulfonyloxy, 1-pentanesulfonyloxy, 1-hexanesulfonyloxy, and the like.

Examples of the "arylsulfonyloxy" include phenylsulfonyloxy optionally having 1 to 3 groups selected from the group consisting of linear or branched alkyl having 1 to 6 carbon atoms ($C_{1-6}$), linear or branched alkoxy having 1 to 6 carbon atoms ($C_{1-6}$), nitro and halogen, as a substituent on the phenyl ring, naphthylsulfonyloxy, and the like. Specific examples of the "phenylsulfonyloxy optionally having substituent(s)" include phenylsulfonyloxy, 4-methylphenylsulfonyloxy, 2-methylphenylsulfonyloxy, 4-nitrophenylsulfonyloxy, 4-methoxyphenylsulfonyloxy, 2-nitrophenylsulfonyloxy, 3-chlorophenylsulfonyloxy, and the like. Specific examples of the "naphthylsulfonyloxy" include α-naphthylsulfonyloxy, β-naphthylsulfonyloxy, and the like.

Examples of the "aralkylsulfonyloxy" include linear or branched alkanesulfonyloxy having 1 to 6 carbon atoms ($C_{1-6}$), which is substituted by phenyl optionally having 1 to 3 groups selected from the group consisting of linear or branched alkyl having 1 to 6 carbon atoms ($C_{1-6}$), linear or branched alkoxy having 1 to 6 carbon atoms ($C_{1-6}$), nitro and halogen, as a substituent on the phenyl ring; and linear or branched alkanesulfonyloxy having 1 to 6 carbon atoms ($C_{1-6}$), which is substituted by naphthyl, and the like. Specific examples of the "alkanesulfonyloxy substituted by phenyl" include ben-zylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, and the like. Specific examples of the "alkanesulfonyloxy substituted by naphthyl" include α-naphthylmethylsulfonyloxy, β-naphthylmethylsulfonyloxy, and the like.

Specific examples of the "perhaloalkanesulfonyloxy" include trifluoromethanesul-fonyloxy and the like.

Specific examples of the "sulfonio" include dimethylsulfonio, diethylsulfonio, dipropylsulfonio, di(2-cyanoethyl)sulfonio, di(2-nitroethyl)sulfonio, di-(aminoethyl) sulfonio, di(2-methylaminoethyl)sulfonio, di-(2-dimethylaminoethyl)sulfonio, di-(2-hydroxyethyl)sulfonio, di-(3-hydroxypropyl)sulfonio, di-(2-methoxyethyl)sulfonio, di-(2-carbamoylethyl)sulfonio, di-(2-carbamoylethyl)sulfonio, di-(2-carboxyethyl)sulfonio, di-(2-methoxycarbonylethyl)sulfonio, diphenylsulfonio, and the like.

In the present description, the "solvent" may be an inert solvent in the reactions, and examples thereof include water, ethers (e.g., dioxane, tetrahydrofuran, diethyl ether, 1,2-dimethoxyethane, diethylene glycol dimethyl ether, and ethylene glycol dimethyl ether), halohydrocarbons (e.g., methylene chloride, chloroform, 1,2-dichloroethane, and carbon tetrachloride), aromatic hydrocarbons (e.g., benzene, toluene, and xylene), lower alcohols (e.g., methanol, ethanol, and isopropanol), and polar solvents (e.g., N,N-dimethylformamide (DMF), N-methylpyrrolidone (NMP), dimethyl sulfoxide (DMSO), hexamethylphosphoric triamide, and acetonitrile). These solvents are used alone or as a mixture of two or more of them. In addition, no solvent may be used in the reactions.

The individual substituents in the compound represented by general formula [I] of the present invention (hereafter referred to as "compound [I]") are explained below.

The general formula [I] is preferably general formula [Ia], general formula [Ib], general formula [Ic] or general formula [Id], more preferably general formula [Ia] or general formula [Ib].

$R^{11}$, $R^{12}$ and $R^{13}$ in the compound [I] is are the same or different and each independently represents hydrogen or $C_6$ alkyl, preferably hydrogen, methyl, ethyl, 1-propyl or 2-propyl.

In another embodiment, $R^{11}$ and $R^{12}$ in the compound [I] together with the adjacent carbon atom form a 3- to 8-membered cycloalkane, which is preferably cyclopropane, cyclobutane, cyclopentane, cyclohexane, cycloheptane, or cyclooctane, more preferably cyclobutane.

$R^{22}$, $R^{23}$, $R^{25}$ and $R^{26}$ in the compound [I] are the same or different and each independently represents hydrogen, halogen, $C_{1-6}$ alkyl or $C_{1-6}$ alkoxy; preferably hydrogen, fluorine, chlorine, methyl or methoxy, more preferably hydrogen, fluorine, chlorine or methyl.

In another embodiment, $R^{22}$ and $R^{23}$ in the compound [I] form a 9- to 10-membered bicyclic ring system containing oxygen atom as ring-constituting atom together with a benzene ring adjacent to them, which is preferably benzofuran, dihydrobenzofuran, benzopyran or dihydrobenzopyran, more preferably benzofuran or benzopyran.

$R^{31}$ and $R^{32}$ in the compound [I] are the same or different and each independently represents hydrogen or halogen; preferably hydrogen, fluorine or chlorine.

In one embodiment of the present invention, $R^{11}$, $R^{12}$ and $R^{13}$ are the same or different and each independently represents hydrogen or $C_{1-6}$ alkyl, preferably hydrogen or methyl;

$R^{22}$, $R^{23}$, $R^{25}$ and $R^{26}$ are the same or different and each independently represents hydrogen, halogen, $C_{1-6}$ alkyl or $C_{1-6}$ alkoxy, preferably hydrogen, fluorine, chlorine, methyl or methoxy;

$R^{31}$ and $R^{32}$ are the same or different and each independently represents hydrogen or halogen, preferably hydrogen or fluorine.

In another embodiment of the present invention, $R^{11}$ and $R^{12}$ together with the adjacent carbon atom form a 3- to 8-membered cycloalkane, preferably cyclobutyl, $R^{13}$ is hydrogen or $C_{1-6}$ alkyl, preferably hydrogen or methyl, $R^{22}$, $R^{23}$, $R^{25}$ and $R^{26}$ are the same or different and each independently represents hydrogen, halogen, $C_{1-6}$ alkyl or $C_{1-6}$ alkoxy, preferably hydrogen, fluorine, chlorine, methyl or methoxy;

$R^{31}$ and $R^{32}$ are the same or different and each independently represents hydrogen or halogen, preferably hydrogen or fluorine.

In the other embodiment of the present invention, $R^{11}$, $R^{12}$ and $R^{13}$ are the same or different and each independently represents hydrogen or $C_{1-6}$ alkyl, preferably hydrogen or methyl;

$R^{22}$ and $R^{23}$ form a 9- to 10-membered bicyclic ring system containing oxygen atom as ring-constituting atom together with a benzene ring adjacent to them, preferably benzofuran;

$R^{25}$ and $R^{26}$ are the same or different and each independently represents hydrogen, halogen, $C_{1-6}$ alkyl or $C_{1-6}$ alkoxy, preferably hydrogen, fluorine, chlorine, methyl or methoxy;

$R^{31}$ and $R^{32}$ are the same or different and each independently represents hydrogen or halogen, preferably hydrogen or fluorine.

In the other embodiment of the present invention, $R^{11}$ and $R^{12}$ together with the adjacent carbon atom form a 3- to 8-membered cycloalkane, preferably cyclobutyl, $R^{13}$ is hydrogen or $C_{1-6}$ alkyl, preferably hydrogen or methyl, $R^{22}$ and $R^{23}$ form a 9- to 10-membered bicyclic ring system containing oxygen atom as ring-constituting atom together with a benzene ring adjacent to them, preferably benzofuran;

$R^{25}$ and $R^{26}$ are the same or different and each independently represents hydrogen, halogen, $C_{1-6}$ alkyl or $C_{1-6}$ alkoxy, preferably hydrogen, fluorine, chlorine, methyl or methoxy;

$R^{31}$ and $R^{32}$ are the same or different and each independently represents hydrogen or halogen, preferably hydrogen or fluorine.

In the other preferred embodiment of the present invention, the general formula [I]:

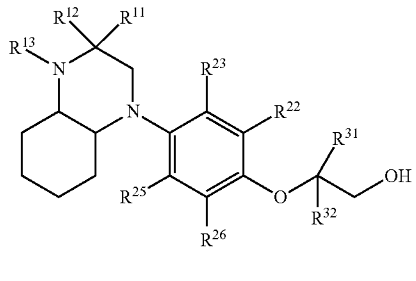

is

-continued

[IIa]

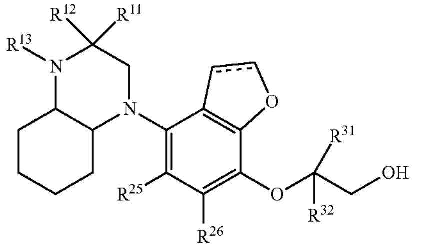

or

[IIb]

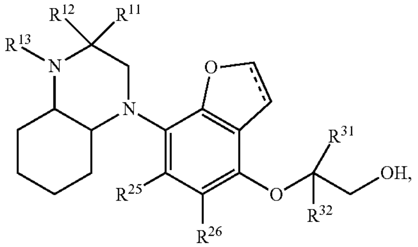

, wherein $R^{11}$, $R^{12}$ and $R^{13}$ are the same or different and each independently represents hydrogen or $C_{1-6}$ alkyl, preferably hydrogen or methyl;

$R^{25}$ and $R^{26}$ are the same or different and each independently represents hydrogen, halogen, $C_{1-6}$ alkyl or $C_{1-6}$ alkoxy, preferably hydrogen, fluorine, chlorine, methyl or methoxy;

$R^{31}$ and $R^{32}$ are the same or different and each independently represents hydrogen or halogen, preferably hydrogen or fluorine;

--- is single bond or double bond, preferably double bond.

In the other embodiment of the present invention, $R^{11}$ and $R^{12}$ together with the adjacent carbon atom form a 3- to 8-membered cycloalkane, preferably cyclobutyl;

$R^{13}$ is hydrogen or $C_{1-6}$ alkyl, preferably hydrogen or methyl;

$R^{22}$ and $R^{23}$ form a 9- to 10-membered bicyclic ring system containing oxygen atom as ring-constituting atom together with a benzene ring adjacent to them, preferably benzofuran;

$R^{25}$ and $R^{26}$ are the same or different and each independently represents hydrogen, halogen, $C_{1-6}$ alkyl or $C_{1-6}$ alkoxy, preferably hydrogen, fluorine, chlorine, methyl or methoxy;

$R^{31}$ and $R^{32}$ are the same or different and each independently represents hydrogen or halogen, preferably hydrogen or fluorine.

In the other preferred embodiment of the present invention, the general formula [I]:

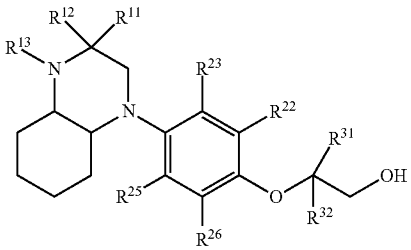

is

-continued

[IIa]

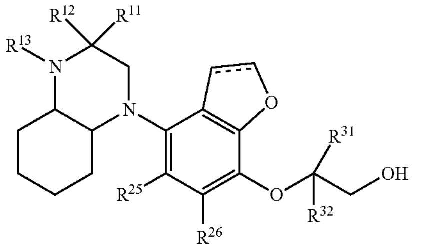

or

[IIb]

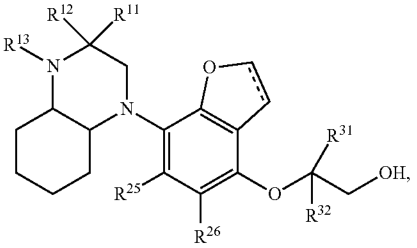

, wherein $R^{11}$ and $R^{12}$ together with the adjacent carbon atom form a 3- to 8-membered cycloalkane, preferably cyclobutyl;

$R^{13}$ is hydrogen or $C_{1-6}$ alkyl;

$R^{25}$ and $R^{26}$ are the same or different and each independently represents hydrogen, halogen, $C_{1-6}$ alkyl or $C_{1-6}$ alkoxy;

$R^{31}$ and $R^{32}$ are the same or different and each independently represents hydrogen or halogen;

--- is single bond or double bond.

Specific embodiments of the compound [I] of the present invention include the following compounds:

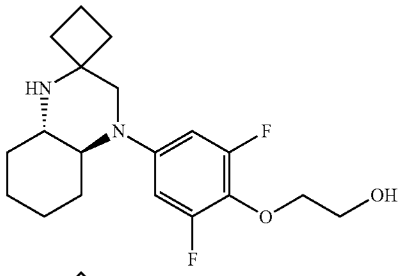

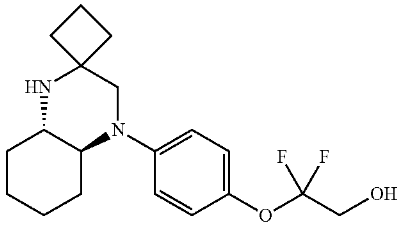

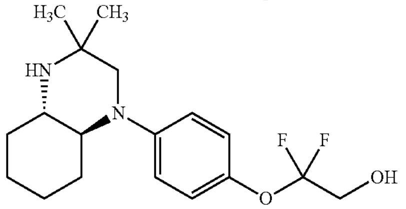

-continued

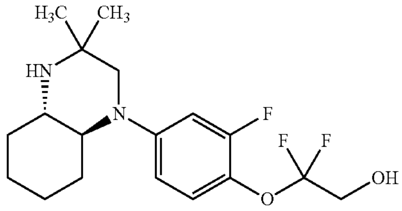

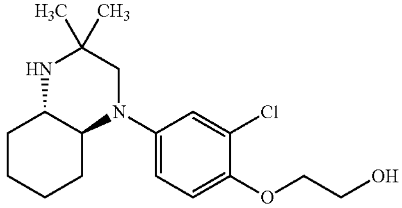

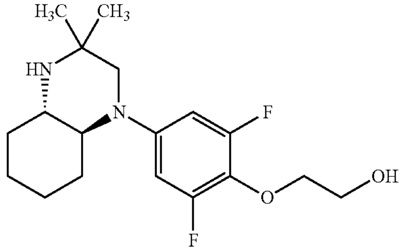

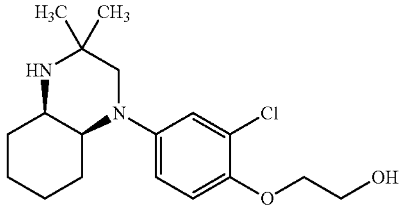

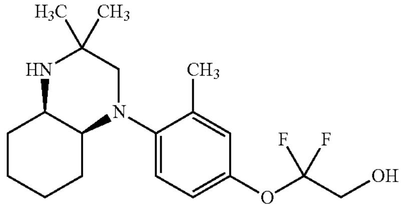

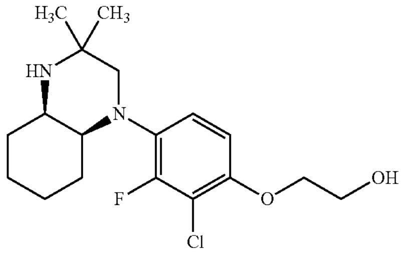

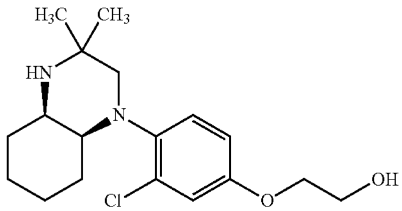

-continued

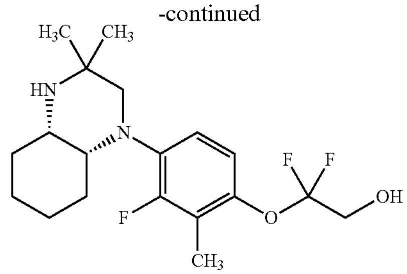

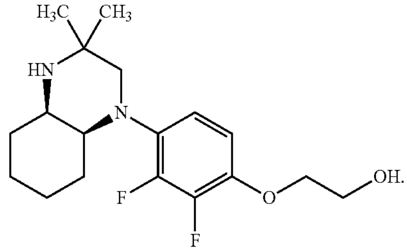

In the present description, preferred embodiments and alternatives regarding diverse features of the compound [I] or a salt thereof, use, method, and composition of the present invention can be combined, and unless this is incompatible with the nature thereof, the presentation of the combination of preferred embodiments and alternatives regarding the diverse features is also included.

The method for manufacturing the compound [I] will be described below. The compound [I] can be manufactured according to the method for manufacturing described below. These methods for manufacturing are examples and the method for manufacturing the compound [I] is not limited thereto.

In the reaction formulae below, in the case of performing alkylation reaction, hydrolysis reaction, amination reaction, esterification reaction, amidation reaction, etheri-fication reaction, nucleophilic substitution reaction, addition reaction, oxidation reaction, reduction reaction, and the like, these reactions are performed according to methods known per se. Examples of such methods include the methods described in The 5th Series of Experimental Chemistry (The Chemical Society of Japan ed., Maruzen Co., Ltd.); Organic Functional Group Preparations, 2nd edition, Academic Press, Inc. (1989); Comprehensive Organic Transformations, VCH Publishers Inc. (1989); Greene's Protective Groups in Organic Synthesis, 4th edition, (2006) written by P. G. M. Wuts and T. W. Greene; and the like.

General Synthetic Pathways of the Compound [I]

1) Synthetic Pathway (1) of Compound [I]

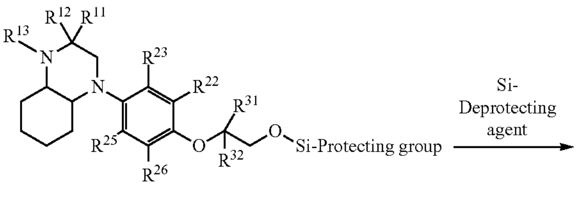

[2]

-continued

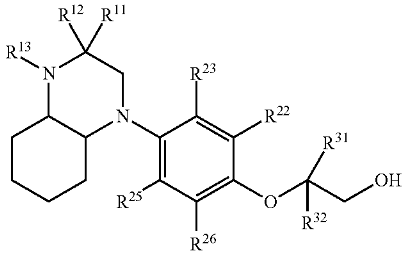

[1]

wherein symbols are as defined above.

The compound [1] of the present invention can be manufactured by the reaction indicated by the synthetic pathway described above. Specifically, the compound [1] can be manufactured by deprotection of the silyl protecting group (Si-Protecting group) in the compound [2] with a silyl deprotecting agent (Si-Deprotecting agent) in an inert solvent for the reaction.

2) Synthetic Pathway (2) of Compound [I]

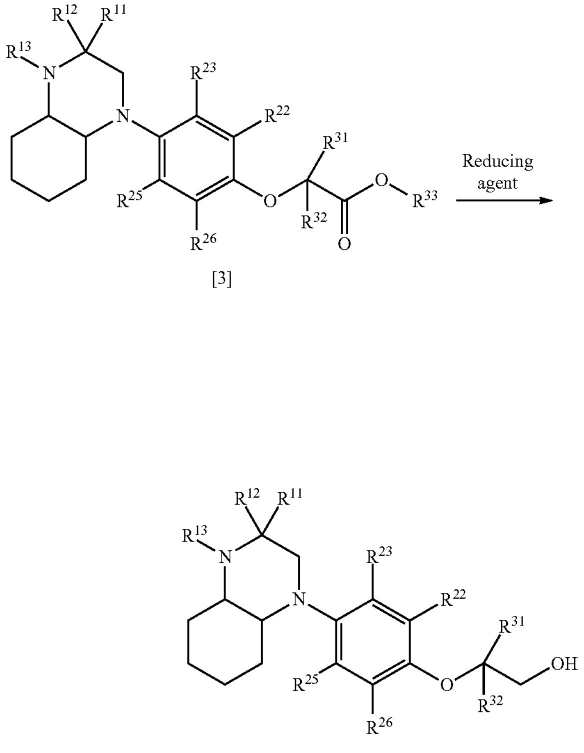

[3]

[1]

wherein $R^{33}$ is $C_{1-6}$ alkyl, and the other symbols are as defined above.

The compound [1] of the present invention can be manufactured by the reaction indicated by the synthetic pathway described above. Specifically, the compound [1] can be manufactured by reduction of the compound [3] in an inert solvent for the reaction in the presence of a reducing agent.

3) Synthetic Pathway (1) of Intermediate [2]

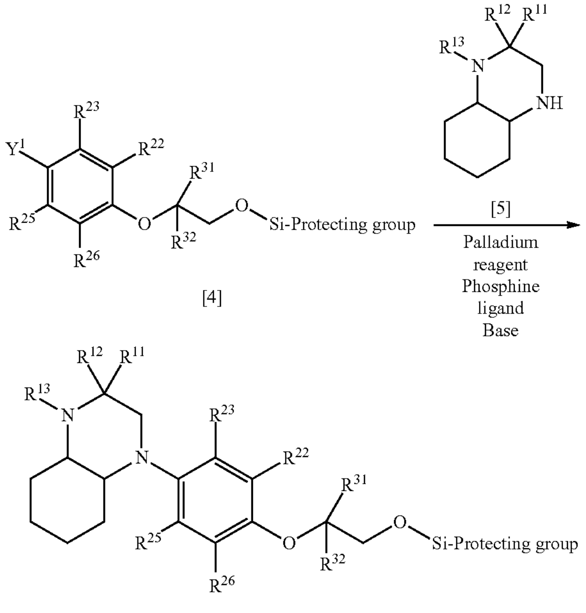

[4]

[2]

wherein $Y^1$ is a leaving group, and the other symbols are as defined above.

The intermediate [2] of the compound [1] of the present invention can be manufactured by the reaction indicated by the synthetic pathway described above. Specifically, the intermediate [2] can be manufactured by condensation of the compound [4] and the compound [5] in an inert solvent for the reaction in presence of a palladium reagent, a phosphine ligand and a base.

4) Synthetic Pathway (2) of Intermediate [2]

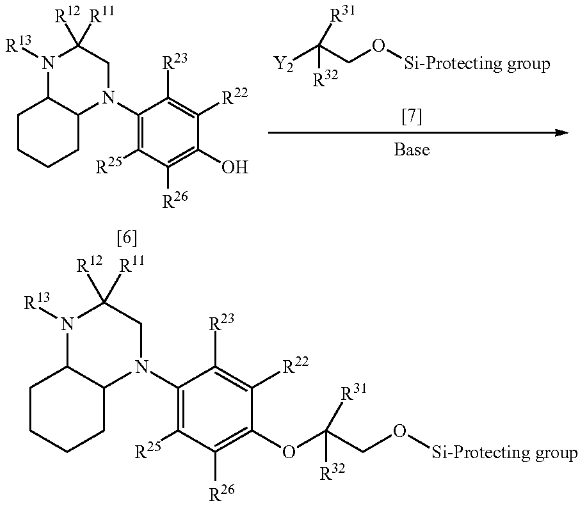

[6]

[2]

wherein $Y^2$ is a leaving group, and the other symbols are as defined above.

The intermediate [2] of the compound [1] of the present invention can be manufactured by the reaction indicated by the synthetic pathway described above.

Specifically, the intermediate [2] can be manufactured by condensation reaction of the compound [6] and the compound [7] in an inert solvent for the reaction in presence of a base.

5) Synthetic Pathway of Intermediate [3]

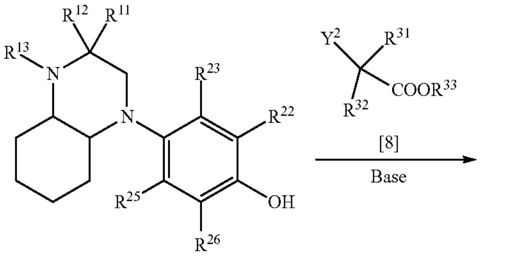

[6]

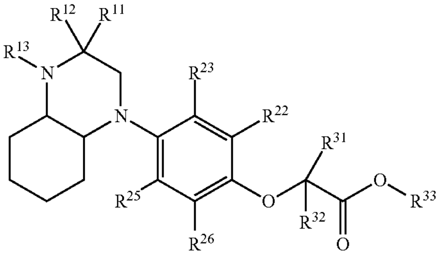

[3]

wherein $Y^2$ is a leaving group, $R^{33}$ is $C_{1-6}$ alkyl, and the other symbols are as defined above.

The intermediate [3] of the compound [1] of the present invention can be manufactured by the reaction indicated by the synthetic pathway described above. Specifically, the intermediate [3] can be manufactured by condensation reaction of the compound [6] and the compound [8] in an inert solvent for the reaction in presence of a base.

6) Synthetic Pathway (1) of Intermediate [4]

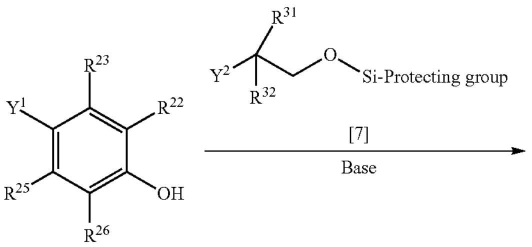

[9]

-continued

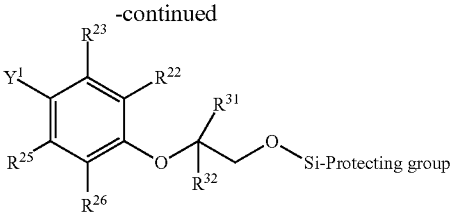

[5]

wherein $Y^1$ and $Y^2$ are leaving groups, and the other symbols are as defined above.

The intermediate [4] of the compound [1] of the present invention can be manufactured by the reaction indicated by the synthetic pathway described above. Specifically, the intermediate [4] can be manufactured by reacting the compound [9] with the compound [7] in an inert solvent for the reaction in presence of a base.

7) Synthetic Pathway (2) of Intermediate [4]

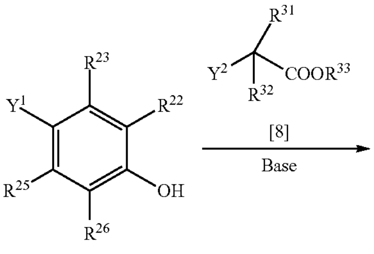

[9]

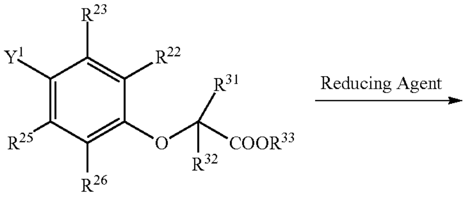

[10]

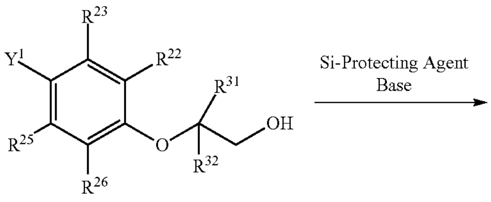

[11]

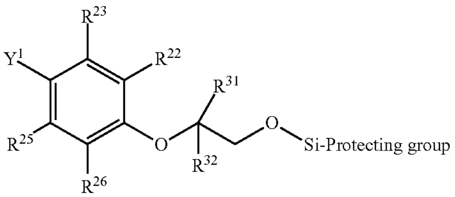

[4]

wherein $Y^1$ and $Y^2$ are leaving groups, $R^{33}$ is $C_{1-6}$ alkyl, and the other symbols are as defined above.

The intermediate [4] of the compound [1] of the present invention can be manufactured by the reaction indicated by the synthetic pathway described above. Specifically, first, the intermediate [10] can be manufactured by condensation reaction of the compound [9] and the compound [8] in an inert solvent for the reaction in presence of a base. Next, the intermediate [11] can be manufactured by reducing the intermediate [10] in an inert solvent for the reaction in presence of a reducing agent. Then, the intermediate [4] can be manufactured by introducing a silyl protecting group (Si-Protecting group) to the intermediate [10] with a silyl protecting agent (Si-Protecting agent) in an inert solvent for the reaction in presence of a base.

8) Synthetic Pathway of Intermediate [6]

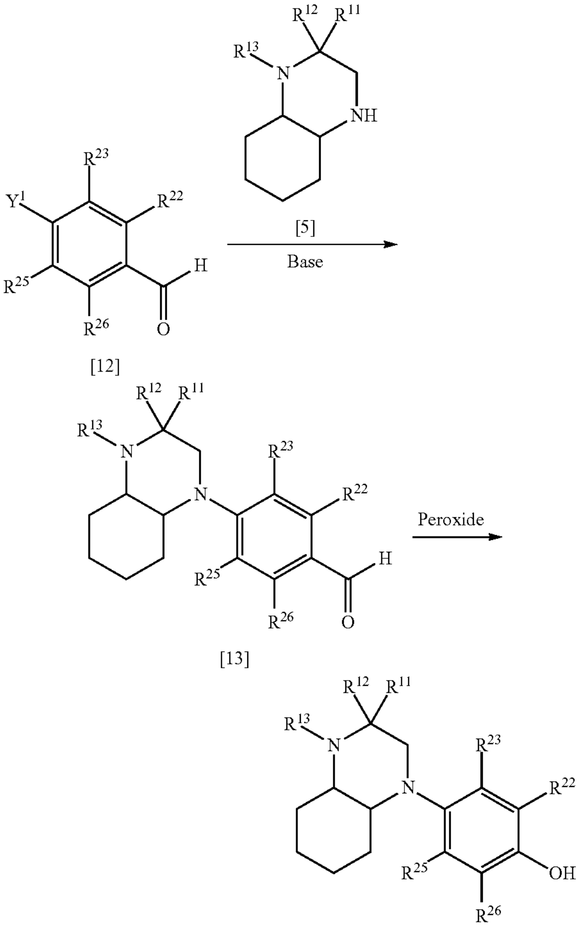

wherein $Y^1$ is a leaving group, and the other symbols are as defined above.

The intermediate [6] of the compound [1] of the present invention can be manufactured by the reaction indicated by the synthetic pathway described above. Specifically, first, the intermediate [13] can be manufactured by condensation reaction of the compound [12] and the compound [5] in an inert solvent for the reaction in presence of a base. Then, the intermediate [6] can be manufactured by reacting the compound [13] with a peroxide in an inert solvent for the reaction.

9) Synthetic Pathway of Intermediate [5]

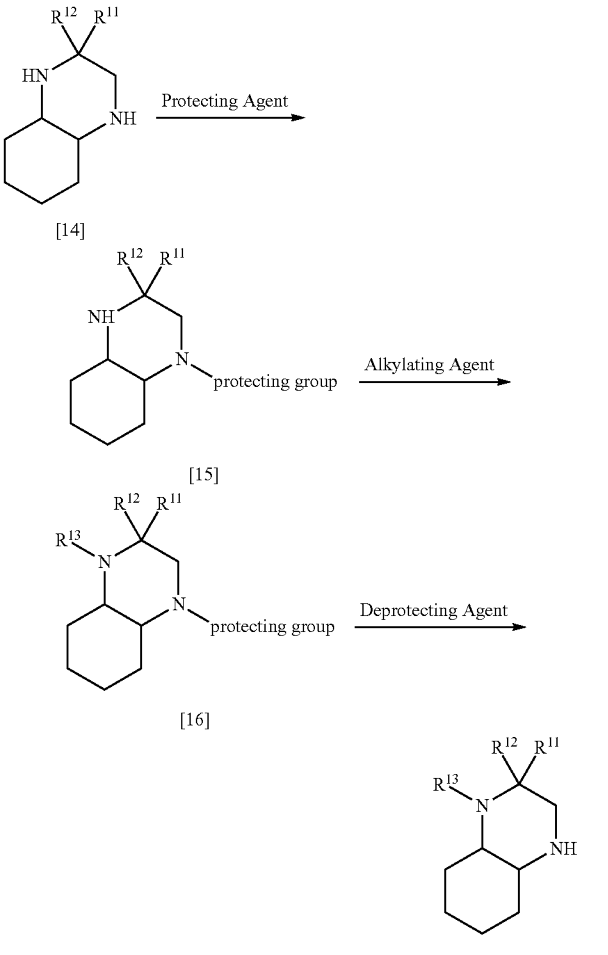

wherein symbols are as defined above.

The intermediate [5] of the compound [1] of the present invention can be manufactured by the reaction indicated by the synthetic pathway described above. Specifically, first, the intermediate [15] can be manufactured by introducing a protecting group to the intermediate [14] with a protecting agent in an inert solvent for the reaction. Next, the intermediate [16] can be manufactured by introducing an alkyl group to the intermediate [15] with an alkylating agent in an inert solvent for the reaction. Then, the intermediate [5] can be manufactured by deprotecting the protecting group of the intermediate [16] with a deprotecting agent.

Other reaction conditions (reaction temperature, reaction time, etc.) can be appropriately determined based on each known reaction.

In each reaction in the above-mentioned equation, the product can be used as a reaction solution or as a crude product thereof in the next reaction. However, the product can be isolated from the reaction mixture in accordance with a conventional method, or easily purified by usual separation means. Examples of the usual separation means include recrystallization, distillation, and chromatography.

The starting material compound, intermediate compound, and object compound in each above step, and the compound

[I] of the present invention include geometric isomers, stereoisomers, optical isomers, and tautomers. Various isomers can be separated by a general optical resolution method. They can also be manufactured by an appropriate optically active raw material compound.

The compound [I] of the present invention can be manufactured according to the synthetic methods indicated by the equations described above or methods analogous thereto.

When the specific method of producing the raw material compound used in the manufacturing the compound [I] of the present invention is not described, the raw material compound may be a commercially available product, or may be a product manufactured according to a method known per se or a method analogous thereto.

The starting material compound and object compound in each above step can be used in the form of an appropriate salt. Examples of the salt include those similar to the salts exemplified in the following as the salts of compound [I] of the present invention.

The compound [I] of the present invention includes salt forms thereof including the form of an acid addition salt, or a salt with a base may be formed depending on the kind of the substituent. Examples of the "acid" include an inorganic acid (e.g., hydrochloric acid, hydrobromic acid, nitric acid, sulfuric acid, phosphoric acid, etc.); an organic acid (e.g., methanesulfonic acid, p-toluenesulfonic acid, acetic acid, citric acid, tataric acid, maleic acid, fumaric acid, malic acid, lactic acid, etc.); and the like. Examples of the "base" include an inorganic base (e.g., sodium hydroxide, potassium hydroxide, calcium hydroxide, sodium carbonate, potassium carbonate, sodium hydrogen carbonate, potassium hydrogen carbonate, etc.); an organic base (e.g., methylamine, diethylamine, trimethylamine, triethylamine, ethanolamine, di-ethanolamine, triethanolamine, ethylenediamine, tris(hydroxymethyl)methylamine, di-cyclohexylamine, N,N'-dibenzylethylenediamine, guanidine, pyridine, picoline, choline, etc.); ammonium salts; and the like. In addition, a salt with amino acid such as lysine, arginine, aspartic acid, glutamic acid, and the like may be formed.

The present invention also encompasses various hydrates or solvates of the compound [I] and a salt thereof, and a crystal polymorphic substance of the same.

The compound [I] of the present invention includes a compound in which one or more atoms are substituted by one or more isotopes. Examples of the isotope include deuterium ($^{2}H$), tritium ($^{3}H$), $^{13}C$, $^{13}N$, $^{18}O$, and the like.

The compound [I] of the present invention also includes a pharmaceutically acceptable prodrug. Examples of the substituent that is modified to form a prodrug include reactive functional groups such as —OH, —COOH, amino, and the like. The modifying groups of these functional groups may be appropriately selected from the "substituents" in the present description.

The compound [I] of the present invention or a salt thereof may be a co-crystal or a co-crystal salt. The co-crystal or co-crystal salt as used herein means a crystalline material composed of two or more unique solids at room temperature, each of which has distinctive physical characteristics (e.g., structure, melting point, heats of fusion, etc.). A co-crystal and a co-crystal salt can be manufactured by applying a known co-crystallization method.

The salt of compound [I] of the present invention is preferably a pharmaceutically acceptable salt, and examples thereof include metal salts such as alkali metal salts (e.g., sodium salts, potassium salts, etc.), alkaline earth metal salts (e.g., calcium salts, magnesium salts, etc.), and the like; inorganic base salts such as ammonium salts, alkali metal carbonates (e.g., lithium carbonate, potassium carbonate, sodium carbonate, cesium carbonate, etc.), alkali metal hydrogen carbonates (e.g., lithium hydrogen carbonate, sodium hydrogen carbonate, potassium hydrogen carbonate, etc.), alkali metal hydroxides (e.g., lithium hydroxide, sodium hydroxide, potassium hydroxide, cesium hydroxide, etc.), and the like; organic base salts such as tri(lower) alkylamine (e.g., trimethylamine, triethylamine, N-ethyldiisopropylamine, etc.), pyridine, quinoline, piperidine, imidazole, picoline, dimethylaminopyridine, dimethylaniline, N-(lower)alkyl-morpholine (e.g., N-methylmorpholine, etc.), 1,5-diazabicyclo[4.3.0]non-5-ene (DBN), 1,8-diazabicyclo[5.4.0]undec-7-ene (DBU), 1,4-diazabicyclo[2.2.2]octane (DABCO), and the like; inorganic acid salts such as hy-drochlorides, hydrobromides, hydroiodides, sulfates, nitrates, phosphates, and the like; organic acid salts such as formates, acetates, propionates, oxalates, malonates, succinates, fumarates, maleates, lactates, malates, citrates, tartrates, carbonates, picrates, methanesulfonates, ethanesulfonates, p-toluenesulfonates, glutamates, and the like; and the like.

Each above general formula includes compounds in which solvates (e.g., hydrates, ethanolates, etc.) are added to the raw materials and the object compounds indicated in each reaction equation. Preferred solvates include hydrates.

Each object compound obtained in each above reaction equation can be isolated and purified from the reaction mixture by, for example, cooling the reaction mixture, separating the crude reaction product by isolation operations such as filtration, concentration, extraction, etc., and conducting normal purification operations such as column chromatography, recrystallization, etc.

The compound [I] of the present invention naturally includes isomers such as geometric isomers, stereoisomers, optical isomers, and the like.

Various isomers can be isolated by conventional methods by taking advantage of dif-ferences in physicochemical properties between isomers. For example, racemic compounds can be derived to sterically pure isomers by general optical resolution methods [for example, optical resolution methods by forming diastereomeric salts with common optically active acids (e.g., tartaric acid)]. The mixture of diastereomers can be separated by, for example, fractional crystallization or chromatography. Optically active compounds can also be produced by using suitable optically active raw materials.

The compound [I] of the present invention also encompasses isotopically labeled compounds that are identical to the compound [I] except that one or more atoms are replaced by one or more atoms having a specific atomic mass or mass number. Examples of isotopes that can be incorporated into the compound [I] of the present invention include isotopes of hydrogen, carbon, nitrogen, oxygen, sulfur, fluorine, and chlorine such as $^{2}H$, $^{3}H$, $^{13}C$, $^{14}C$, $^{15}N$, $^{18}O$, $^{17}O$, $^{18}F$, $^{36}Cl$, and the like. Certain isotope-labeled compounds [I] of the present invention containing the above isotopes and/or other isotopes of other atoms, for example, compounds containing radioisotopes of $^{3}H$, $^{14}C$, and the like, are useful in drug tissue distribution assays and/or substrate tissue distribution assays. The tritiated (i.e., $^{3}H$) and carbon-14 (i.e., $^{14}C$) isotopes are particularly preferred due to their ease of preparation and detectability. In addition, substitution by heavier isotopes such as deuterium (i.e., $^{2}H$) can be expected to bring certain therapeutic benefits due to improved metabolic stability, e.g., increased in vivo half-life or reduced dosage requirements. In general, the isotope-labeled compounds of the present invention can be prepared by replacing non-isotope-labeled reagents with readily available isotope-labeled reagents in the above reaction equations and/or methods disclosed in the following Examples.

The pharmaceutical composition containing the compound [I] of the present invention or a salt thereof as an active ingredient is described below.

The above pharmaceutical composition is a formulation of the compound [I] of the present invention or a salt thereof in the form of an ordinary pharmaceutical composition, which can be prepared by using commonly used carriers, diluents and/or excipients such as fillers, bulking agents, binders, humectants, disintegrants, surfactants, lubricants, and the like (hereinafter collectively referred to as a "pharmaceutically acceptable carrier").

Such pharmaceutical composition can be selected from a variety of forms depending on the therapeutic purpose, and typically includes tablets, pills, powders, liquids, suspensions, emulsions, granules, capsules, suppositories, injections (liquids, suspensions, etc.).

When forming tablets, known carriers can be widely used and examples thereof include excipients such as lactose, white sugar, sodium chloride, glucose, urea, starch, calcium carbonate, kaolin, crystalline cellulose, and the like; binders such as water, ethanol, propanol, simple syrup, glucose solution, starch solution, gelatin solution, car-boxymethyl-cellulose, shellac, methylcellulose, potassium phosphate, polyvinylpyrrolidone, and the like; disintegrants such as dry starch, sodium alginate, agar powder, laminaran powder, sodium hydrogen carbonate, calcium carbonate, polyoxyethylene sorbitan fatty acid esters, sodium lauryl sulfate, stearic acid mono-glyceride, starch, lactose, and the like; disintegration inhibitors such as white sugar, stearic acid, cacao butter, hydrogenated oil, and the like; absorption promoters such as quatemary ammonium base, sodium lauryl sulfate, and the like; humectants such as glycerin, starch, and the like; adsorbents such as starch, lactose, kaolin, bentonite, colloidal silicic acid, and the like; and lubricants such as purified talc, stearates, boric acid powders, polyethylene glycol, and the like.

Furthermore, tablets may be coated with conventional coating materials, if necessary; for example, sugar-coated tablets, gelatin-coated tablets, enteric coated tablets, film-coated tablets, double-layered tablets and multilayered tablets can be prepared.

When forming pills, known carriers can be widely used and examples thereof include excipients such as glucose, lactose, starch, cocoa butter, hydrogenated vegetable oil, kaolin, talc, and the like; binders such as gum arabic powder, tragacanth powder, gelatin, ethanol, and the like; and disintegrants such as laminaran, agar, and the like.

When preparing suppositories, known carriers can be widely used and examples thereof include polyethylene glycol, cocoa butter, a higher alcohol, an ester of a higher alcohol, gelatin, a semisynthetic glyceride, and the like.

When preparing injections, a liquid, an emulsion and a suspension are sterilized and preferably they are isotonic fluids with blood. When preparing these dosage forms, known diluents can be widely used and examples thereof include water, ethanol, propylene glycol, ethoxylated isostearyl alcohol, polyoxylated isostearyl alcohol and polyoxyethylene sorbitan fatty acid ester, and the like. In this case, a sufficient amount of salt, glucose or glycerin to prepare an isotonic solution may be added to a pharmaceutical preparation. Further, to the preparation may be added common solubilizer, buffer, soothing agent, and the like, and if necessary, coloring agent, preservative, fragrance, flavoring agent, sweetening agent and the like, and/or other pharmaceutical products.

The amount of the compound [I] of the present invention or a salt thereof contained in a pharmaceutical composition is not particularly limited and can be selected from a wide range. However, it is usually preferable to include from 1 to 70% by weight of the compound [I] or a salt thereof in a pharmaceutical composition.

Methods for administering the pharmaceutical composition in the present invention are not particularly limited and are appropriately determined depending upon e.g., the dosage form; the age and sex of the subject or patient (particularly human), the disease state, and the other conditions. For example, tablets, pills, liquids, suspensions, emulsions, granules, and capsules are orally administered. Injections are intravenously administered singly or in combination with a general complemental liquid such as glucose and amino acids, and further, if necessary, injections are intramuscularly, in-tradermally, subcutaneously or intraperitoneally administered singly. Suppositories are intra-rectally administered.

The dosage of the above pharmaceutical composition may be suitably selected according to the method of use, the age and sex of the subject or patient (particularly human), the disease state, and the other conditions, and is typically about 0.001 to about 100 mg/kg body weight/day, preferably 0.001 to 50 mg/kg body weight/day, in single or divided doses.

Since the above dosage varies depending on various conditions, a dosage lower than the above range may be sufficient, or a dosage higher than the above range may be necessary.

The compound [I] of the present invention or a salt thereof has reuptake inhibitory activity against one, two or three types of monoamine (serotonin, norepinephrine, and dopamine).

Compared to existing compounds with monoamine reuptake inhibitory activity, the compound [I] of the present invention or a salt thereof has significantly stronger uptake inhibitory activity for any one, any two, or all of the three monoamines in vitro tests. Further, in intracerebral microdialysis (in vivo), the compound of the present invention or a salt thereof shows significantly stronger activity against the increase of any one, any two, or all of the three monoamines compared to existing compounds with monoamine reuptake inhibitory activity.

The inhibitory activity ($IC_{50}$) of the compound [I] of the present invention or a salt thereof against serotonin is not more than 100 nM, preferably not more than 30 nM.

The inhibitory activity ($IC_{50}$) of the compound [I] of the present invention or a salt thereof against norepinephrine is not more than 100 nM, preferably not more than 30 nM.

The inhibitory activity ($IC_{50}$) of the compound [I] of the present invention or a salt thereof against dopamine is not more than 300 nM, preferably not more than 150 nM. It is preferable that the inhibitory activity ($IC_{50}$) against dopamine tends to be weaker than that against norepinephrine.

The human hepatic intrinsic clearance of the compound [I] of the present invention or a salt thereof is not more than 100 μL/min/mg, preferably not more than 50 μL/min/mg.

The human serum protein binding rate of the compound [I] of the present invention or a salt thereof is not more than 80%, preferably not more than 70%, more preferably not more than 50%.

The inhibition rate of metabolic enzymes in the liver of the compound [I] of the present invention or a salt thereof is less than 50%, or an $IC_{50}$ value of not less than 100 μM at 10 μM for CYP2C9; less than 50%, or an $IC_{50}$ value of not less than 50 μM at 10 μM for CYP2D6; and less than 50%, or an $IC_{50}$ value of not less than 50 μM at 10 μM for CYP3A4.

The ratio of inhibitory activity ($IC_{50}$) of the compound [I] of the present invention or a salt thereof against serotonin, norepinephrine and dopamine is 1-20:1-2:1-100, preferably 1-5:1-2:1-50, more preferably 1-5:1:5-25.

The compound [I] of the present invention or a salt thereof has a low binding rate to plasma proteins. If a drug binds to plasma proteins, the drug cannot exert its effect. Therefore, if the binding rate of a drug to plasma proteins is low, the drug can be expected to be effective at low doses. In other words, the effect of can be expected at lower blood concentrations.

The compound [I] of the present invention or a salt thereof has weak inhibitory activity against metabolic enzymes in the liver, specifically against cytochrome P450 (CYP) such as CYP2C9, CYP2D6, and CYP3A4. Therefore, even if the compound [I] or a salt thereof is taken in combination with other drugs, it has less effect on the metabolism of the drugs.

The compound [I] of the present invention or a salt thereof has a broader therapeutic spectrum compared with known therapeutic drugs for ADHD.

The compound [I] of the present invention or a salt thereof expresses sufficient therapeutic effect even after a short period of administration.

The compound [I] of the present invention or a salt thereof has an excellent brain migration property.

The compound [I] of the present invention or a salt thereof expresses an excellent improvement effect on spontaneous locomotor activity in stroke-prone spontaneously hypertensive rats (SHRSP), which is used for screening of therapeutic drugs for ADHD. In addition, the compound [I] or a salt thereof expresses an excellent improvement effect on the impulsivity-like symptom of SHRSP.

The compound [I] of the present invention or a salt thereof exhibits strong activity in the marble-burying test, which is used as a model of anxiety and obsessive-compulsive disorder.

The compound [I] of the present invention or a salt thereof has reuptake inhibitory activity against one, two or three types of monoamine (serotonin, norepinephrine, and dopamine), and is therefore effective for the treatment of various disorders related to serotonin, norepinephrine and/or dopamine nerve dysfunction.

Examples of such disorder include attention-deficit hyperactivity disorder (ADHD), Tourette's disorder (also called Tourette's syndrome), autism spectrum disorder, Asperger's syndrome, depression (e.g., major depressive disorder; bipolar I disorder; bipolar II disorder; mixed bipolar disorder; dysthymic disorder; rapid cycler; atypical depression; seasonal affective disorder; postpartum depression; mild depression; recurrent brief depressive disorder refractory depression-chronic depression; treatment-resistant depression (also called double depression); alcohol-induced mood disorder; mixed anxiety-depressive disorder; depressions associated with various disorders such as Cushing's syndrome, hypothyroidism, hyperparathyroidism, Addison's disease, amenorrhea-galactorrhea syndrome, Parkinson's disease, Alzheimer's disease, cerebrovascular dementia, cerebral infarction, cerebral hemorrhage, subarachnoid hemorrhage, diabetes, viral infection, multiple sclerosis, chronic fatigue syndrome, coronary artery disease, pain, and cancer; middle-age depression; elderly depression; childhood and adolescent depression; depression induced by a drug such as interferon; depressive symptoms in adjustment disorder; anxiety in adjustment disorder, anxiety associated with various disorders [e.g., neurological disorders (head trauma, brain infection and inner ear disorder); cardiovascular disorders (heart failure, arrhythmia); endocrine disorder (hyperepinephry, hyperthyroidism); respiratory disorders (asthma, chronic obstructive pulmonary disease)], generalized anxiety disorder, phobias (e.g., agoraphobia, social phobia and simple phobia), obsessive-compulsive disorder, panic disorder, post-traumatic stress disorder, acute stress disorder, hypochondriac, dissociative amnesia, avoidant personality disorder, body dysmorphic disorder, eating disorder (e.g., bulimia disorder, bulimia nervosa, anorexia nervosa and neuronecrosis anorexia), obesity, chemical dependence (e.g., addictions to alcohol, cocaine, heroin, phenobarbital, nicotine and benzodi-azepines), pain (e.g., chronic pain, psychogenic pain, neuropathic pain, phantom pain, postherpetic neuralgia, traumatic neck syndrome, spinal cord injury pain, trigeminal neuralgia and diabetic neuropathy), fibromyalgia, apathy, Alzheimer's disease (e.g., dementia, cognitive disorders, and behavioral disorders, etc. caused by Alzheimer's disease), memory impairment (e.g., dementia, amnesia and age-related cognitive decline (ARCD)), Parkinson's disease (e.g., dementia in Parkinson's disease, neu-roleptic malignant syndrome in Parkinson's disease and tardive dyskinesia), restless leg syndrome, endocrine disorder (e.g., hyperprolactinemia), hypertension, vasospasm (particularly in cerebrovascular system), cerebellar ataxia, gastrointestinal tract disorder (including changes in movement and secretion), negative symptoms in schizophrenia, affective disorders in schizophrenia, cognitive dysfunction in schizophrenia, premenstrual syndrome, stress urinary incontinence, urge urinary incontinence, impulse control disorders, trichotillomania, kleptomania, gambling addiction, cluster headache, migraine, chronic paroxysmal hemicrania, chronic fatigue, premature ejaculation, male impotence, narcolepsy, primary hypersomnia, atonic seizure, sleep apnea syndrome and headache (related to vascular disorders), and the like.

Disclosures of all PTLs and NPLs cited in the present description are incorporated in the present description in their entirety by reference.

EXAMPLES

The present invention is explained in detail in the following by referring to Test Examples, Reference Examples, and Examples, which are not to be construed as limitative, and the invention may be changed within the scope of the present invention. In the present description, the following abbreviations may be used.

| Abbreviations | Words |
|---|---|
| REX | reference example number |
| EX | example number |
| STR | structural formula (in the formula, "Abs" represents the absolute configuration of the compound) |
| RProp | Manufacturing method (numbers indicate that the compound was manufactured using the corresponding raw materials in the same way as the reference example compound having that number as a reference example number) |

-continued

| Abbreviations | Words |
|---|---|
| Prop | Manufacturing method (numbers indicate that the compound was manufactured using the corresponding raw materials in the same way as the example compound having that number as an example number) |
| Data | Physical property data (NMR1: δ (ppm) in $^1$H-NMR in DMSO-$d_6$; NMR2: δ (ppm) in $^1$H-NMR in $CDCl_3$); MS: Mass spectrum) |
| 9-BBN | 9-borabicyclo[3.3.1]nonane |
| AcOEt | ethyl acetate |
| AcOH | acetic acid |
| AcOK | potassium acetate |
| AcONa | sodium acetate |
| $BBr_3$ | boron tribromide |
| $Boc_2O$ | di-t-butyl dicarbonate |
| n-BuLi | n-butyllithium |
| t-BuONa | Sodium tert-Butoxide |
| $tBu_3P•HBF_4$ | tri-tert-butylphosphonium tetrafluoroborate |
| CDI | 1,1'-carbonyldiimidazole |
| $Cs_2CO_3$ | cesium carbonate |
| DBU | 1,8-diazabicyclo[5.4.0]-7-undecene |
| DCC | dicyclohexylcarbodiimide |
| DCE | 1,2-dichloroethane |
| DCM | dichloromethane |
| DEAD | diethylazodicarboxylate |
| DHP | 3,4-dihydro-2H-pyran |
| DIBAL | diisobutylaluminum hydride |
| DIPEA | diisopropylethylamine |
| DMA | N,N-DIMETHYLACETAMIDE |
| DMAP | 4-(dimethylamino)pyridine |
| DME | dimethoxyethane |
| DMF | N,N-dimethylformamide |
| DMSO | dimethyl sulfoxide |
| DPPA | diphenylphosphoryl azide |
| $Et_2O$ | diethyl ether |
| EtOH | ethanol |
| HCl | hydrochloric acid |
| Hexane | n-hexane |
| HOBt | 1-hydroxybenzotriazole |
| IPA | 2-propanol |
| IPE | diisopropyl ether |
| $K_2CO_3$ | potassium carbonate |
| $K_3PO_4$ | tripotassium phosphate |
| KOH | potassium hydroxide |
| LAH | lithium aluminum hydride |
| $LiBH_4$ | lithium borohydride |
| MCPBA | m-chloroperoxybenzoic acid |
| MeCN | acetonitrile |
| MEK | 2-butanone |
| MeOH | methanol |
| $MgSO_4$ | magnesium sulfate |
| $NaBH_4$ | sodium borohydride |
| $NaBH(OAc)_3$ | sodium triacetate borohydride |
| $Na_2CO_3$ | sodium carbonate |
| NaH | sodium hydride |
| $NaHCO_3$ | sodium hydrogen carbonate |
| $NaHSO_4$ | sodium hydrogen sulfate |
| NaOH | sodium hydroxide |
| NaOtBu | sodium t-butoxide |
| $Na_2SO_4$ | sodium sulfate |
| NMP | N-methylpyrrolidone |
| $Pd_2(dba)_3$ | tris(dibenzylideneacetone)dipalladium(0) |
| $Pd(dppf)Cl_2•CH_2Cl_2$ | [1,1'-bis(diphenylphosphino)ferrocene]palladium(II) dichloride dichloromethane adduct |
| $Pd(OAc)_2$ | Palladium(II) Acetate |
| $Pd(PPh_3)_4$ | tetrakis(triphenylphosphine)palladium(0) |
| Pd/C | palladium-carrying carbon |
| PPTS | pyridinium p-toluenesulfonate |
| TBAF | tetra-n-butylammonium fluoride |
| TEA | triethylamine |
| TFA | trifluoroacetic acid |

-continued

| Abbreviations | Words |
|---|---|
| THF | tetrahydrofuran |
| TIPSCl | triisopropylsilyl chloride |
| TPP | triphenylphosphine |
| WSC | 3-ethyl-1-(3-dimethylaminopropyl)carbodiimide |

In the following Examples, "room temperature" generally means about 10° C. to about 35° C. The ratios indicated for mixed solvents are volume mixing ratios, unless otherwise specified. % means wt %, unless otherwise specified.

$^1$HNMR (proton nuclear magnetic resonance spectrum) was measured by Fourier-transform type NMR (either of Bruker AVANCE III 400 (400 MHz) and Bruker AVANCE III HD (500 MHz)).

Mass spectrum (MS) was measured by LC/MS (ACQUITY UPLC H-Class). As ionization method, ESI method was used. The data indicates actual measured value (found). Generally, molecular ion peaks ([M+H]+, [M−H]−, etc.) are observed. In the case of a salt, a molecular ion peak or fragment ion peak of free form is generally observed.

In silica gel column chromatography, when denoted as basic, aminopropylsilane-bonded silica gel was used.

The absolute configuration of the compound was determined by known X-ray crystal structure analysis method (e.g., "Basic Course for Chemists 12, X-ray Crystal Structure Analysis" written by Shigeru Ohba and Shigenobu Yano, 1st edition, 1999) or estimated from the empirical rule of Shi asymmetric epoxidation (Waldemar Adam, Rainer T. Fell, Chantu R. Saha-Moller and Cong-Gui Zhao: Tetrahedron: Asymmetry 1998, 9, 397-401; Yuanming Zhu, Yong Tu, Hongwu Yu, Yian Shi: Tetrahedron Lett. 1988, 29, 2437-2440).

Reference Examples

Reference Example 1. Synthesis of (2-(4-bromo-2,6-difluorophenoxy)ethoxy)(tert-butyl)dimethylsilane To a solution of 4-bromo-2,6-difluorophenol (22.93 g) and (2-bromoethoxy)-tert-butyldimethylsilane (25.0 g) in DMF (120 mL) was added $K_2CO_3$ (28.9 g, fine powder), and the mixture was stirred at 70° C. for 3 hours. The reaction mixture was cooled to room temperature, thereto was added ice water, and the mixture was extracted with AcOEt. The organic layer was concentrated, and the residue was then purified by silica gel column chromatography (Hexane/AcOEt) to obtain the object compound (35.0 g).

Reference Example 2. Synthesis of (4a'S,8a'S)-4'-(4-(2-((ten-butyldimethylsilyl)oxy)ethoxy)-3,5-difluorophenyl)octahydro-1'H-spiro[cyclobutane-1,2'-quinoxaline To a solution of (4a'S,8a'S)-octahydro-1'H-spiro[cyclobutane-1,2'-quinoxaline] (300 mg) and (2-(4-bromo-2,6-difluorophenoxy)ethoxy)(tert-butyl)dimethylsilane (672 mg) in toluene (6 mL) were added $Pd(OAc)_2$ (29.9 mg), $tBu_3P·HBF_4$ (38.6 mg) and t-BuONa (240 mg), and the mixture was stirred under nitrogen atmosphere at 90° C. for 1 hour. The reaction mixture was filtered through celite, and the filtrate was concentrated. The residue was purified by basic silica gel chromatography (Hexane/AcOEt) to obtain the object compound (490 mg).

Reference Example 3. Synthesis of ethyl 2-(4-bromophenoxy)-2,2-difluoroacetate

To a solution of p-bromophenol (5 g) and DBU (5.23 mL) in DMF (25 mL) was added ethyl bromodifluoroacetate (4.08 mL), and the mixture was stirred at room temperature overnight. To the reaction mixture was added ice water, and the mixture was extracted with AcOEt. The organic layer was concentrated, and the residue was then purified by silica gel column chromatography (Hexane/AcOEt) to obtain the object compound (7.2 g).

Reference Example 4. Synthesis of 2-(4-bromophenoxy)-2,2-difluoroethan-1-ol

To a solution of ethyl 2-(4-bromophenoxy)-2,2-difluoroacetate (13.9 g) in THF (150 mL) was added $LiBH_4$ (2.26 g) with stirring under ice-cooling, and the mixture was stirred at room temperature overnight. After cooling the reaction mixture, thereto was added saturated $NaHSO_4$ aq., and the mixture was extracted with AcOEt. The organic layer was concentrated, and the residue was then purified by silica gel column chromatography (Hexane/AcOEt) to obtain the object compound (10.4 g).

Reference Example 5. Synthesis of (2-(4-bromophenoxy)-2,2-difluoroethoxy)triisopropylsilane To a solution of 2-(4-bromophenoxy)-2,2-difluoroethan-1-ol (3.00 g) and imidazole (1.21 g) in DMF (15 mL) was added TIPSCl (2.76 mL) with stirring at room temperature, and the mixture was stirred overnight. To the reaction mixture was added ice water, and the mixture was extracted with AcOEt. The organic layer was concentrated, and the residue was then purified by silica gel column chromatography (Hexane/AcOEt) to obtain the object compound (4.8 g).

Reference Example 6. Synthesis of (4a'S,8a'S)-4'-(4-(1,1-difluoro-2-((triisopropylsilyl)oxy)ethoxy)phenyl)octahydro-1'H-spiro[cyclobutane-1,2'-quinoxaline To a solution of (4a'S,8a'S)-octahydro-1'H-spiro[cyclobutane-1,2'-quinoxaline] (300 mg) and (2-(4-bromophenoxy)-2,2-difluoroethoxy)triisopropylsilane (749 mg) in toluene (6 mL) were added $Pd(OAc)_2$ (29.9 mg), $tBu_3P{\cdot}HBF_4$ (38.6 mg) and t-BuONa (192 mg), and the mixture was stirred under nitrogen atmosphere at 90° C. for 1 hour. The reaction mixture was filtered through celite, and the filtrate was concentrated. The residue was purified by basic silica gel column chromatography (Hexane/AcOEt) to obtain the object compound (680 mg).

Reference Example 41. Synthesis of (3R,4aS,8aS)-1-(3-chloro-4-(2-((triisopropylsilyl)oxy)ethoxy)phenyl)-3-methyldecahy droquinoxaline To a solution of (2R,4aS,8aS)-2-methyldecahydroquinoxaline (500 mg) and (2-(4-bromo-2-chlorophenoxy)ethoxy)triisopropylsilane (1322 mg) in toluene (5 mL) were added $Pd(OAc)_2$ (58.2 mg), $tBu_3P{\cdot}HBF_4$ (75 mg) and t-BuONa (467 mg), and the mixture was stirred under nitrogen atmosphere at 90° C. for 1 hour. The reaction mixture was filtered through celite, and the filtrate was concentrated. The residue was purified by basic silica gel column chromatography (Hexane/AcOEt) to obtain the object compound (700 mg).

Reference Example 65. Synthesis of tert-butyl (4aS,8aS)-3,3-dimethyloctahydroquinoxaline-1(2H)-carboxylate To a solution of (4aS,8aS)-2,2-dimethyldecahydroquinoxaline (7.35 g) in MeOH (70 mL) was added $Boc_2O$ (9.65 g) with stirring under ice-cooling, and the mixture was stirred at room temperature overnight. The reaction mixture was concentrated, and the residue was then purified by basic silica gel column chromatography (Hexane/AcOEt) to obtain the object compound (11.0 g).

Reference Example 66. Synthesis of tert-butyl (4aS,8aS)-3,3,4-trimethyloctahydroquinoxaline-1(2H)-carboxylate To a solution of tert-butyl (4aS,8aS)-3,3-dimethyloctahydroquinoxaline-1(2H)-carboxylate (10.0 g) in DCE (100 mL) and THF (50 mL) was added 37% formaldehyde solution (9.14 mL), and the mixture was stirred at room temperature for 30 minutes. After that, to the mixture was added $NaBH(OAc)_3$ (23.9 g) with stirring under ice-cooling. The mixture was stirred at room temperature overnight, concentrated under reduced pressure, and extracted with DCM. The organic layer was concentrated, and the residue was then purified by basic silica gel column chromatography to obtain the object compound (11.0 g).

Reference Example 67. Synthesis of (4aS,8aS)-1,2,2-trimethyldecahydroquinoxaline To a solution of tert-butyl (4aS,8aS)-3,3,4-trimethyloctahydroquinoxaline-1(2H)-carboxylate (10 g) in DCM (40 mL) was added TFA (20 mL) with stirring under ice-cooling, and the mixture was stirred at room temperature overnight. The reaction mixture was concentrated, thereto was added saturated $K_2CO_3$ aq., and the mixture was extracted with AcOEt. The organic layer was concentrated, and the residue was then purified by basic silica gel column chromatography (Hexane/AcOEt) to obtain the object compound (4.68 g).

Reference Example 68. Synthesis of (4aS,8aS)-4-(4-(1,1-difluoro-2-((triisopropylsilyl)oxy)ethoxyphenyl)-1,2,2-trimethyld ecaydroquinoxaline To a solution of (4aS,8aS)-1,2,2-trimethyldecahydroquinoxaline (200 mg) and (2-(4-bromophenoxy)-2,2-difluoroethoxy)triisopropylsilane (494 mg) in toluene (5 mL) were added $Pd(OAc)_2$ (19.70 mg), $tBu_3P{\cdot}HBF_4$ (25.5 mg) and t-BuONa (127 mg), and the mixture was stirred under nitrogen atmosphere at 90° C. for 1 hour. The reaction mixture was filtered through celite, and the filtrate was concentrated. The residue was purified by basic silica gel column chromatography (Hexane/AcOEt) to obtain the object compound (480 mg).

Reference Example 82. Synthesis of (4aR,8aS)-1-(3-chloro-4-(2-((triisoproylsilyl)oxy)ethoxy)phenyl)-3,3-dimethyldecahy droquinoxaline To a solution of (4aS,8aR)-2,2-dimethyldecahydroquinoxaline (250 mg) and (2-(4-bromo-2-chlorophenoxy)ethoxy)triisopropylsilane (697 mg) in toluene (5 mL) were added $Pd(OAc)_2$ (26.7 mg), $tBu_3P{\cdot}HBF_4$ (34.5 mg) and t-BuONa (157 mg), and the mixture was stirred under nitrogen atmosphere at 90° C. for 1 hour. The reaction mixture was filtered through celite, and the filtrate was concentrated. The residue was purified by basic silica gel column chromatography (Hexane/AcOEt) to obtain the object compound (400 mg).

Reference Example 85. Synthesis of (4aS,8aR)-4-(3-chloro-4-(2-((triisopropylsilyl)oxy)ethoxy)phenyl)-1,2,2-trimethyldeca hydroquinoxaline To a solution of (4aR,8aS)-1-(3-chloro-4-(2-((triisopropylsilyll)oxy)ethoxy)phenyl)-3,3-dimethyldecah ydroquinoxaline (180 mg) in DCM/THF (1:1) (4 mL) was added 36% formaldehyde aq. (83 μL), and the mixture was stirred at room temperature for 30 minutes. After that, to the mixture was added $NaBH(OAc)_3$ (231 mg), and the mixture was stirred at room temperature for two days. The solvent was concentrated, and the residue was then purified by column chromatography (AcOEt/MeOH) to obtain the object compound (170 mg).

Reference Example 110. Synthesis of 2-chloro-4-((4aR,8aS)-3,3-dimethyloctahydroquinoxalin-1(2H)-yl-5-fluorobenzaldehyde To a solution of (4aS,8aR)-2,2-dimethyldecahydroquinoxaline (343 mg) and 2-chloro-4,5-difluorobenzaldehyde (300 mg) in DMSO (3 mL) was added DIPEA (445 μL), and the mixture was stirred under nitrogen atmosphere at 100° C. for 7 hours. The reaction mixture was cooled to room temperature, thereto was added 5N NaOH aq., and the mixture was extracted with AcOEt. The organic layer was concentrated, and the residue was then purified by silica gel column chromatography (AcOEt/MeOH) to obtain the object compound (490 mg).

Reference Example 111. Synthesis of 2-chloro-4-((4aR,8aS)-3,3-dimethyloctahydroquinoxalin-1(2H)-yl)-5-fluorophenol To a solution of 2-chloro-4-((4aR,8aS)-3,3-dimethyloctahydroquinoxalin-1(2H)-yl)-5-fluorobenzaldehy de (480 mg) in MeOH (8 mL) were added 35% hydrogen peroxide aq. (323 μL) and $H_2SO_4$ (118 μL), and the mixture was stirred at room temperature for 3 days. To the reaction mixture was added saturated $NaHCO_3$ aq., and the precipitated solid was filtered out. The resulting product was washed with water and hexane to obtain the object compound (400 mg).

Reference Example 112. Synthesis of (4aR,8aS)-1-(4-(2-((tert-butyldimethylsilyl)oxy)ethoxy)-5-chloro-2-fluorophenyl)-3,3-dimethyldecahydroquinoxaline To a suspension of 2-chloro-4-((4aR,8aS)-3,3-dimethyloctahydroquinoxalin-1(2H)-yl)-5-fluorophenol (150 mg) and $K_2CO_3$ (133 mg, finely milled) in DMF (3 mL) was added (2-bromoethoxy)-tert-butyldimethylsilane (129 μL), and the mixture was stirred at 60° C. for 3 hours. Into the reaction mixture was poured water, and the mixture was extracted with AcOEt. The organic layer was concentrated, and the residue was then purified by basic silica gel column chromatography (Hexane/AcOEt) to obtain the object compound (210 mg).

Reference Example 118. Synthesis of ethyl 2-(4-((4aR,8aS)-3,3-dimethyloctahydroquinoxalin-1(2H)-yl)-3-fluorophenoxy)-2,2-difluoroacetate To a solution of 4-((4aR,8aS)-3,3-dimethyloctahydroquinoxalin-1(2H)-yl)-3-fluorophenol (150 mg) in DMF (3 mL) was added DBU (244 μL), followed by ethyl bromodifluoroacetate (138 μL), and the mixture was stirred at 60° C. for 3 hours. Into the reaction mixture was poured water, and the mixture was extracted with AcOEt. The organic layer was concentrated, and the residue was then purified by silica gel column chromatography (Hexane/AcOEt) to obtain the object compound (175 mg).

The compounds of Reference Examples 7-40, 42-64, 69-81, 83-84, 86-109, 113-117 and 119-165 were manufactured in the same manner as in Reference Examples 1-6, 41, 65-68, 82, 85, 110-112 and 118. Structural formulae and physicochemical data of the compounds of Reference Examples 1 to 165 are shown in Tables 1-1 to 1-22.

TABLE 1-1

| REX | STR | RProp | DATA |
|---|---|---|---|
| 1 | 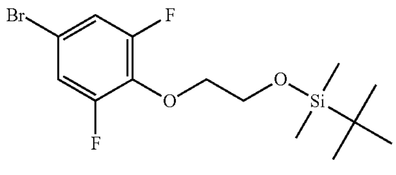 | 1 | NMR2: 0.06 (6H, s), 0.87 (9H, s), 3.88-3.95 (2H, m), 4.15-4.23 (2H, m), 7.00-7.12 (2H, m). |
| 2 | 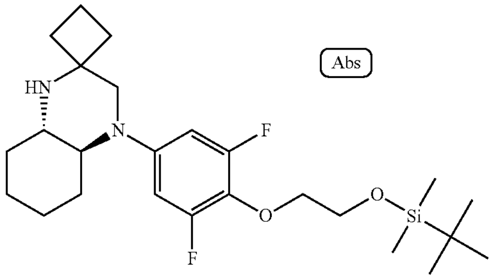 | 2 | NMR2: 0.07 (6H, s), 0.77-1.06 (10H, m), 1.13-1.98 (13H, m), 2.20-2.33 (1H, m), 2.38-2.47 (1H, m), 2.49-2.58 (1H, m), 2.59-2.68 (1H, m), 3.04 (1H, d, J = 11.0 Hz), 3.92 (2H, t, J = 5.1 Hz), 4.15 (2H, t, J = 5.1 Hz), 6.61-6.73 (2H, m). |

TABLE 1-1-continued
| REX | STR | RProp | DATA |
|---|---|---|---|
| 3 | 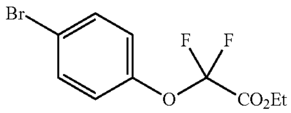 | 3 | NMR2: 1.38 (3H, t, J = 7.2 Hz), 4.39 (2H, q, J = 7.1 Hz), 7.07-7.15 (2H, m), 7.45-7.53 (2H, m). |
| 4 | 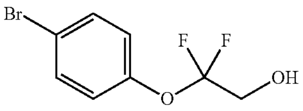 | 4 | NMR2: 2.07-2.19 (1H, m), 3.94-4.05 (2H, m), 7.05-7.13 (2H, m), 7.43-7.51 (2H, m). |
| 5 | 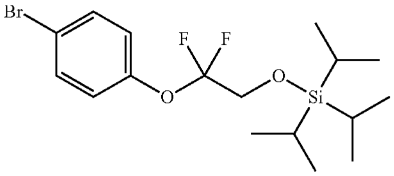 | 5 | NMR2: 1.04-1.22 (21H, m), 4.08 (2H, t, J = 8.9 Hz), 7.04-7.12 (2H, m), 7.41-7.49 (2H, m). |
| 6 | 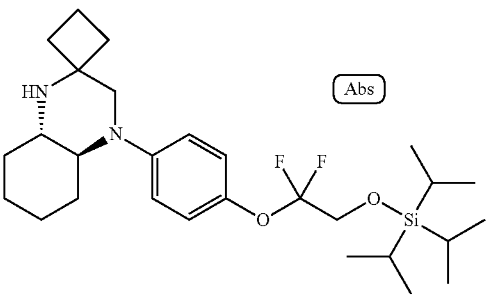 | 6 | NMR2: 0.84-1.03 (1H, m), 1.03-1.45 (24H, m), 1.57-1.92 (10H, m), 2.31-2.41 (1H, m), 2.43-2.53 (1H, m), 2.53-2.63 (1H, m), 2.67-2.74 (1H, m), 3.07 (1H, d, J = 11.1 Hz), 4.08 (2H, t, J = 8.8 Hz), 7.04-7.17 (4H, m). |
| 7 | 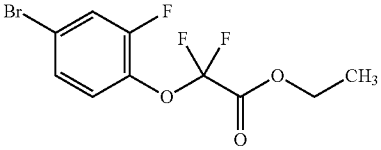 | 3 | NMR2: 1.40 (3H, t, J = 7.2 Hz), 4.42 (2H, q, J = 7.2 Hz), 7.17-7.24 (1H, m), 7.26-7.31 (1H, m), 7.34-7.39 (1H, m). |
| 8 | 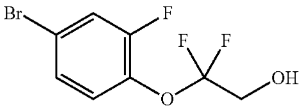 | 4 | NMR2: 2.13 (1H, t, J = 7.5 Hz), 4.00-4.09 (2H, m), 7.17-7.25 (1H, m), 7.25-7.30 (1H, m), 7.32-7.37 (1H, m). |
| 9 | 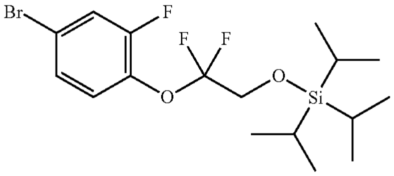 | 5 | NMR2: 1.04-1.21 (21H, m), 4.14 (2H, t, J = 9.1 Hz), 7.16-7.27 (2H, m), 7.32 (1H, dd, J = 2.2, 9.4 Hz). |

TABLE 1-2
| REX | STR | RProp | DATA |
|---|---|---|---|
| 10 | 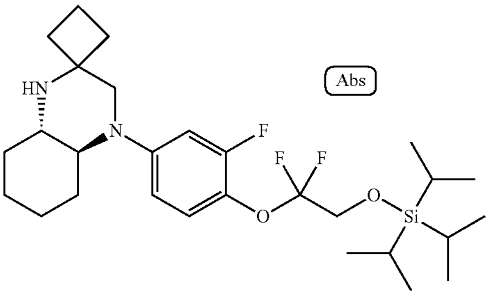 | 6 | NMR2: 0.84-1.03 (1H, m), 1.04-1.47 (24H, m), 1.49-1.92 (10H, m), 2.27-2.37 (1H, m), 2.40-2.50 (1H, m), 2.51-2.62 (1H, m), 2.64-2.72 (1H, m), 3.09 (1H, d, J = 11.1 Hz), 4.14 (2H, t, J = 9.1 Hz), 6.83-6.88 (1H, m), 6.91 (1H, dd, J = 2.5, 11.6 Hz), 7.17-7.25 (1H, m). |
| 11 | 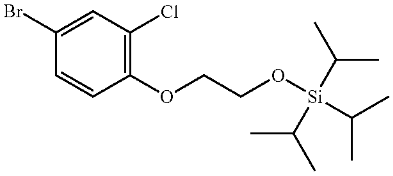 | 1 | NMR2: 1.03-1.19 (21H, m), 4.04-4.15 (4H, m), 6.87 (1H, d, J = 8.8 Hz), 7.29 (1H, dd, J = 2.4, 8.8 Hz), 7.48 (1H, d, J = 2.4 Hz). |
| 12 | 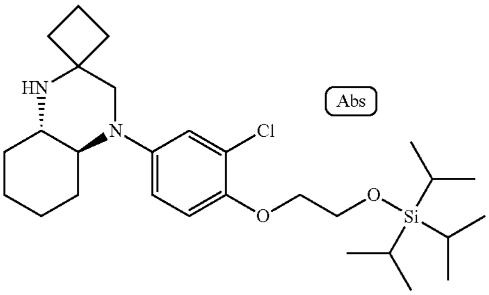 | 2 | NMR2: 0.85-1.01 (1H, m), 1.02-1.46 (24H, m), 1.49-1.91 (10H, m), 2.24-2.34 (1H, m), 2.40-2.59 (2H, m), 2.68 (1H, dd, J = 1.5, 11.0 Hz), 3.02 (1H, d, J = 11.0 Hz), 4.03-4.15 (4H, m), 6.91 (1H, d, J = 8.7 Hz), 6.97 (1H, dd, J = 2.5, 8.7 Hz), 7.15 (1H, d, J = 2.5 Hz). |
| 13 | 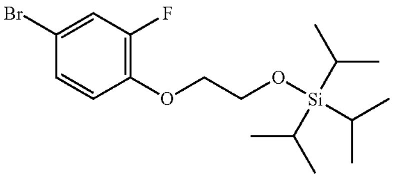 | 1 | NMR2: 1.01-1.21 (21H, m), 4.03-4.09 (2H, m), 4.09-4.15 (2H, m), 6.90 (1H, t, J = 8.7 Hz), 7.16 (1H, ddd, J = 1.6, 2.4, 8.7 Hz), 7.22 (1H, dd, J = 2.4, 10.5 Hz). |
| 14 | 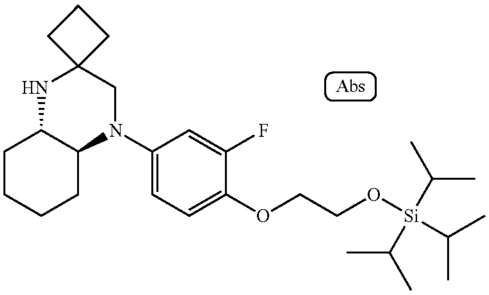 | 2 | NMR2: 0.84-1.02 (1H, m), 1.02-1.44 (24H, m), 1.50-1.91 (10H, m), 2.23-2.33 (1H, m), 2.40-2.60 (2H, m), 2.67 (1H, dd, J = 1.5, 11.0 Hz), 3.03 (1H, d, J = 11.1 Hz), 4.01-4.08 (2H, m), 4.08-4.17 (2H, m), 6.79-6.85 (1H, m), 6.88 (1H, dd, J = 2.5, 12.7 Hz), 6.93 (1H, t, J = 9.0 Hz). |
| 15 | 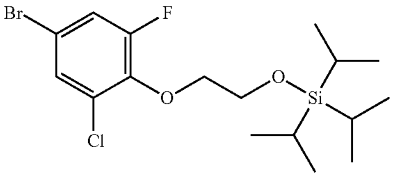 | 1 | NMR2: 0.99-1.16 (21H, m), 4.03 (2H, t, J = 5.3 Hz), 4.15-4.23 (2H, m), 7.17 (1H, dd, J = 2.3, 10.0 Hz), 7.31 (1H, t, J = 2.1 Hz). |

TABLE 1-2-continued
| REX | STR | RProp | DATA |
|---|---|---|---|
| 16 | 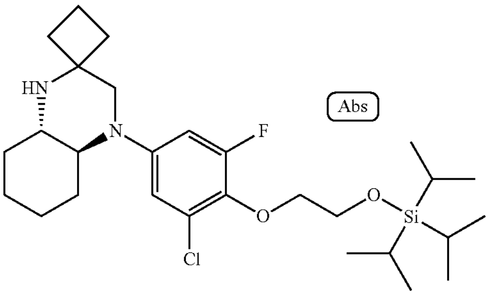 | 2 | NMR2: 0.84-1.17 (22H, m), 1.17-1.40 (3H, m), 1.49-1.91 (10H, m), 2.22-2.32 (1H, m), 2.37-2.48 (1H, m), 2.49-2.59 (1H, m), 2.64 (1H, dd, J = 1.4, 11.1 Hz), 3.04 (1H, d, J = 11.0 Hz), 4.04 (2H, t, J = 5.4 Hz), 4.16 (2H, t, J = 5.4 Hz), 6.78 (1H, dd, J = 2.5, 12.0 Hz), 6.91 (1H, dd, J = 1.8, 2.5 Hz). |
| 17 | 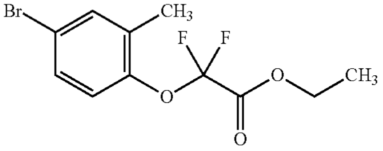 | 3 | NMR2: 1.37 (3H, t, J = 7.1 Hz), 2.28 (3H, s), 4.40 (2H, q, J = 7.1 Hz), 7.05-7.12 (1H, m), 7.27-7.33 (1H, m), 7.38 (1H, d, J = 2.3 Hz). |
TABLE 1-3
| REX | STR | RProp | DATA |
|---|---|---|---|
| 18 | 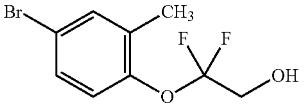 | 4 | NMR2: 2.14 (1H, t, J = 7.4 Hz), 2.25 (3H, s), 4.03 (2H, td, J = 7.4, 8.8 Hz), 7.07-7.14 (1H, m), 7.29 (1H, ddd, J = 0.7, 2.5, 8.7 Hz), 7.34-7.39 (1H, m). |
| 19 | 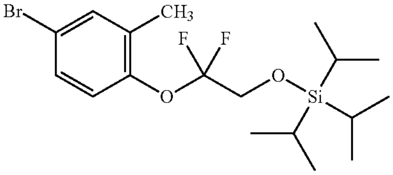 | 5 | NMR2: 1.05-1.22 (21H, m), 2.25 (3H, s), 4.11 (2H, t, J = 8.6 Hz), 7.07-7.13 (1H, m), 7.25-7.30 (1H, m), 7.32-7.37 (1H, m). |
| 20 | 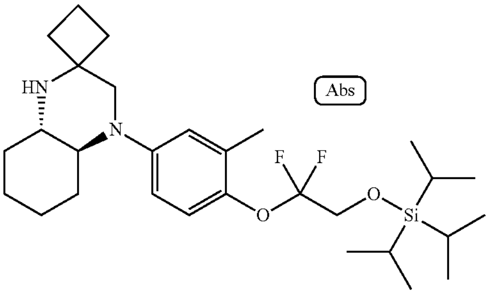 | 6 | NMR2: 0.83-1.02 (1H, m), 1.03-1.41 (24H, m), 1.53-1.92 (10H, m), 2.25 (3H, s), 2.29-2.39 (1H, m), 2.42-2.61 (2H, m), 2.65-2.73 (1H, m), 3.07 (1H, d, J = 11.1 Hz), 4.11 (2H, t, J = 8.6 Hz), 6.89-6.98 (2H, m), 7.10-7.08 (1H, m). |
| 21 | 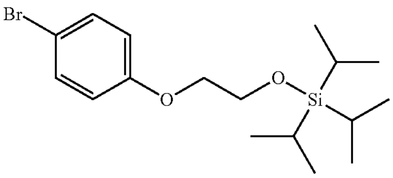 | 1 | NMR2: 1.01-1.20 (21H, m), 4.03 (4H, s), 6.75-6.83 (2H, m), 7.32-7.39 (2H, m). |

TABLE 1-3-continued
| REX | STR | RProp | DATA |
|---|---|---|---|
| 22 | 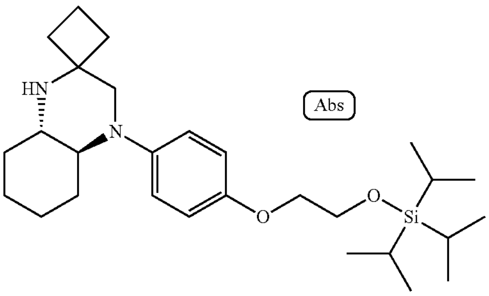 | 2 | NMR2: 0.84-1.01 (1H, m), 1.02-1.40 (24H, m), 1.49-1.91 (10H, m), 2.28-2.37 (1H, m), 2.43-2.61 (2H, m), 2.70 (1H, dd, J = 1.5, 11.1 Hz), 3.03 (1H, d, J = 11.0 Hz), 4.03 (4H, s), 6.80-6.89 (2H, m), 7.01-7.10 (2H, m). |
| 23 | 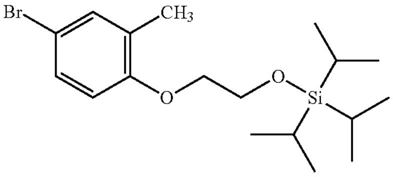 | 1 | NMR2: 1.04-1.18 (21H, m), 2.19 (3H, s), 4.01-4.07 (4H, m), 6.68-6.74 (1H, m), 7.19-7.25 (2H, m). |
| 24 | 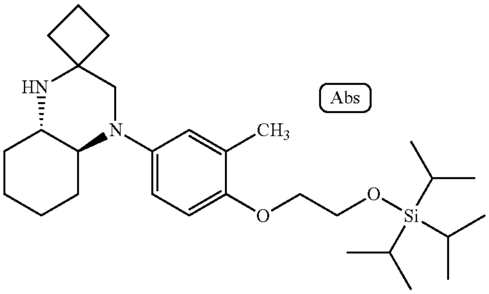 | 2 | NMR2: 0.84-1.01 (1H, m), 1.02-1.40 (24H, m), 1.54-1.91 (10H, m), 2.20 (3H, s), 2.27-2.37 (1H, m), 2.44-2.60 (2H, m), 2.66-2.73 (1H, m), 3.03 (1H, d, J = 11.1 Hz), 4.00-4.07 (4H, m), 6.77 (1H, d, J = 8.2 Hz), 6.87-6.97 (2H, m). |
| 25 | 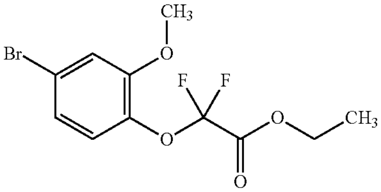 | 3 | NMR2: 1.38 (3H, t, J = 7.1 Hz), 3.85 (3H, s), 4.39 (2H, q, J = 7.1 Hz), 7.06 (1H, dd, J = 2.2, 8.5 Hz), 7.09-7.14 (2H, m). |
| 26 | 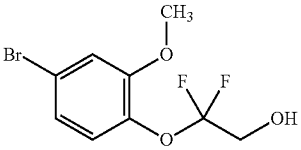 | 4 | NMR2: 2.55 (1H, brs), 3.86 (3H, s), 3.91-4.01 (2H, m), 7.03-7.17 (3H, m). |
TABLE 1-4
| REX | STR | RProp | DATA |
|---|---|---|---|
| 27 | 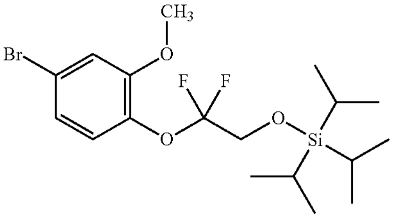 | 5 | NMR2: 1.04-1.22 (21H, m), 3.82 (3H, s), 4.13 (2H, t, J = 9.4 Hz), 7.03 (1H, dd, J = 2.2, 8.5 Hz), 7.07 (1H, d, J = 2.2 Hz), 7.10-7.15 (1H, m). |

TABLE 1-4-continued
| REX | STR | RProp | DATA |
| --- | --- | --- | --- |
| 28 | 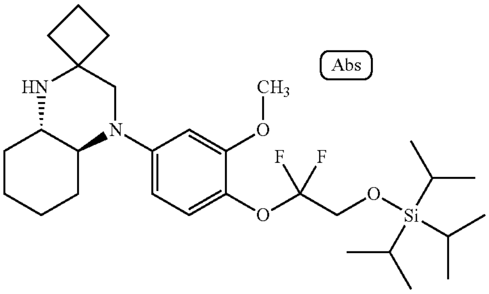 | 6 | NMR2: 0.84-1.03 (1H, m), 1.04-1.38 (24H, m), 1.49-1.92 (10H, m), 2.29-2.39 (1H, m), 2.42-2.53 (1H, m), 2.53-2.62 (1H, m), 2.71 (1H, dd, J = 1.5, 11.1 Hz), 3.09 (1H, d, J = 11.1 Hz), 3.81 (3H, s), 4.14 (2H, t, J = 9.5 Hz), 6.69 (1H, dd, J = 2.4, 8.5 Hz), 6.73 (1H, d, J = 2.3 Hz), 7.17 (1H, dt, J = 1.3, 8.4 Hz). |
| 29 | 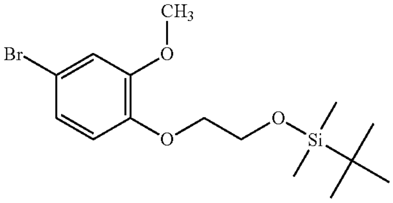 | 1 | NMR2: 0.08 (6H, s), 0.90 (9H, s), 3.84 (3H, s), 3.94-4.01 (2H, m), 4.03-4.10 (2H, m), 6.80 (1H, d, J = 8.5 Hz), 6.95-7.03 (2H, m). |
| 30 | 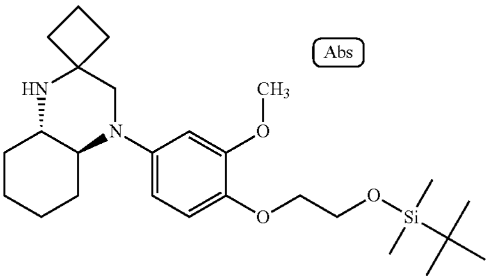 | 2 | NMR2: 0.09 (6H, s), 0.83-1.07 (10H, m), 1.10-2.00 (13H, m), 2.26-2.36 (1H, m), 2.41-2.61 (2H, m), 2.71 (1H, dd, J = 1.5, 11.1 Hz), 3.05 (1H, d, J = 11.0 Hz), 3.83 (3H, s), 3.95-4.02 (2H, m), 4.03-4.11 (2H, m), 6.65-6.73 (2H, m), 6.85 (1H, d, J = 8.3 Hz). |
| 31 | 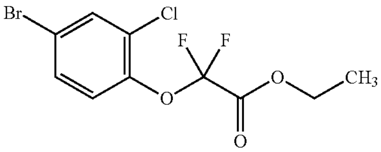 | 3 | NMR2: 1.39 (3H, t, J = 7.1 Hz), 4.42 (2H, q, J = 7.2 Hz), 7.22 (1H, dt, J = 1.3, 8.7 Hz), 7.40 (1H, dd, J = 2.4, 8.7 Hz), 7.61 (1H, d, J = 2.4 Hz). |
| 32 | 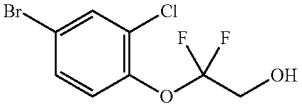 | 4 | NMR2: 2.12 (1H, brs), 4.06 (2H, t, J = 8.9 Hz), 7.21-7.28 (1H, m), 7.39 (1H, dd, J = 2.3, 8.7 Hz), 7.60 (1H, d, J = 2.4 Hz). |
| 33 | 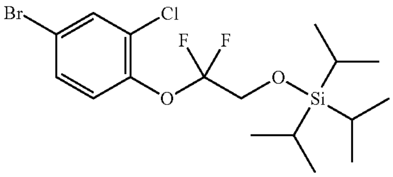 | 5 | NMR2: 1.03-1.23 (21H, m), 4.16 (2H, t, J = 9.3 Hz), 7.24 (1H, dt, J = 1.3, 8.8 Hz), 7.36 (1H, dd, J = 2.4, 8.7 Hz), 7.58 (1H, d, J = 2.3 Hz). |
| 34 | 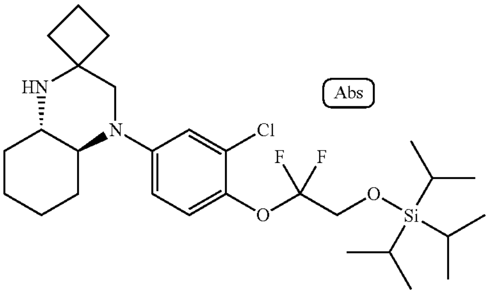 | 6 | NMR2: 0.84-1.01 (1H, m), 1.02-1.40 (24H, m), 1.43-1.92 (10H, m), 2.29-2.38 (1H, m), 2.41-2.50 (1H, m), 2.50-2.61 (1H, m), 2.66-2.73 (1H, m), 3.08 (1H, d, J = 11.0 Hz), 4.16 (2H, t, J = 9.3 Hz), 6.99 (1H, dd, J = 2.5, 8.7 Hz), 7.17 (1H, d, J = 2.5 Hz), 7.23-7.31 (1H, m). |

TABLE 1-4-continued
| REX | STR | RProp | DATA |
|---|---|---|---|
| 35 | 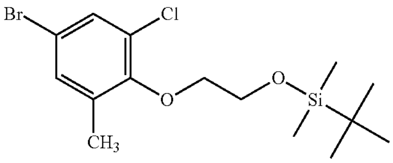 | 1 | NMR2: 0.10 (6H, s), 0.91 (9H, s), 2.30 (3H, s), 3.92-4.01 (4H, m), 7.19-7.22 (1H, m), 7.32-7.36 (1H, m). |
TABLE 1-5
| REX | STR | RProp | DATA |
|---|---|---|---|
| 36 | 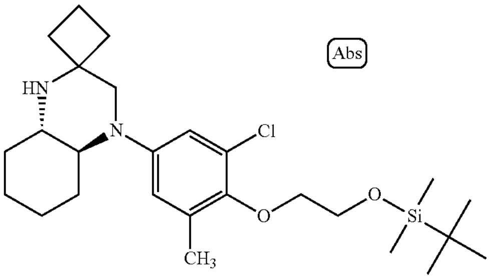 | 2 | NMR2: 0.10 (6H, s), 0.81-1.04 (10H, m), 1.13-1.90 (13H, m), 2.22-2.36 (4H, m), 2.41-2.59 (2H, m), 2.66 (1H, dd, J = 1.4, 11.2 Hz), 3.03 (1H, d, J = 11.1 Hz), 3.93-4.03 (4H, m), 6.80-6.85 (1H, m), 6.94-6.99 (1H, m). |
| 37 | 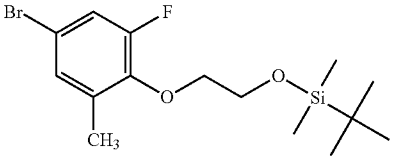 | 1 | NMR2: 0.07 (6H, d, J = 1,4 Hz), 0.89 (9H, s), 2.27 (3H, s), 3.87-3.93 (2H, m), 4.05-4.12 (2H, m), 7.03-7.11 (2H, m). |
| 38 | 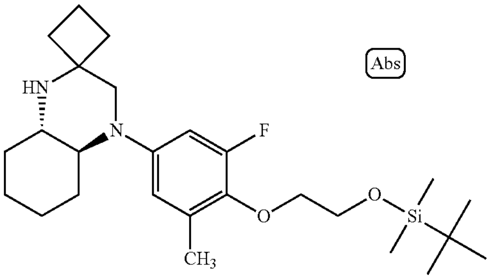 | 2 | NMR2: 0.08 (6H, s), 0.77-1.05 (10H, s), 1.13-1.43 (3H, m), 1.47-1.92 (10H, m), 2.21-2.36 (4H, m), 2.41-2.58 (2H, m), 2.61-2.69 (1H, m), 3.04 (1H, d, J = 11.0 Hz), 3.85-3.97 (2H, m), 4.01-4.12 (2H, m), 6.65-6.74 (2H, m). |
| 39 | 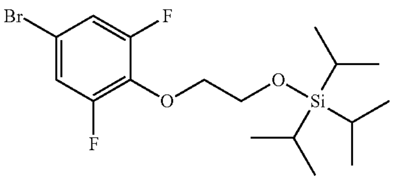 | 1 | NMR2: 0.99-1.16 (21H, m), 3.98-4.04 (2H, m), 4.18-4.25 (2H, m), 7.00-7.11 (2H, m). |
| 40 | 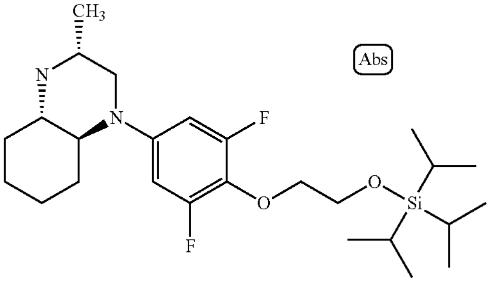 | 2 | NMR2: 0.84-1.16 (25H, m), 1.17-1.82 (8H, m), 2.25 (1H, ddd, J = 3.2, 8.5, 11.4 Hz), 2.41 (1H, dd, J = 10.1, 11.1 Hz), 2.47-2.61 (1H, m), 2.97 (1H, dd, J = 2.8, 11.1 Hz), 3.08 (1H, dtt, J = 3.2, 6.2, 12.6 Hz), 4.03 (2H, t, J = 5.5 Hz), 4.16 (2H, t, J = 5.4 Hz), 6.79 (1H, dd, J = 2.5, 12.1 Hz), 6.92 (1H, dd, J = 1.8, 2.5 Hz). |

TABLE 1-5-continued

| REX | STR | RProp | DATA |
| --- | --- | --- | --- |
| 41 | 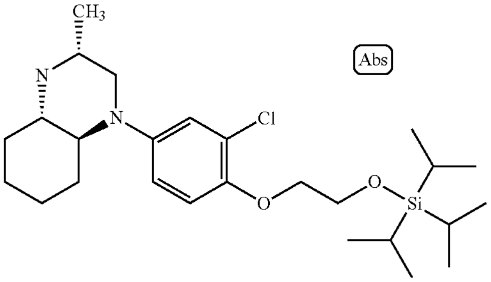 | 42 | NMR2: 0.86-1.68 (31H, m), 1.68-1.80 (2H, m), 2.27 (1H, ddd, J = 3.4, 8.5, 11.6 Hz), 2.46 (1H, dd, J = 10.1, 11.2 Hz), 2.56 (1H, ddd, J = 3.7, 8.5, 10.9 Hz), 2.95 (1H, dd, J = 2.8, 11.1 Hz), 3.04-3.16 (1H, m), 4.01-4.17 (4H, m), 6.91 (1H, d, J = 8.8 Hz), 6.97 (1H, dd, J = 2.5, 8.7 Hz), 7.16 (1H, d, J = 2.5 Hz). |
| 42 | 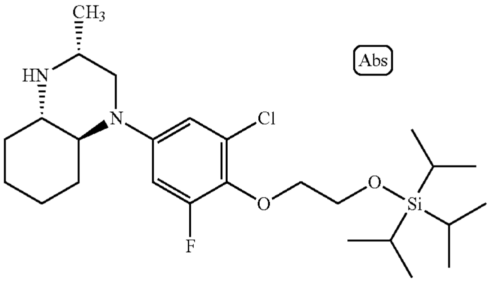 | 2 | NMR2: 0.85-1.17 (25H, m), 1.17-1.61 (4H, m), 1.61-1.82 (4H, m), 2.25 (1H, ddd, J = 3.3, 8.5, 11.5 Hz), 2.41 (1H, dd, J = 10.2, 11.1 Hz), 2.51-2.60 (1H, m), 2.96 (1H, dd, J = 2.8, 11.1 Hz), 3.03-3.14 (1H, m), 4.03 (2H, t, J = 5.5 Hz), 4.16 (2H, t, J = 5.4 Hz), 6.78 (1H, dd, J = 2.5, 12.1 Hz), 6.92 (1H, dd, J = 1.8, 2.5 Hz). |

TABLE 1-6

| REX | STR | RProp | DATA |
| --- | --- | --- | --- |
| 43 | 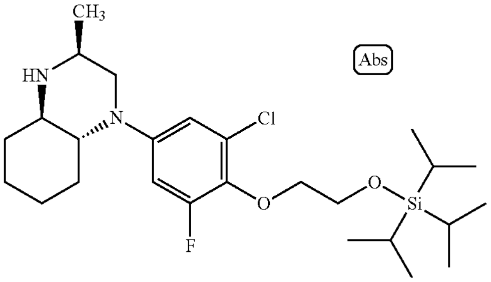 | 2 | NMR2: 0.85-1.17 (25H, m), 1.17-1.61 (4H, m), 1.61-1.82 (4H, m), 2.25 (1H, ddd, J = 3.3, 8.5, 11.5 Hz), 2.41 (1H, dd, J = 10.2, 11.1 Hz), 2.51-2.60 (1H, m), 2.96 (1H, dd, J = 2.8, 11.1 Hz), 3.03-3.14 (1H, m), 4.03 (2H, t, J = 5.5 Hz), 4.16 (2H, t, J = 5.4 Hz), 6.78 (1H, dd, J = 2.5, 12.1 Hz), 6.92 (1H, dd, J = 1.8, 2.5 Hz). |
| 44 | 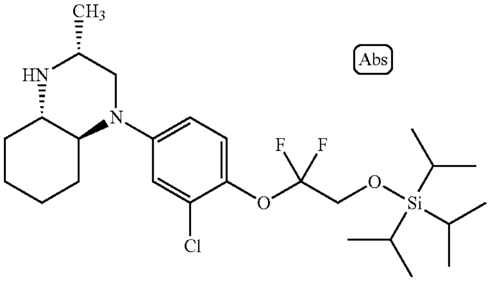 | 2 | NMR2: 0.85-1.84 (33H, m), 2.32 (1H, ddd, J = 3.1, 8.5, 11.4 Hz), 2.46 (1H, dd, J = 10.1, 11.2 Hz), 2.58 (1H, ddd, J = 3.7, 8.5, 10.8 Hz), 3.00 (1H, dd, J = 2.8, 11.1 Hz), 3.06-3.16 (1H, m), 4.16 (2H, t. J = 9.3 Hz), 6.99 (1H, dd, J = 2.6, 8.7 Hz), 7.18 (1H, d, J = 2.5 Hz), 7.27 (1H, dd, J = 1.4, 8.7 Hz). |
| 45 | 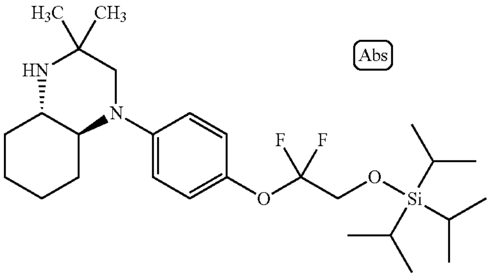 | 2 | NMR2: 0.83-1.59 (32H, m), 1.59-1.78 (4H, m), 2.18-2.29 (1H, m), 2.59 (1H, d, J = 11.2 Hz), 2.70-2.82 (2H, m), 4.07 (2H, t, J = 8.8 Hz), 6.99-7.07 (2H, m), 7.08-7.15 (2H, m). |

TABLE 1-6-continued
| REX | STR | RProp | DATA |
|---|---|---|---|
| 46 | 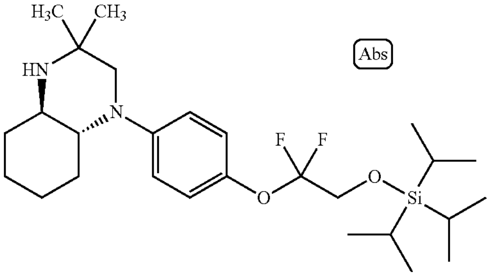 | 2 | NMR2: 0.81-1.59 (32H, m), 1.59-1.78 (4H, m), 2.18-2.29 (1H, m), 2.59 (1H, d, J = 11.2 Hz), 2.70-2.82 (2H, m), 4.07 (2H, t, J = 8.8 Hz), 6.99-7.07 (2H, m), 7.08-7.15 (2H, m). |
| 47 | 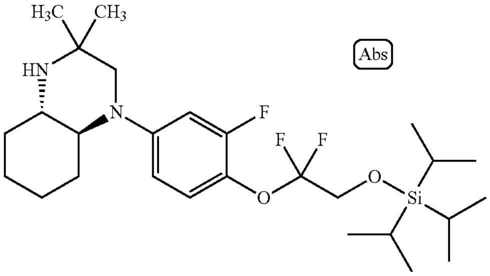 | 2 | NMR2: 0.80-1.45 (32H, m), 1.59-1.82 (4H, m), 2.22 (1H, ddd, J = 3.0, 8.7, 11.5 Hz), 2.59 (1H, d, J = 11.3 Hz), 2.70-2.87 (2H, m), 4.13 (2H, t, J = 9.1 Hz), 6.80 (1H, ddd, J = 1.3, 2.6, 8.7 Hz), 6.85 (1H, dd, J = 2.5, 11.8 Hz), 7.15-7.23 (1H, m). |
| 48 | 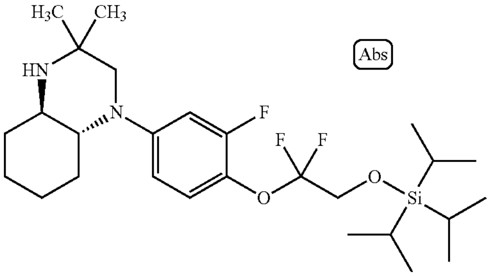 | 2 | NMR2: 0.80-1.45 (32H, m), 1.59-1.82 (4H, m), 2.22 (1H, ddd, J = 3.0, 8.7, 11.5 Hz), 2.59 (1H, d, J = 11.3 Hz), 2.70-2.87 (2H, m), 4.13 (2H, t, J = 9.1 Hz), 6.80 (1H, ddd, J = 1.3, 2.6, 8.7 Hz), 6.85 (1H, dd, J = 2.5, 11.8 Hz), 7.15-7.23 (1H, m). |
| 49 | 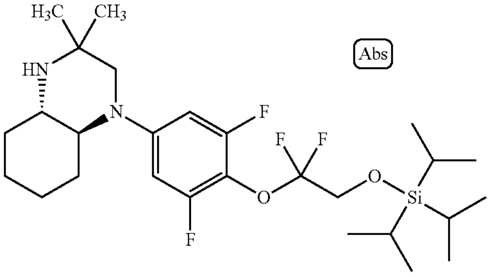 | 2 | NMR2: 0.81-1.46 (32H, m), 1.66-1.87 (3H, m), 1.88-2.01 (1H, m), 2.51-2.64 (1H, m), 2.69-2.83 (1H, m), 2.89 (1H, d, J = 12.6 Hz), 3.00 (1H, d, J = 12.6 Hz), 4.65 (2H, s), 6.31-6.45 (2H, m). |
TABLE 1-7
| REX | STR | RProp | DATA |
|---|---|---|---|
| 50 | 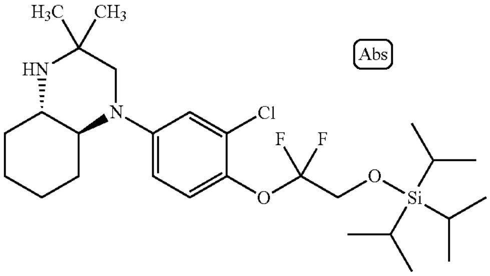 | 2 | NMR2: 0.91-1.52 (32H, m), 1.64-1.84 (4H, m), 2.38 (1H, ddd, J = 3.2, 9.0, 11.8 Hz), 2.66-2.81 (2H, m), 2.87 (1H, d, J = 11.7 Hz), 4.65 (2H, s), 6.83 (1H, dd, J = 2.2, 8.4 Hz), 7.00 (1H, d, J = 2.1 Hz), 7.34 (1H, d, J = 8.4 Hz). |

TABLE 1-7-continued
| REX | STR | RProp | DATA |
|---|---|---|---|
| 51 | 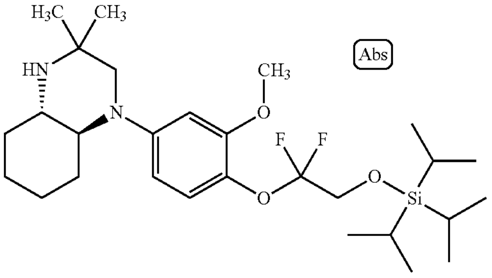 | 2 | NMR2: 0.92-1.43 (32H, m), 1.60-1.83 (4H, m), 2.33 (1H, ddd, J = 3.2, 8.9, 11.9 Hz), 2.66 (1H, d, J = 11.5 Hz), 2.72-2.81 (1H, m), 2.85 (1H, d, J = 11.4 Hz), 3.83 (3H, s), 4.64 (2H, s), 6.53 (1H, d, J = 1.9 Hz), 6.59 (1H, dd, J = 1.9, 8.2 Hz), 7.28 (1H, d, J = 8.2 Hz). |
| 52 | 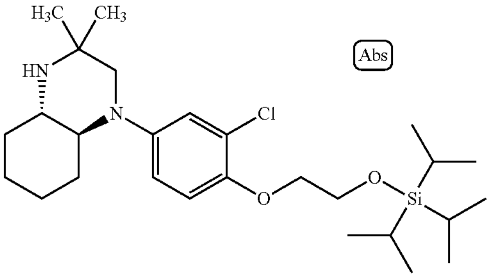 | 2 | NMR2: 0.83-1.41 (32H, m), 1.53-1.77 (4H, m), 2.16 (1H, ddd, J = 3.3, 8.8, 11.5 Hz), 2.56 (1H, d, J = 11.1 Hz), 2.67-2.78 (2H, m), 4.01-4.18 (4H, m), 6.86-6.97 (2H, m), 7.11 (1H, d, J = 2.3 Hz). |
| 53 | 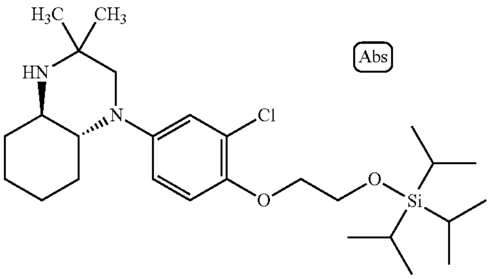 | 2 | NMR2: 0.83-1.41 (32H, m), 1.53-1.77 (4H, m), 2.16 (1H, ddd, J = 3.3, 8.8, 11.5 Hz), 2.56 (1H, d, J = 11.1 Hz), 2.67-2.78 (2H, m), 4.01-4.18 (4H, m), 6.86-6.97 (2H, m), 7.11 (1H, d, J = 2.3 Hz). |
| 54 | 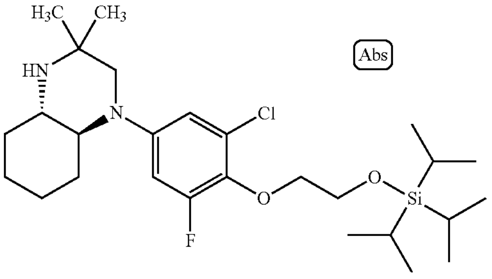 | 2 | NMR2: 0.80-1.43 (32H, m), 1.59-1.77 (4H, m), 2.11-2.21 (1H, m), 2.55 (1H, d, J = 11.2 Hz), 2.68-2.80 (2H, m), 4.03 (2H, t, J = 5.4 Hz), 4.15 (2H, t, J = 5.5 Hz), 6.73 (1H, dd, J = 2.5, 12.1 Hz), 6.84-6.88 (1H, m). |
| 55 | 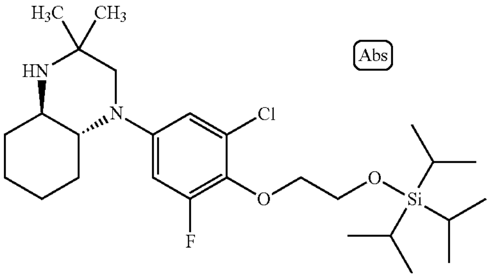 | 2 | NMR2: 0.80-1.43 (32H, m), 1.59-1.77 (4H, m), 2.11-2.21 (1H, m), 2.55 (1H, d, J = 11.2 Hz), 2.68-2.80 (2H, m), 4.03 (2H, t, J = 5.4 Hz), 4.15 (2H, t, J = 5.5 Hz), 6.73 (1H, dd, J = 2.5, 12.1 Hz), 6.84-6.88 (1H, m). |

TABLE 1-7-continued
| REX | STR | RProp | DATA |
|---|---|---|---|
| 56 | 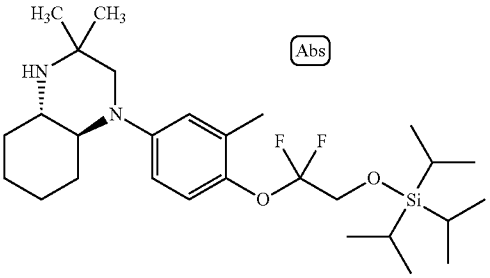 | 6 | NMR2: 0.76-1.41 (32H, m), 1.58-1.78 (4H, m), 2.16-.2.29 (4H, m), 2.54-2.62 (1H, m), 2.70-2.80 (2H, m), 4.10 (2H, t, J = 8.6 Hz), 6.84-6.93 (2H, m), 7.12 (1H, d, J = 8.5 Hz). |
TABLE 1-8
| REX | STR | RProp | DATA |
|---|---|---|---|
| 57 | 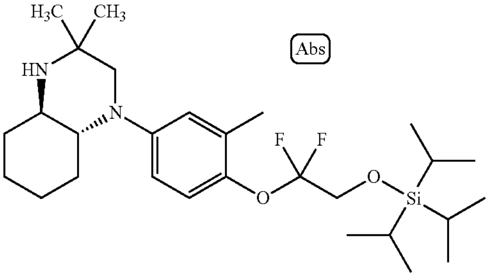 | 2 | NMR2: 0.76-1.41 (32H, m), 1.58-1.78 (4H, m), 2.16-.2.29 (4H, m), 2.54-2.62 (1H, m), 2.70-2.80 (2H, m), 4.10 (2H, t, J = 8.6 Hz), 6.84-6.93 (2H, m), 7.12 (1H, d, J = 8.5 Hz). |
| 58 | 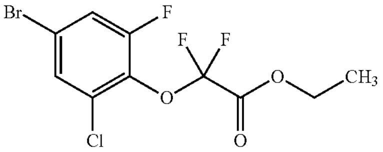 | 3 | NMR2: 1.41 (3H, t, J = 7.2 Hz), 4.44 (2H, q, J = 7.1 Hz), 7.30 (1H, dd, J = 2.3, 8.9 Hz), 7.43 (1H, t, J = 2.1 Hz). |
| 59 | 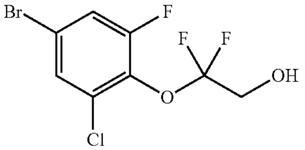 | 4 | NMR2: 2.10-2.20 (1H, m), 4.06-4.16 (2H, m), 7.29 (1H, dd, J = 2.3, 8.9 Hz), 7.42 (1H, t, J = 2.1 Hz). |
| 60 | 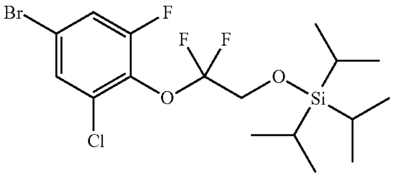 | 5 | NMR2: 1.01-1.28 (21H, m), 4.20 (2H, t, J = 9.4 Hz), 7.26 (1H, dd, J = 2.3, 8.9 Hz), 7.40 (1H, t, J = 2.1 Hz). |
| 61 | 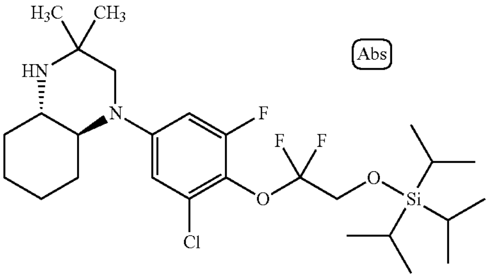 | 6 | NMR2: 0.65-1.81 (32H, m), 1.65-1.81 (4H, m), 2.26 (1H, ddd, J = 3.1, 9.0, 11.7 Hz), 2.63 (1H, d, J = 11.5 Hz), 2.75 (1H, ddd, J = 3.3, 8.9, 10.8 Hz), 2.82 (1H, d, J = 11.5 Hz), 4.20 (2H, t, J = 9.5 Hz), 6.74 (1H, dd, J = 2.5, 11.4 Hz), 6.87 (1H, dd, J = 1.8, 2.5 Hz). |

TABLE 1-8-continued
| REX | STR | RProp | DATA |
|---|---|---|---|
| 62 | 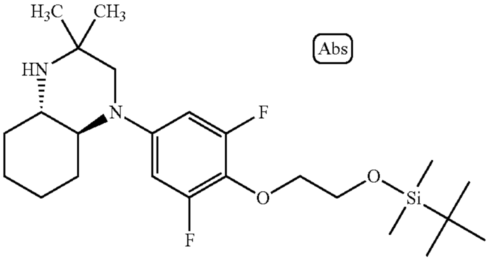 | 2 | NMR2: 0.07 (6H, s), 0.87 (9H, s), 0.94-1.10 (4H, m), 1.14-1.47 (7H, m), 1.61-1.78 (4H, m), 2.11-2.20 (1H, m), 2.54 (1H, d, J = 11.2 Hz), 2.68-2.78 (2H, m), 3.87-3.96 (2H, m), 4.10-4.19 (2H, m), 6.55-6.66 (2H, m). |
| 63 | 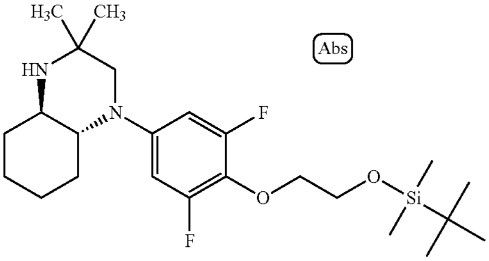 | 2 | NMR2: 0.07 (6H, s), 0.87 (9H, s), 0.94-1.10 (4H, m), 1.14-1.47 (7H, m), 1.61-1.78 (4H, m), 2.11-2.20 (1H, m), 2.54 (1H, d, J = 11.2 Hz), 2.68-2.78 (2H, m), 3.87-3.96 (2H, m), 4.10-4.19 (2H, m), 6.55-6.66 (2H, m). |
| 64 | 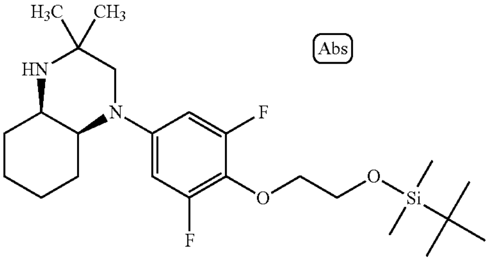 | 2 | NMR2: 0.89 (1H, brs), 0.98-1.15 (21H, m), 1.18 (3H, s), 1.21 (3H, s), 1.22-1.32 (2H, m), 1.32-1.48 (2H, m), 1.61-1.79 (4H, m), 2.65 (1H, d, J = 11.8 Hz), 2.86 (1H, d, J = 11.8 Hz), 3.36-3.41 (1H, m), 3.47 (1H, dt, J = 4.0, 11.9 Hz), 3.99 (2H, t, J = 5.3 Hz), 4.08 (2H, t, J = 5.5 Hz), 6.26-6.38 (2H, m). |
TABLE 1-9
| REX | STR | RProp | DATA |
|---|---|---|---|
| 65 | 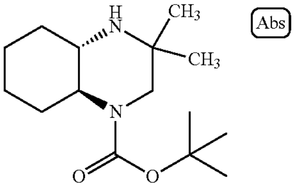 | 65 | NMR2: 0.85-1.43 (11H, m), 1.46 (9H, s), 1.63-1.93 (3H, m), 2.09-2.23 (1H, m), 2.50-2.67 (1H, m), 2.95 (1H, d, J = 13.9 Hz), 3.04-3.19 (1H, m), 3.56 (1H, d, J = 13.9 Hz). |
| 66 | 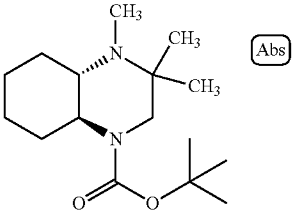 | 66 | NMR2: 0.91 (3H, s), 1.11 (3H, s), 1.12-1.42 (4H, m), 1.44 (9H, s), 1.64-1.88 (2H, m), 1.90-2.10 (2H, m), 2.17 (3H, s), 2.38-2.51 (1H, m), 2.95 (1H, d, J = 13.9 Hz), 3.24-3.40 (1H, m), 3.57 (1H, d, J = 13.9 Hz). |
| 67 | 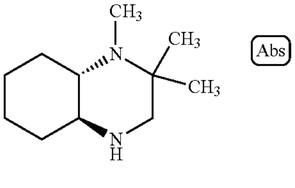 | 67 | NMR2: 0.91-1.85 (14H, m), 1.91-2.1 (2H, m), 2.18 (3H, s), 2.30-2.42 (1H, m), 2.62 (1H, d, J = 12.1 Hz), 2.80 (1H, d, J = 12.1 Hz). |

TABLE 1-9-continued
| REX | STR | RProp | DATA |
|---|---|---|---|
| 68 | 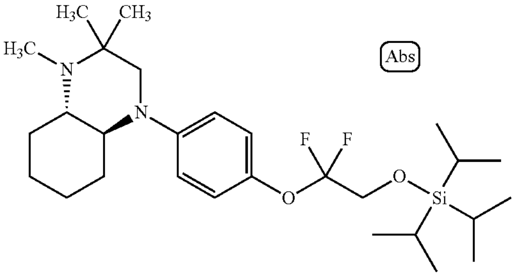 | 68 | NMR2: 0.91-1.35 (30H, m), 1.52-1.69 (3H, m), 1.71-1.82 (1H, m), 2.06-2.15 (1H, m), 2.23 (3H, s), 2.28 (1H, ddd, J = 3.4, 8.7, 10.9 Hz), 2.52 (1H, ddd, J = 3.1, 8.7, 11.6 Hz), 2.65 (1H, d, J = 11.3 Hz), 2.79 (1H, d, J = 11.3 Hz), 4.07 (2H, t, J = 8.8 Hz), 7.02-7.08 (2H, m), 7.08-7.15 (2H, m). |
| 69 | 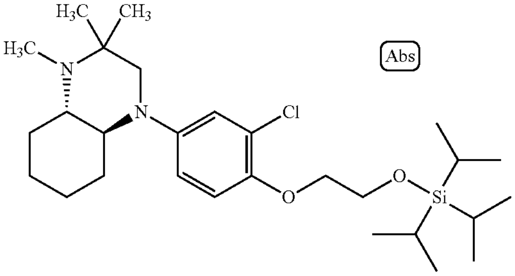 | 68 | NMR2: 0.94-1.34 (31H, m), 1.50-1.63 (2H, m), 1.71-1.81 (1H, m), 2.04-2.14 (1H, m), 2.18-2.31 (4H, m), 2.45 (1H, ddd, J = 3.1, 8.8, 11.4 Hz), 2.59 (1H, d, J = 11.1 Hz), 2.77 (1H, d, J = 11.2 Hz), 4.03-4.14 (4H, m), 6.90 (1H, d, J = 8.7 Hz), 6.95 (1H, dd, J = 2.4, 8.7 Hz), 7.12 (1H, d, J = 2.4 Hz). |
| 70 | 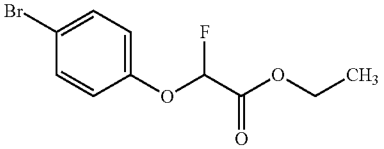 | 3 | NMR2: 1.36 (3H, t, J = 7.2 Hz), 4.36 (2H, q, J = 7.2 Hz), 5.90 (1H, d, J = 59.4 Hz), 6.98-7.06 (2H, m), 7.42-7.51 (2H, m). |
| 71 | 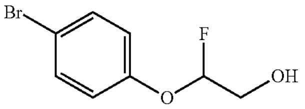 | 4 | NMR2: 1.87 (1H, dt, J = 3.7, 7.5 Hz), 3.82-3.99 (2H, m), 5.79 (1H, td, J = 4.5, 62.1 Hz), 6.94-7.02 (2H, m), 7.40-7.49 (2H, m). |
| 72 | 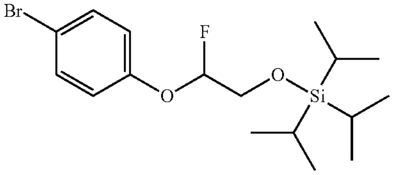 | 5 | NMR2: 0.90-1.33 (21H, m), 3.92-4.07 (2H, m), 5.73 (1H, td, J = 4.7, 61.6 Hz), 6.94-7.01 (2H, m), 7.39-7.46 (2H, m). |
| 73 | 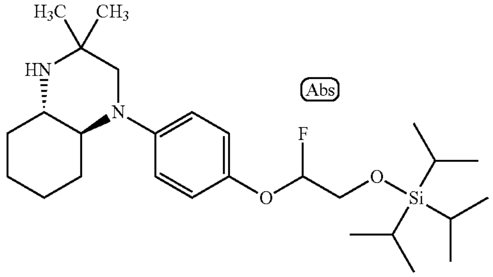 | 6 | NMR2: 0.75-1.45 (32H, m), 1.53-1.77 (4H, m), 2.15-2.27 (1H, m), 2.58 (1H, d, J = 11.2 Hz), 2.70-2.82 (2H, m), 3.92-4.06 (2H, m), 5.74 (1H, tdd, J = 3.2, 4.7, 62.2 Hz), 6.96-7.09 (4H, m). |
TABLE 1-10
| REX | STR | RProp | DATA |
|---|---|---|---|
| 74 | 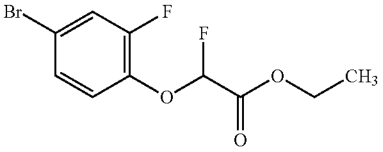 | 3 | NMR2: 1.36 (3H, t, J = 7.1 Hz), 4.37 (2H, q, J = 7.1 Hz), 5.87 (1H, d, J = 58.7 Hz), 7.13 (1H, td, J = 1.1, 8.5 Hz), 7.22-7.29 (1H, m), 7.33 (1H, dd, J = 2.3, 9.9 Hz). |

TABLE 1-10-continued
| REX | STR | RProp | DATA |
| --- | --- | --- | --- |
| 75 | 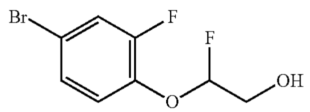 | 4 | NMR2: 1.99 (1H, td, J = 1.2, 7.1 Hz), 3.88-4.00 (2H, m), 5.73 (1H, td, J = 4.6, 61.5 Hz), 7.12 (1H, td, J = 1.2, 8.6 Hz), 7.22-7.28 (1H, m), 7.31 (1H, dd, J = 2.3, 10.0 Hz). |
| 76 | 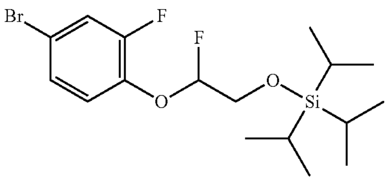 | 5 | NMR2: 0.96-1.31 (21H, m), 4.01 (1H, d, J = 4.7 Hz), 4.04 (1H, dd, J = 1.5, 4.7 Hz), 5.70 (1H, td, J = 4.7, 61.4 Hz), 7.11 (1H, td, J = 1.1, 8.6 Hz), 7.23 (1H, ddd, J = 1.5, 2.3, 8.8 Hz), 7.29 (1H, dd, J = 2.3, 10.0 Hz). |
| 77 | 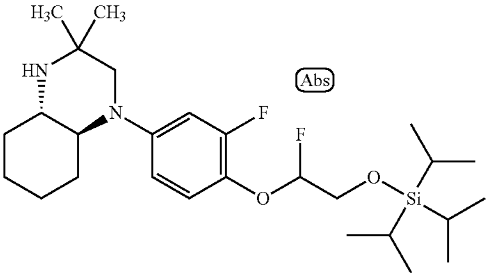 | 6 | NMR2: 0.68-1.45 (32H, m), 1.45-1.78 (4H, m), 2.14-2.24 (1H, m), 2.57 (1H, d, J = 11.2 Hz), 2.69-2.82 (2H, m), 4.00 (1H, d, J = 4.7 Hz), 4.04 (1H, dd, J = 3.4, 4.7 Hz), 5.68 (1H, tdd, J = 1.4, 4.6, 62.1 Hz), 6.81 (1H, ddd, J = 1.3, 2.5, 8.7 Hz), 6.86 (1H, dd, J = 2.4, 12.2 Hz), 7.12 (1H, td, J = 1.1, 8.9 Hz). |
| 78 | 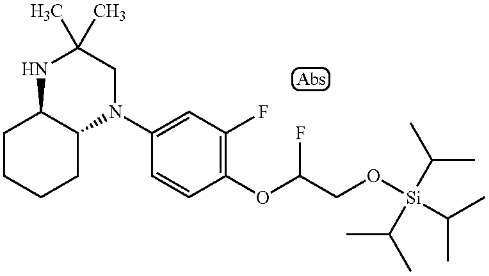 | 6 | NMR2: 0.68-1.45 (32H, m), 1.45-1.78 (4H, m), 2.14-2.24 (1H, m), 2.57 (1H, d, J = 11.2 Hz), 2.69-2.82 (2H, m), 4.00 (1H, d, J = 4.7 Hz), 4.04 (1H, dd, J = 3.4, 4.7 Hz), 5.68 (1H, tdd, J = 1.4, 4.6, 62.1 Hz), 6.81 (1H, ddd, J = 1.3, 2.5, 8.7 Hz), 6.86 (1H, dd, J = 2.4, 12.2 Hz), 7.12 (1H, td, J = 1.1, 8.9 Hz). |
| 79 | 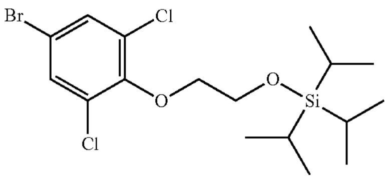 | 1 | NMR2: 1.01-1.20 (21H, m), 4.04-4.15 (4H, m), 7.43 (2H, s). |
| 80 | 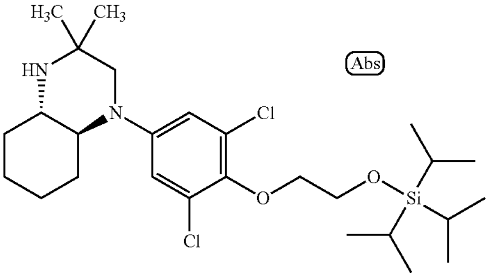 | 2 | NMR2: 0.93-1.42 (32H, m), 1.50-1.79 (4H, m), 2.13-2.22 (1H, m), 2.56 (1H, dd, J = 11.3 Hz), 2.68-2.78 (2H, m), 4.05-4.13 (4H, m), 6.99 (2H, s). |

TABLE 1-10-continued
| REX | STR | RProp | DATA |
|---|---|---|---|
| 81 | 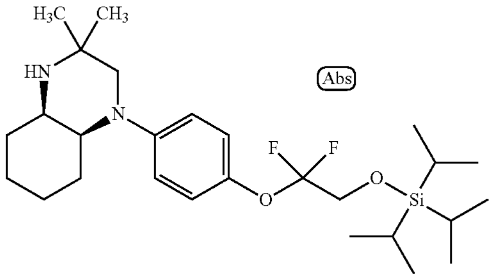 | 2 | NMR2: 1.06-1.47 (32H, m), 1.62-1.80 (4H, m), 2.71 (1H, d, J = 11.7 Hz), 2.94 (1H, d, J = 11.7 Hz), 3.43 (1H, d, J = 3.4 Hz), 3.55-3.63 (1H, m), 4.06 (2H, t, J = 8.8 Hz), 6.75-6.82 (2H, m), 7.02-7.08 (2H, m) |
TABLE 1-11
| REX | STR | RProp | DATA |
|---|---|---|---|
| 82 | 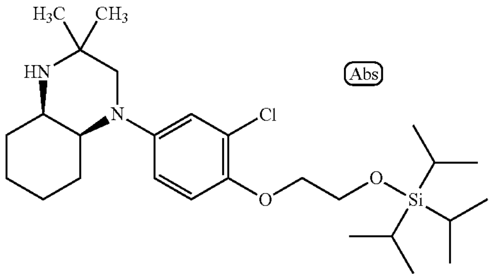 | 82 | NMR2: 1.03-1.42 (32H, m), 1.59-1.75 (4H, m), 2.68 (1H, d, J = 11.6 Hz), 2.82 (1H, d, J = 11.6 Hz), 3.39-3.53 (2H, m), 4.00-4.10 (4H, m), 6.68 (1H, dd, J = 9.0, 2.9 Hz), 6.85 (1H, d, J = 2.9 Hz), 6.90 (1H, d, J = 9.0 Hz). |
| 83 | 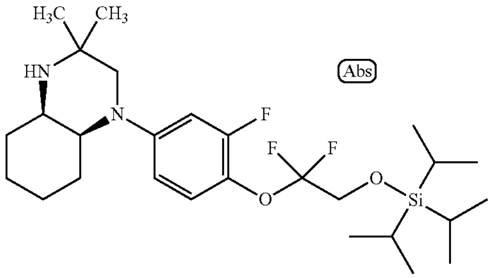 | 2 | NMR2: 1.04-1.43 (32H, m), 1.62-1.82 (4H, m), 2.69 (1H, d, J = 11.9 Hz), 2.95 (1H, d, J = 11.9 Hz), 3.37-3.44 (1H, m), 3.51-3.60 (1H, m), 4.11 (2H, t, J = 9.1 Hz), 6.48-6.61 (2H, m), 7.05-7.15 (1H, m) |
| 84 | 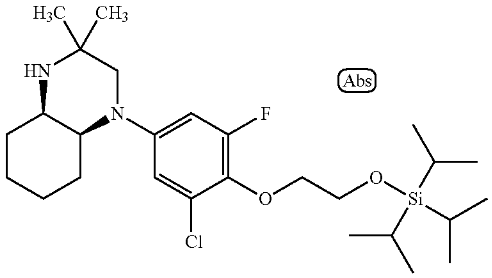 | 2 | NMR2: 0.98-1.45 (32H, m), 1.63-1.77 (4H, m), 2.66 (1H, d, J = 11.7 Hz), 2.86 (1H, d, J = 11.7 Hz), 3.36-3.42 (1H, m), 3.44-3.52 (1H, m), 3.98-4.11 (4H, m), 6.47 (1H, dd, J = 13.9, 3.0 Hz), 6.56 (1H, dd, J = 3.0, 1.7 Hz). |
| 85 | 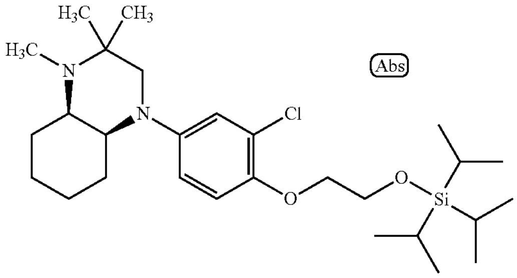 | 85 | NMR2: 0.93-1.58 (32H, m), 1.67-1.77 (1H, m), 1.96-2.11 (2H, m), 2.15 (3H, s), 2.75 (1H, d, J = 11.5 Hz), 2.88 (1H, d, J = 3.3 Hz), 2.95 (1H, d, J = 11.5 Hz), 3.49-3.57 (1H, m), 3.99-4.08 (4H, m), 6.66 (1H, dd, J = 9.0, 3.0 Hz), 6.83 (1H, d, J = 3.0 Hz), 6.89 (1H, d, J = 9.0 Hz). |

TABLE 1-11-continued

| REX | STR | RProp | DATA |
|---|---|---|---|
| 86 | 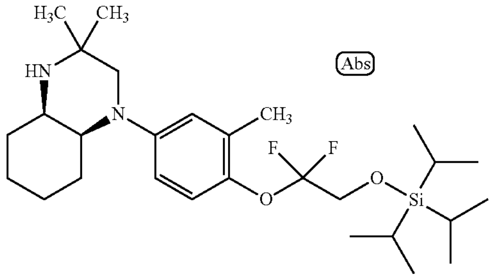 | 2 | NMR2: 1.05-1.47 (32H, m), 1.64-1.80 (4H, m), 2.23 (3H, s), 2.70 (1H, d, J = 11.7 Hz), 2.94 (1H, d, J = 11.7 Hz), 3.38-3.46 (1H, m), 3.54-3.63 (1H, m), 4.09 (2H, t, J = 8.6 Hz), 6.59-6.67 (2H, m), 7.02-7.09 (1H, m) |
| 87 | 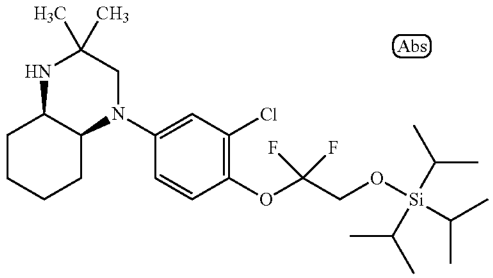 | 2 | NMR2: 0.97-1.48 (32H, m), 1.64-1.81 (4H, m), 2.70 (1H, d, J = 11.8 Hz), 2.93 (1H, d, J = 11.8 Hz), 3.38-3.43 (1H, m), 3.52-3.61 (1H, m), 4.14 (2H, t, J = 9.4 Hz), 6.68 (1H, dd, J = 9.2, 3.0 Hz), 6.82 (1H, d, J = 3.0 Hz), 7.12-7.20 (1H, m). |
| 88 | 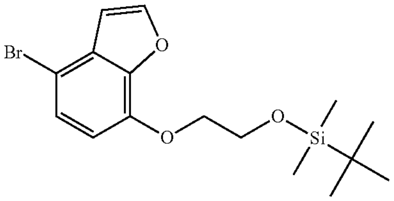 | 1 | NMR2: 0.11 (6H, s), 0.91 (9H, s), 4.05 (2H, t, J = 5.3 Hz), 4.26 (2H, t, J = 5.3 Hz), 6.74 (1H, d, J = 8.5 Hz), 6.79 (1H, d, J = 2.2 Hz), 7.27 (1H, d, J = 8.5 Hz), 7.66 (1H, d. J = 2.2 Hz). |

TABLE 1-12

| REX | STR | RProp | DATA |
|---|---|---|---|
| 89 | 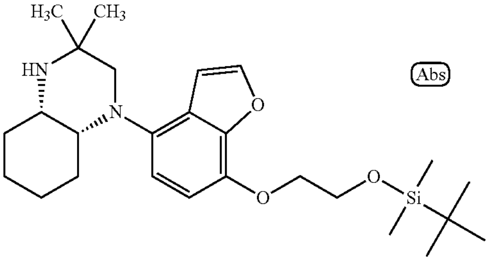 | 2 | NMR2: 0.10 (6H, s), 0.91 (9H, s), 1.00-1.11 (2H, m), 1.20 (3H, s), 1.32 (3H, s), 1.37-1.41 (2H, m), 1.60-1.90 (5H, m), 2.67 (1H, d, J = 11.3 Hz), 3.03 (1H, d, J = 11.3 Hz), 3.41-3.51 (1H, m), 3.58-3.63 (1H, m), 4.03 (2H, t, J = 5.6 Hz), 4.20 (2H, t, J = 5.6 Hz), 6.49 (1H, d, J = 8.4 Hz), 6.71 (1H, d, J = 8.4 Hz), 6.80 (1H, d, J = 2.2 Hz), 7.57 (1H, d, J = 2.2 Hz). |
| 90 | 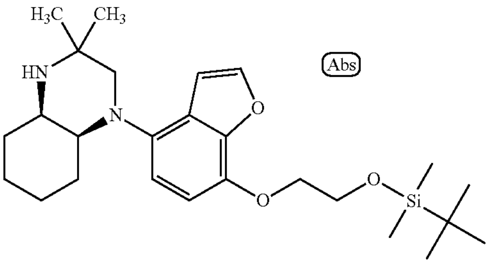 | 2 | NMR2: 0.10 (6H, s), 0.91 (9H, s), 0.98-1.11 (2H, m), 1.20 (3H, s), 1.32 (3H, s), 1.36-1.41 (2H, m), 1.61-1.91 (5H, m), 2.67 (1H, d, J = 11.3 Hz), 3.03 (1H, d, J = 11.3 Hz), 3.41-3.51 (1H, m), 3.57-3.64 (1H, m), 4.03 (2H, t, J = 5.6 Hz), 4.20 (2H, t, J = 5.6 Hz), 6.49 (1H, d, J = 8.4 Hz), 6.71 (1H, d, J = 8.4 Hz), 6.80 (1H, d, J = 2.2 Hz), 7.57 (1H, d, J = 2.2 Hz). |

TABLE 1-12-continued
| REX | STR | RProp | DATA |
|---|---|---|---|
| 91 | 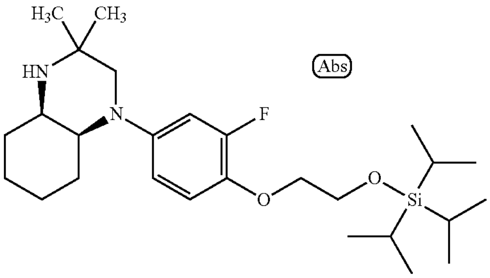 | 2 | NMR2: 0.98-1.29 (28H, m), 1.30-1.49 (4H, m), 1.61-1.79 (4H, m), 2.66 (1H, d, J = 11.6 Hz), 2.84 (1H, d, J = 11.6 Hz), 3.39-3.45 (1H, m), 3.45-3.54 (1H, m), 3.97-4.10 (4H, m), 6.46-6.53 (1H, m), 6.60 (1H, dd, J = 14.6, 2.9 Hz), 6.86-6.95 (1H, m). |
| 92 | 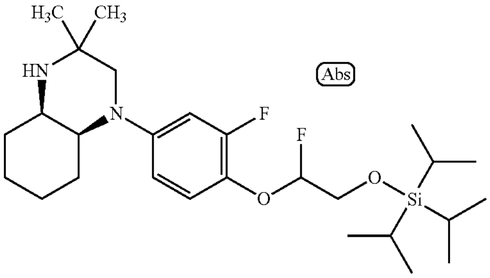 | 2 | NMR2: 0.99-1.31 (28H, m), 1.31-1.50 (4H, m), 1.62-1.80 (4H, m), 2.68 (1H, d, J = 11.8 Hz), 2.90 (1H, dd, J = 11.8, 1.9 Hz), 3.38-3.44 (1H, m), 3.49-3.58 (1H, m), 3.93-4.08 (2H, m), 5.44-5.74 (1H, m), 6.48-6.55 (1H, m), 6.58 (1H, dt, J = 14.2, 2.5 Hz), 7.06 (1H, t, J = 9.0 Hz). |
| 93 | 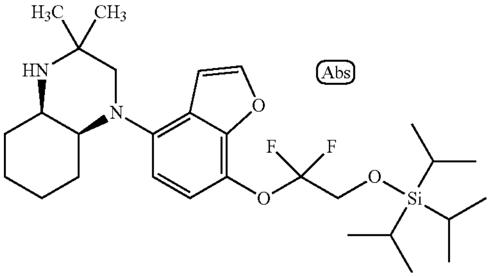 | 2 | NMR2: 1.00-1.26 (25H, m), 1.31 (3H, s), 1.33-1.50 (4H, m), 1.61-1.78 (3H, m), 1.80-1.95 (1H, m), 2.77 (1H, d, J = 11.4 Hz), 3.05 (1H, d, J = 11.4 Hz), 3.52-3.63 (2H, m), 4.19 (2H, t, J = 9.2 Hz), 6.51 (1H, d, J = 8.6 Hz), 6.81 (1H, d, J = 2.2 Hz), 7.02-7.09 (1H, m), 7.56 (1H, d, J = 2.2 Hz). |
| 94 | 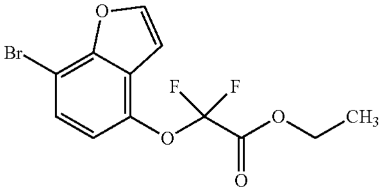 | 3 | NMR2: 1.37 (3H, t, J = 7.2 Hz), 4.40 (2H, q, J = 7.2 Hz), 6.93-6.99 (1H, m), 6.99-7.08 (1H, m), 7.43 (1H, d, J = 8.5 Hz), 7.67-7.72 (1H, m). |
| 95 | 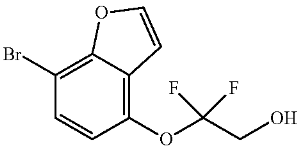 | 4 | NMR2: 2.15-2.23 (1H, m), 4.04-4.11 (2H, m), 6.89-6.95 (1H, m), 7.05 (1H, dt, J = 8.5, 1.2 Hz), 7.43 (1H, d, J = 8.5 Hz), 7.68 (1H, d, J = 2.2 Hz). |
TABLE 1-13
| REX | STR | RProp | DATA |
|---|---|---|---|
| 96 | 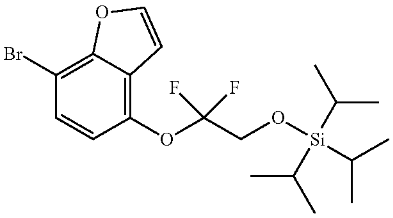 | 5 | NMR2: 1.04-1.28 (21H, m), 4.16 (2H, t, J = 8.6 Hz), 6.89-6.95 (1H, m), 7.01-7.08 (1H, m), 7.41 (1H, d, J = 8.5 Hz), 7.66 (1H, d, J = 2.2 Hz). |

TABLE 1-13-continued
| REX | STR | RProp | DATA |
|---|---|---|---|
| 97 | 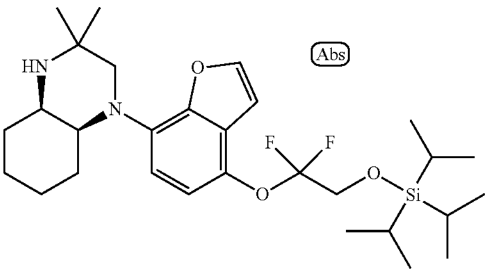 | 2 | NMR2: 1.00-1.25 (24H, m), 1.32 (3H, s), 1.35-1.52 (4H, m), 1.58-1.76 (4H, m), 1.78-1.93 (1H, m), 2.90-3.03 (2H, m), 3.59-3.64 (1H, m), 3.91-4.00 (1H, m), 4.14 (2H, t, J = 8.6 Hz), 6.57 (1H, d, J = 8.5 Hz), 6.82 (1H, d, J = 2.2 Hz), 6.93-7.00 (1H, m), 7.57 (1H, d, J = 2.2 Hz). |
| 98 | 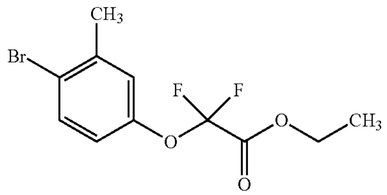 | 3 | NMR2: 1.38 (3H, t, J = 7.1 Hz), 2.34-2.42 (3H, m), 4.39 (2H, q, J = 7.1 Hz), 6.89-6.97 (1H, m), 7.08-7.14 (1H, m), 7.50 (1H, d, J = 8.7 Hz). |
| 99 | 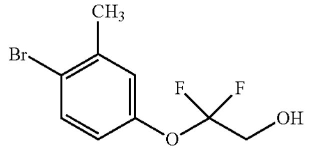 | 4 | NMR2: 2.11 (1H, t, J = 7.4 Hz), 2.39 (3H, s), 3.95-4.01 (2H, m), 6.88-6.96 (1H, m), 7.06-7.12 (1H, m), 7.49 (1H, d, J = 8.6 Hz). |
| 100 | 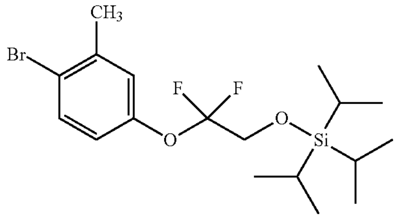 | 5 | NMR2: 0.84-1.37 (21H, m), 2.38 (3H, s), 4.07 (2H, t, J = 8.9 Hz), 6.87-6.95 (1H, m), 7.06-7.11 (1H, m), 7.47 (1H, d, J = 8.6 Hz). |
| 101 | 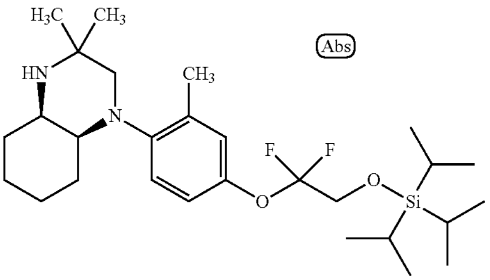 | 2 | NMR2: 0.96-1.23 (24H, m), 1.24-1.49 (7H, m), 1.55-1.74 (4H, m), 1.81-1.92 (1H, m), 2.32 (3H, s), 2.39 (1H, d, J = 11.1 Hz), 2.80-2.90 (1H, m), 3.09 (1H, d, J = 11.1 Hz), 3.48-3.54 (1H, m), 4.06 (2H, t, J = 8.8 Hz), 6.81 (1H, d, J = 8.6 Hz), 6.94 (1H, dd, J = 8.5, 3.0 Hz), 7.01 (1H, d, J = 3.0 Hz). |
| 102 | 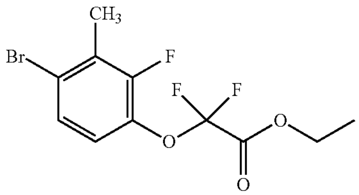 | 3 | NMR2: 1.40 (3H, t, J = 7.2 Hz), 2.30-2.39 (3H, m), 4.42 (2H, q, J = 7.2 Hz), 7.01-7.10 (1H, m), 7.33 (1H, dd, J = 8.8, 2.0 Hz). |
| 103 | 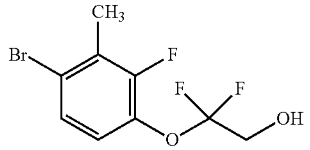 | 4 | NMR2: 2.17 (1H, t, J = 7.5 Hz), 2.33-2.38 (3H, m), 3.99-4.09 (2H, m), 7.01-7.11 (1H, m), 7.32 (1H, dd, J = 8.8, 2.0 Hz). |

TABLE 1-13-continued
| REX | STR | RProp | DATA |
|---|---|---|---|
| 104 | 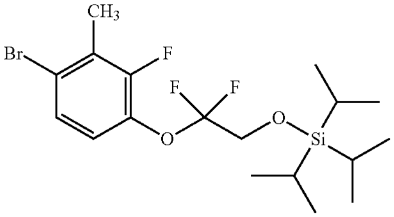 | 5 | NMR2: 1.00-1.23 (21H, m), 2.32-2.37 (3H, m), 4.14 (2H, t, J = 9.1 Hz), 7.05 (1H, t, J = 8.5 Hz), 7.29 (1H, dd, J = 8.5, 2.0 Hz). |
TABLE 1-14
| REX | STR | RProp | DATA |
|---|---|---|---|
| 105 | 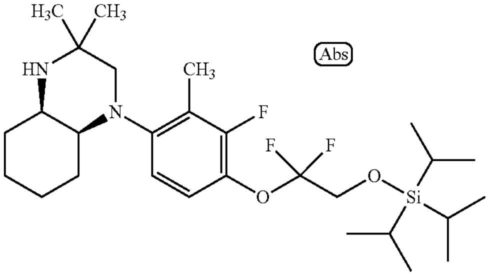 | 2 | NMR2: 0.94-1.26 (25H, m), 1.30 (3H, s), 1.31-1.46 (3H, m), 1.53-1.67 (4H, m), 1.77-1.92 (1H, m), 2.22-2.27 (3H, m), 2.40 (1H, d, J = 11.0 Hz), 2.81-2.91 (1H, m), 3.08 (1H, d, J = 11.0 Hz), 3.50-3.55 (1H, m), 4.13 (2H, t, J = 9.1 Hz), 6.59 (1H, dd, J = 8.8, 1.8 Hz), 7.03 (1H, t, J = 8.8 Hz). |
| 106 | 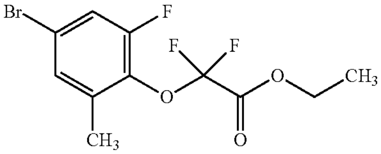 | 3 | NMR2: 1.41 (3H, t, J = 7.1 Hz), 2.33 (3H, s), 4.43 (2H, q, J = 7.1 Hz), 7.14-7.22 (2H, m). |
| 107 | 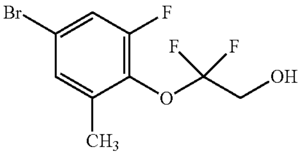 | 4 | NMR2: 2.09-2.17 (1H, m), 2.31 (3H, t, J = 0.9 Hz), 4.08 (2H, td, J = 7.5, 8.9 Hz), 7.13-7.21 (2H, m). |
| 108 | 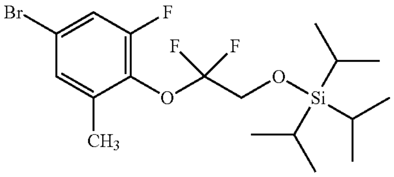 | 5 | NMR2: 1.03-1.22 (21H, m), 2.30 (3H, s), 4.17 (2H, t, J = 8.8 Hz), 7.11-7.18 (2H, m). |
| 109 | 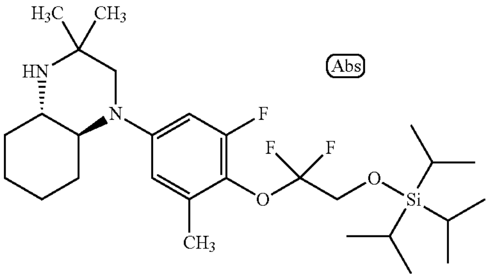 | 2 | NMR2: 0.98-1.43 (32H, m), 1.51-1.78 (4H, m), 2.16-2.24 (1H, m), 2.28 (3H, s), 2.57 (1H, d, J = 11.3 Hz), 2.69-2.83 (2H, m), 4.16 (2H, t, J = 8.8 Hz), 6.65-6.74 (2H, m). |

TABLE 1-14-continued
| REX | STR | RProp | DATA |
| --- | --- | --- | --- |
| 110 | 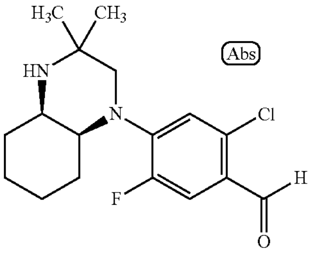 | 110 | NMR2: 1.18 (3H, s), 1.23-1.32 (6H, m), 1.39-1.49 (2H, m), 1.62-1.71 (2H, m), 1.73-1.85 (1H, m), 1.95-2.09 (1H, m), 3.00-3.04 (2H, m), 3.44-3.51 (1H, m), 3.64-3.74 (1H, m), 6.75 (1H, d, J = 7.5 Hz), 7.53 (1H, d, J = 14.1 Hz), 10.16-10.22 (1H, m). |
| 111 | 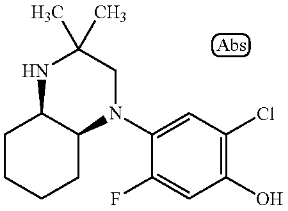 | 111 | NMR1: 0.81-0.91 (1H, m), 0.93-1.10 (4H, m), 1.11-1.27 (4H, m), 1.38-1.64 (4H, m), 1.70-1.97 (2H, m), 2.35 (1H, d, J = 11.1 Hz), 2.88 (1H, d, J = 11.1 Hz), 3.09-3.17 (1H, m), 3.33-3.38 (1H, m), 6.69 (1H, d, J = 13.6 Hz), 6.81 (1H, d, J = 9.2 Hz), 10.21 (1H, brs). |
| 112 | 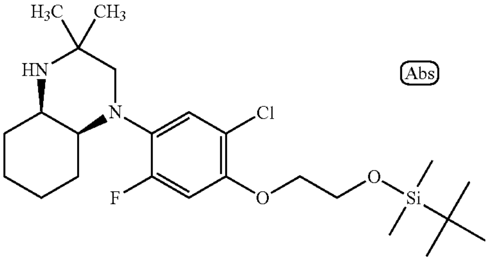 | 112 | NMR2: 0.10 (6H, s), 0.90 (9H, s), 1.04-1.18 (5H, m), 1.24-1.40 (5H, m), 1.59-1.88 (5H, m), 2.50 (1H, d, J = 11.2 Hz), 2.92 (1H, d, J = 11.2 Hz), 3.25-3.34 (1H, m), 3.49-3.54 (1H, m), 3.94-4.08 (4H, m), 6.72 (1H, d, J = 13.6 Hz), 6.84 (1H, d, J = 8.9 Hz). |
TABLE 1-15
| REX | STR | RProp | DATA |
| --- | --- | --- | --- |
| 113 | 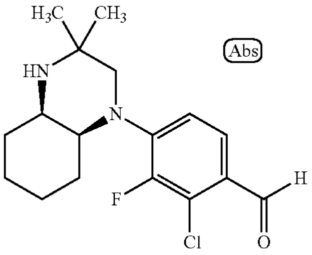 | 110 | NMR2: 1.18 (3H, s), 1.21-1.35 (6H, m), 1.38-1.45 (2H, m), 1.62-1.71 (2H, m), 1.73-1.81 (1H, m), 1.97-2.12 (1H, m), 2.98-3.11 (2H, m), 3.46-3.53 (1H, m), 3.61-3.71 (1H, m), 6.74-6.83 (1H, m), 7.62 (1H, dd, J = 8.8, 1.6 Hz), 10.23 (1H, s). |
| 114 | 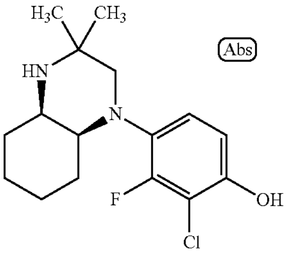 | 111 | NMR1: 0.84-0.91 (1H, m), 0.97-1.12 (4H, m), 1.13-1.30 (4H, m), 1.33-1.67 (5H, m), 1.84-1.98 (1H, m), 2.34 (1H, d, J = 11.0 Hz), 2.93 (1H, d, J = 11.0 Hz), 3.05-3.14 (1H, m), 3.35-3.40 (1H, m), 6.66 (1H, dd, J = 9.0, 1.6 Hz), 6.74 (1H, t, J = 9.0 Hz), 10.18 (1H, brs). |

TABLE 1-15-continued
| REX | STR | RProp | DATA |
|---|---|---|---|
| 115 | 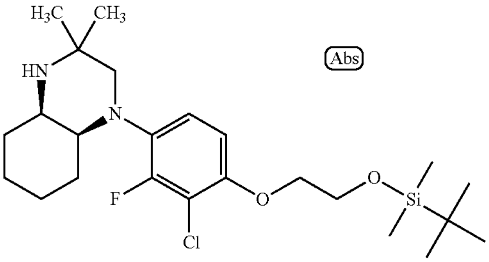 | 112 | NMR2: 0.11 (6H, s), 0.90 (9H, s), 1.03-1.14 (2H, m), 1.16 (3H, s), 1.29 (3H, s), 1.31-1.49 (2H, m), 1.56-1.71 (4H, m), 1.76-1.89 (1H, m), 2.50 (1H, d, J = 11.2 Hz), 2.97 (1H, d, J = 11.2 Hz), 3.24-3.34 (1H, m), 3.51-3.56 (1H, m), 3.95-4.10 (4H, m), 6.60-6.73 (2H, m). |
| 116 | 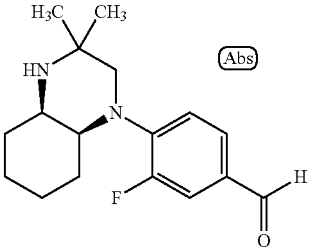 | 110 | NMR2: 1.18 (3H, s), 1.21-1.32 (6H, m), 1.37-1.45 (2H, m), 1.64-1.72 (2H, m), 1.72-1.80 (1H, m), 1.94-2.08 (1H, m), 2.96-3.09 (2H, m), 3.47-3.54 (1H, m), 3.64-3.73 (1H, m), 6.89 (1H, t, J = 8.4 Hz), 7.44-7.55 (2H, m), 9.75-9.80 (1H, m). |
| 117 | 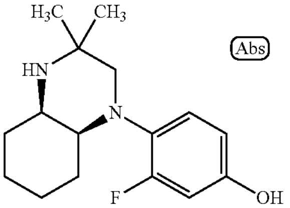 | 111 | NMR1: 0.83-0.91 (1H, m), 0.92-1.09 (4H, m), 1.11-1.26 (4H, m), 1.31-1.66 (5H, m), 1.82-1.96 (1H, m), 2.32 (1H, d, J = 11.0 Hz), 2.91 (1H, d, J = 11.0 Hz), 3.04-3.14 (1H, m), 3.34-3.39 (1H, m), 6.37-6.53 (2H, m), 6.69-6.78 (1H, m), 9.33 (1H, s). |
| 118 | 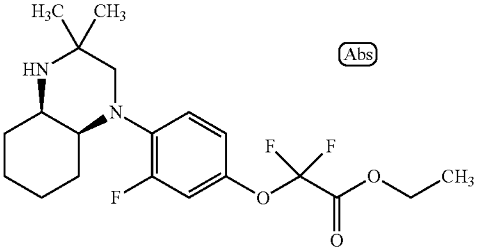 | 118 | NMR2: 1.04-1.22 (5H, m), 1.28 (3H, s), 1.33-1.43 (5H, m), 1.55-1.75 (4H, m), 1.79-1.93 (1H, m), 2.61 (1H, d, J = 11.4 Hz), 2.97 (1H, d, J = 11.4 Hz), 3.36-3.46 (1H, m), 3.51-3.56 (1H, m), 4.39 (2H, q, J = 7.1 Hz), 6.75-6.84 (1H, m), 6.86-6.96 (2H, m). |
| 119 | 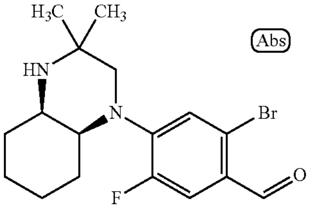 | 110 | NMR2: 1.19 (3H, s), 1.21-1.34 (6H, m), 1.40-1.45 (2H, m), 1.64-1.71 (2H, m), 1.72-1.81 (1H, m), 1.95-2.09 (1H, m), 2.99-3.04 (2H, m), 3.45-3.52 (1H, m), 3.64-3.74 (1H, m), 6.94 (1H, d, J = 7.6 Hz), 7.53 (1H, d, J = 14.2 Hz), 10.04-10.10 (1H, m). |
TABLE 1-16
| REX | STR | RProp | DATA |
|---|---|---|---|
| 120 | 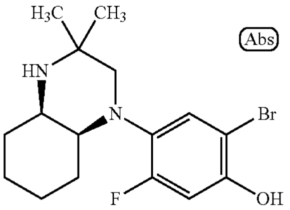 | 111 | NMR1: 0.80-0.91 (1H, m), 0.96-1.10 (4H, m), 1.15-1.27 (4H, m), 1.35-1.66 (5H, m), 1.82-1.96 (1H, m), 2.36 (1H, d, J = 11.0 Hz), 2.89 (1H, d, J = 11.0 Hz), 3.09-3.19 (1H, m), 3.24-3.33 (1H, m), 6.70 (1H, d, J = 13.7 Hz), 6.96 (1H, d, J = 9.3 Hz), 10.08 (1H, brs). |

TABLE 1-16-continued
| REX | STR | RProp | DATA |
|---|---|---|---|
| 121 | 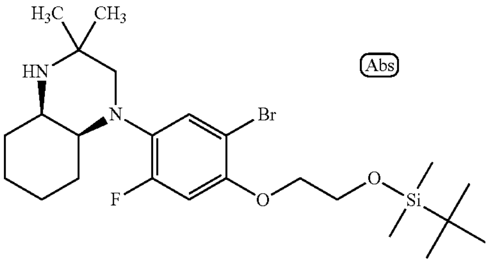 | 112 | NMR2: 0.11 (6H, s), 0.90 (9H, s), 1.04-1.14 (2H, m), 1.16 (3H, s), 1.22-1.41 (5H, m), 1.54-1.73 (4H, m), 1.74-1.88 (1H, m), 2.50 (1H, d, J = 11.1 Hz), 2.92 (1H, d, J = 11.2 Hz), 3.24-3.33 (1H, m), 3.48-3.54 (1H, m), 3.94-4.07 (4H, m), 6.71 (1H, d, J = 13.7 Hz), 7.00 (1H, d, J = 9.1 Hz). |
| 122 | 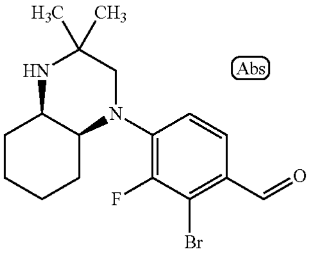 | 110 | NMR2: 1.18 (3H, s), 1.21-1.34 (6H, m), 1.39-1.47 (2H, m), 1.62-1.71 (2H, m), 1.73-1.81 (1H, m), 1.97-2.12 (1H, m), 2.97-3.12 (2H, m), 3.46-3.53 (1H, m), 3.61-3.70 (1H, m), 6.78-6.87 (1H, m), 7.63 (1H, dd, J = 8.8, 1.5 Hz), 10.12-10.17 (1H, m). |
| 123 | 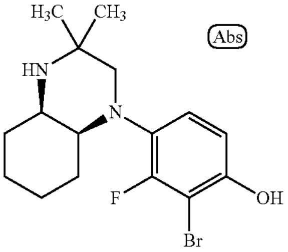 | 111 | NMR1: 0.83-0.91 (1H, m), 0.96-1.09 (4H, m), 1.12-1.26 (4H, m), 1.32-1.67 (5H, m), 1.86-1.98 (1H, m), 2.34 (1H, d, J = 11.0 Hz), 2.94 (1H, d, J = 11.0 Hz), 3.04-3.14 (1H, m), 3.35-3.40 (1H, m), 6.66 (1H, dd, J = 9.0, 1.8 Hz), 6.79 (1H, t, J = 9.0 Hz), 10.13 (1H, brs). |
| 124 | 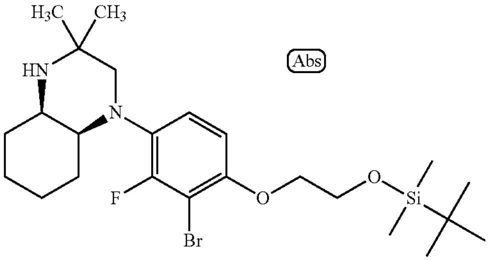 | 112 | NMR2: 0.11 (6H, s), 0.90 (9H, s), 1.02-1.20 (5H, m), 1.24-1.41 (5H, m), 1.56-1.71 (4H, m), 1.76-1.90 (1H, m), 2.50 (1H, d, J = 11.2 Hz), 2.97 (1H, d, J = 11.2 Hz), 3.24-3.33 (1H, m), 3.50-3.56 (1H, m), 3.95-4.08 (4H, m), 6.62 (1H, dd, J = 9.0, 1.8 Hz), 6.75 (1H, t, J = 9.0 Hz). |
| 125 | 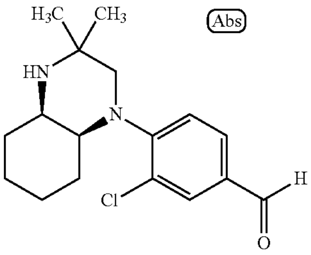 | 110 | NMR2: 0.99-1.08 (1H, m), 1.09-1.20 (4H, m), 1.20-1.31 (4H, m), 1.35-1.45 (2H, m), 1.63-1.74 (3H, m), 1.90-2.07 (1H, m), 2.64 (1H, d, J = 11.2 Hz), 3.17 (1H, d, J = 11.2 Hz), 3.57-3.63 (1H, m), 3.66-3.77 (1H, m), 6.99 (1H, d, J = 8.3 Hz), 7.67 (1H, dd, J = 8.3, 2.0 Hz), 7.84 (1H, d, J = 2.0 Hz), 9.83 (1H, s). |
| 126 | 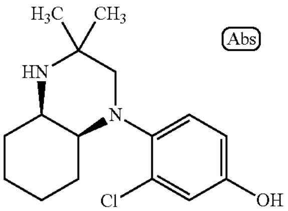 | 111 | NMR1: 0.81-0.89 (1H, m), 0.91-1.02 (1H, m), 1.06 (3H, s), 1.18-1.30 (4H, m), 1.36-1.66 (5H, m), 1.84-1.99 (1H, m), 2.20 (1H, d, J = 10.7 Hz), 2.96-3.07 (2H, m), 3.37-3.43 (1H, m), 6.64 (1H, dd, J = 8.6, 2.8 Hz), 6.77 (1H, d, J = 2.8 Hz), 6.84 (1H, d, J = 8.6 Hz), 9.42 (1H, s). |

TABLE 1-17
| REX | STR | RProp | DATA |
|---|---|---|---|
| 127 | 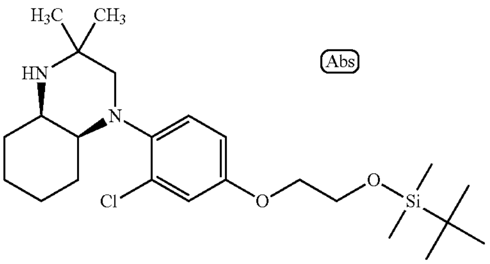 | 112 | NMR2: 0.09 (6H, s), 0.90 (9H, s), 1.02-1.11 (2H, m), 1.15 (3H, s), 1.25-1.44 (5H, m), 1.58-1.73 (4H, m), 1.78-1.89 (1H, m), 2.38 (1H, d, J = 11.0 Hz), 3.06 (1H, d, J = 11.0 Hz), 3.19-3.26 (1H, m), 3.51-3.59 (1H, m), 3.90-4.00 (4H, m), 6.73 (1H, dd, J = 8.7, 2.9 Hz), 6.83 (1H, d, J = 8.7 Hz), 6.95 (1H, d, J = 2.9 Hz). |
| 128 | 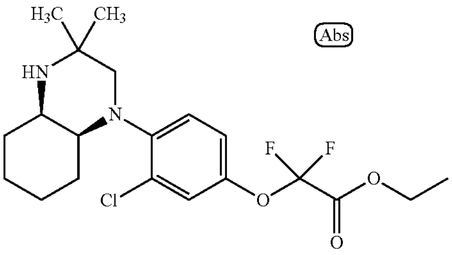 | 118 | NMR2: 0.97-1.10 (2H, m), 1.16 (3H, s), 1.31 (3H, s), 1.34-1.45 (5H, m), 1.58-1.73 (4H, m), 1.80-1.94 (1H, m), 2.42 (1H, d, J = 10,9 Hz), 3.08 (1H, d, J = 10.9 Hz), 3.34-3.41 (1H, m), 3.54-3.61 (1H, m), 4.39 (2H, q, J = 7.2 Hz), 6.85-6.90 (1H, m), 7.00-7.08 (1H, m), 7.23-7.26 (1H, m). |
| 129 | 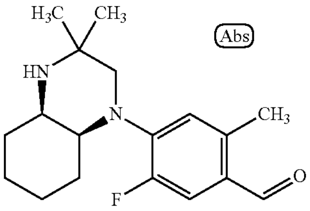 | 110 | NMR2: 1.18 (3H, s), 1.20-1.32 (5H, m), 1.37-1.46 (2H, m), 1.54-1.59 (1H, m), 1.63-1.71 (2H, m), 1.71-1.79 (1H, m), 1.95-2.07 (1H, m), 2.57 (3H, t, J = 0.8 Hz), 2.94-3.06 (2H, m), 3.47-3.53 (1H, m), 3.65-3.73 (1H, m), 6.58 (1H, d, J = 8.4 Hz), 7.41 (1H, d, J = 14.3 Hz), 10.01-10.06 (1H, m). |
| 130 | 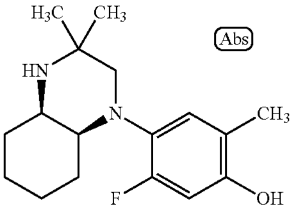 | 111 | NMR1: 0.81-0.91 (1H, m), 0.93-1.11 (4H, m), 1.15-1.27 (4H, m), 1.28-1.65 (5H, m), 1.82-1.95 (1H, m), 2.03 (3H, s), 2.33 (1H, d, J = 11.0 Hz), 2.91 (1H, d, J = 11.0 Hz), 3.04-3.13 (1H, m), 3.32-3.39 (1H, m), 6.49 (1H, d, J = 13.8 Hz), 6.62 (1H, d, J = 10.0 Hz), 9.22 (1H, brs). |
| 131 | 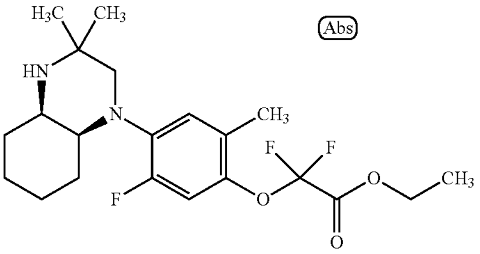 | 118 | NMR2: 1.04-1.21 (5H, m), 1.28 (3H, s), 1.34-1.42 (5H, m), 1.56-1.76 (4H, m), 1.77-1.92 (1H, m), 2.21 (3H, s), 2.60 (1H, d, J = 11.3 Hz), 2.95 (1H, d, J = 11.3 Hz), 3.36-3.46 (1H, m), 3.50-3.55 (1H, m), 4.40 (2H, q, J = 7.2 Hz), 6.64 (1H, d, J = 9.5 Hz), 6.91 (1H, d, J = 12.8 Hz). |
| 132 | 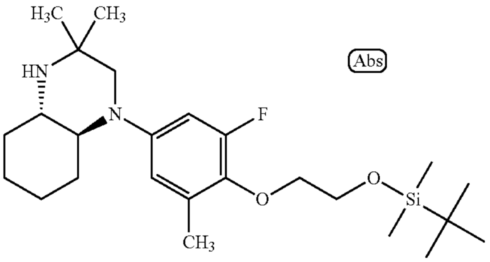 | 2 | NMR2: 0.08 (6H, s), 0.76-1.11 (14H, m), 1.15-1.41 (6H, m), 1.56-1.77 (4H, m), 2.10-2.22 (1H, m), 2.26 (3H, s), 2.53 (1H, d, J = 11.2 Hz), 2.67-2.78 (2H, m), 3.90 (2H, t, J = 5.1 Hz), 4.02-4.09 (2H, m), 6.61-6.70 (2H, m). |

TABLE 1-17-continued
| REX | STR | RProp | DATA |
|---|---|---|---|
| 133 | 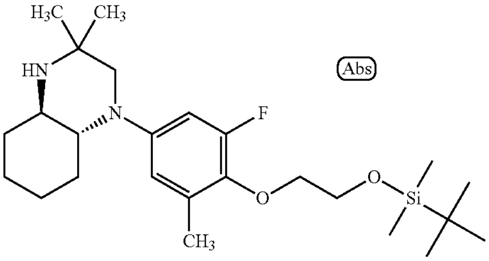 | 2 | NMR2: 0.08 (6H, s), 0.76-1.11 (14H, m), 1.15-1.41 (6H, m), 1.56-1.77 (4H, m), 2.10-2.22 (1H, m), 2.26 (3H, s), 2.53 (1H, d, J = 11.2 Hz), 2.67-2.78 (2H, m), 3.90 (2H, t, J = 5.1 Hz), 4.02-4.09 (2H, m), 6.61-6.70 (2H, m). |
TABLE 1-18
| REX | STR | RProp | DATA |
|---|---|---|---|
| 134 | 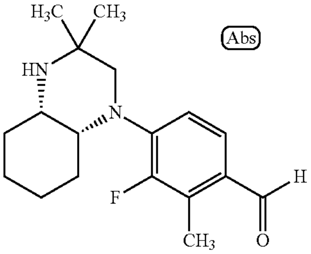 | 110 | NMR2: 1.18 (3H, s), 1.22-1.30 (6H, m), 1.39-1.46 (2H, m), 1.63-1.79 (3H, m), 1.93-2.07 (1H, m), 2.53-2.58 (3H, m), 2.95 (1H, d, J = 12.0 Hz), 3.04 (1H, d, J = 12.0 Hz), 3.47-3.54 (1H, m), 3.61-3.71 (1H, m), 6.76 (1H, t, J = 8.5 Hz), 7.46 (1H, dd, J = 8.5, 1.2 Hz), 9.99-10.04 (1H, m). |
| 135 | 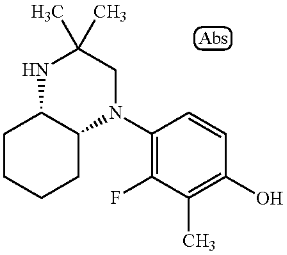 | 111 | NMR1: 0.82-0.90 (1H, m), 0.92-1.11 (4H, m), 1.14-1.28 (4H, m), 1.36-1.65 (5H, m), 1.82-1.95 (1H, m), 1.96-2.05 (3H, m), 2.29 (1H, d, J = 11.0 Hz), 2.91 (1H, d, J = 11.0 Hz), 3.06-3.11 (1H, m), 3.34-3.40 (1H, m), 6.48 (1H, d, J = 9.0 Hz), 6.56 (1H, t, J = 9.0 Hz), 9.20 (1H, brs). |
| 136 | 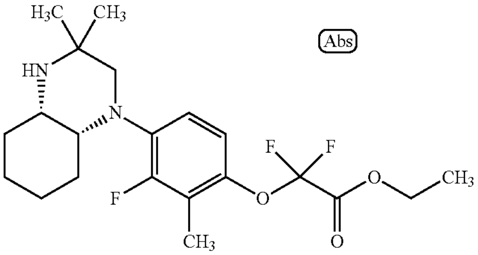 | 118 | NMR2: 1.03-1.20 (5H, m), 1.28 (3H, s), 1.34-1.42 (5H, m), 1.56-1.75 (4H, m), 1.78-1.92 (1H, m), 2.13-2.22 (3H, m), 2.58 (1H, d, J = 11.3 Hz), 2.97 (1H, d, J = 11.3 Hz), 3.35-3.44 (1H, m), 3.51-3.56 (1H, m), 4.39 (2H, q, J = 7.2 Hz), 6.65 (1H, t, J = 9.2 Hz), 6.89-6.91 (1H, m). |
| 137 | 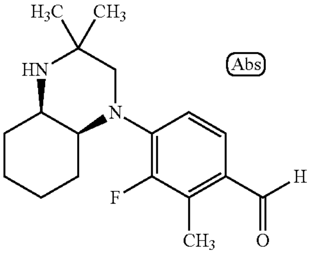 | 110 | NMR2: 1.18 (3H, s), 1.21-1.32 (5H, m), 1.36-1.46 (3H, m), 1.63-1.71 (2H, m), 1.71-1.79 (1H, m), 1.96-2.07 (1H, m), 2.51-2.60 (3H, m), 2.95 (1H, d, J = 12.0 Hz), 3.04 (1H, d, J = 12.0 Hz), 3.48-3.54 (1H, m), 3.62-3.70 (1H, m), 6.76 (1H, t, J = 8.4 Hz), 7.43-7.50 (1H, m), 9.99-10.04 (1H, m). |

TABLE 1-18-continued
| REX | STR | RProp | DATA |
|---|---|---|---|
| 138 | 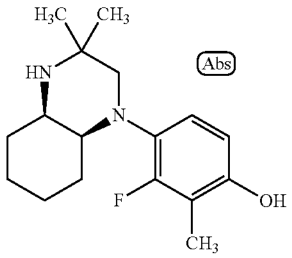 | 111 | NMR1: 0.82-0.90 (1H, m), 0.92-1.09 (4H, m), 1.12-1.28 (4H, m), 1.32-1.64 (5H, m), 1.82-1.96 (1H, m), 1.97-2.02 (3H, m), 2.29 (1H, d, J = 11.0 Hz), 2.91 (1H, d, J = 11.0 Hz), 3.04-3.13 (1H, m), 3.35-3.40 (1H, m), 6.49 (1H, dd, J = 9.0, 1.2 Hz), 6.56 (1H, t, J = 9.0 Hz), 9.22 (1H, brs). |
| 139 | 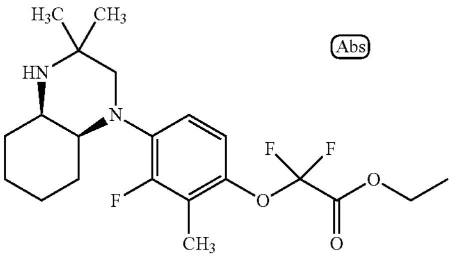 | 118 | NMR2: 1.03-1.19 (5H, m), 1.28 (3H, s), 1.34-1.42 (5H, m), 1.56-1.76 (4H, m), 1.78-1.92 (1H, m), 2.17-2.22 (3H, m), 2.58 (1H, d, J = 11.3 Hz), 2.97 (1H, d, J = 11.3 Hz), 3.35-3.44 (1H, m), 3.51-3.56 (1H, m), 4.39 (2H, q, J = 7.1 Hz), 6.65 (1H, t. J = 9.0 Hz), 6.90 (1H, d, J = 9.0 Hz). |
| 140 | 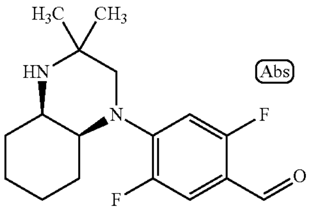 | 110 | NMR2: 1.18 (3H, s), 1.23-1.35 (6H, m), 1.41-1.48 (2H, m), 1.62-1.71 (2H, m), 1.74-1.82 (1H, m), 1.95-2.10 (1H, m), 3.00 (1H, d, J = 12.3 Hz), 3.06 (1H, d, J = 12.3 Hz), 3.44-3.51 (1H, m), 3.64-3.74 (1H, m), 6.48 (1H, dd, J = 12.3, 7.5 Hz), 7.43 (1H, dd, J = 13.1, 7.4 Hz), 10.06-10.11 (1H, m). |
TABLE 1-19
| REX | STR | RProp | DATA |
|---|---|---|---|
| 141 | 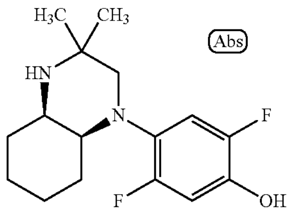 | 111 | NMR1: 0.79-0.91 (1H, m), 0.93-1.09 (4H, m), 1.12-1.26 (4H, m), 1.32-1.71 (5H, m), 1.82-1.96 (1H, m), 2.36 (1H, d, J = 11.1 Hz), 2.86 (1H, d, J = 11.1 Hz), 3.11-3.21 (1H, m), 3.32-3.41 (1H, m), 6.66-6.74 (2H, m), 9.68 (1H, brs). |
| 142 | 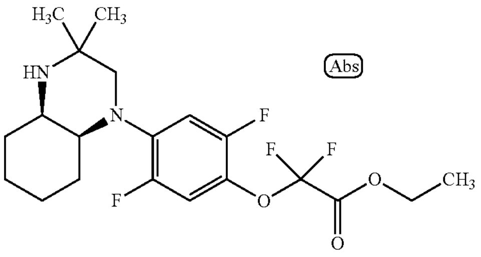 | 118 | NMR2: 1.07-1.22 (5H, m), 1.27 (3H, s), 1.36-1.44 (5H, m), 1.56-1.78 (4H, m), 1.81-1.94 (1H, m), 2.63 (1H, d, J = 11.4 Hz), 2.91 (1H, d, J = 11.4 Hz), 3.41-3.58 (2H, m), 4.41 (2H, q, J = 7.1 Hz), 6.62 (1H, dd, J = 12.0, 7.9 Hz), 6.98 (1H, dd, J = 12.5, 7.2 Hz). |

TABLE 1-19-continued
| REX | STR | RProp | DATA |
|---|---|---|---|
| 143 | 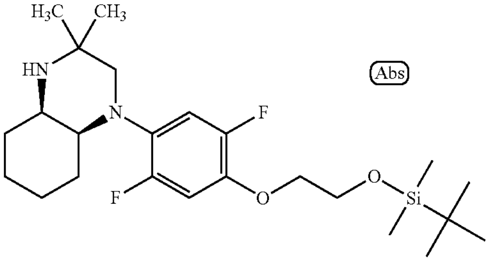 | 112 | NMR2: 0.09 (6H, s), 0.90 (9H, s), 0.99-1.18 (5H, m), 1.22-1.44 (5H, m), 1.52-1.90 (5H, m), 2.51 (1H, d, J = 11.2 Hz), 2.89 (1H, d, J = 11.2 Hz), 3.27-3.37 (1H, m), 3.48-3.54 (1H, m), 3.88-4.13 (4H, m), 6.61 (1H, dd, J = 12.9, 8.2 Hz), 6.73 (1H, dd, J = 13.3, 7.9 Hz) |
| 144 | 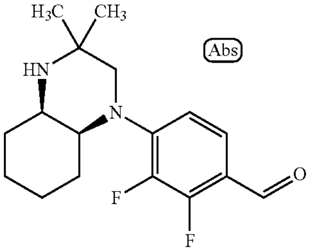 | 110 | NMR2: 1.18 (3H, s), 1.22-1.35 (6H, m), 1.39-1.46 (2H, m), 1.64-1.70 (2H, m), 1.74-1.82 (1H, m), 1.98-2.10 (1H, m), 2.99-3.13 (2H, m), 3.45-3.51 (1H, m), 3.64-3.72 (1H, m), 6.59-6.68 (1H, m), 7.44-7.53 (1H, m), 10.10(1H, s). |
| 145 | 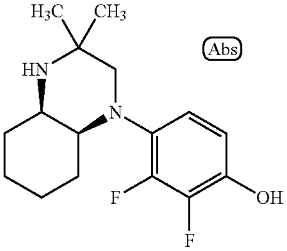 | 111 | NMR1: 0.82-0.93 (1H, m), 0.96-1.09 (4H, m), 1.14-1.27 (4H, m), 1.32-1.67 (5H, m), 1.80-1.97 (1H, m), 2.36 (1H, d, J = 11.1 Hz), 2.90 (1H, d, J = 11.1 Hz), 3.08-3.17 (1H, m), 3.36-3.41 (1H, m), 6.42-6.68 (2H, m), 9.72 (1H, brs) |
| 146 | 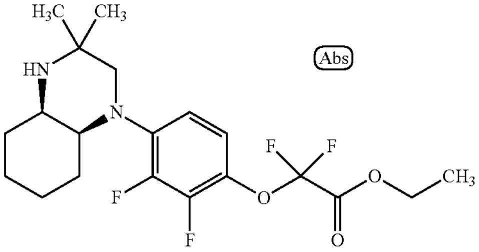 | 118 | NMR2: 1.08-1.21 (5H, m), 1.28 (3H, s), 1.34-1.45 (5H, m), 1.58-1.79 (4H, m), 1.82-1.97 (1H, m), 2.66 (1H, d, J = 11.5 Hz), 2.97 (1H, d, J = 11.5 Hz), 3.40-3.49 (1H, m), 3.50-3.56 (1H, m), 4.42 (2H, q, J = 7.2 Hz), 6.50-6.59 (1H, m), 6.89-6.98 (1H, m). |
| 147 | 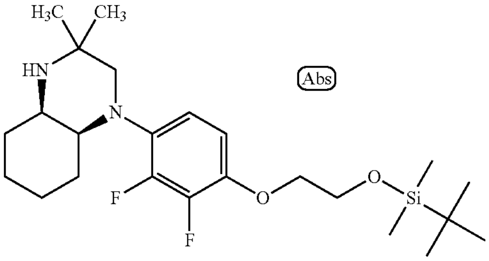 | 112 | NMR2: 0.09 (6H, s), 0.90 (9H, s), 1.01-1.18 (5H, m), 1.25-1.45 (5H, m), 1.55-1.91 (5H, m), 2.52 (1H, d, J = 11.2 Hz), 2.94 (1H, d, J = 11.2 Hz), 3.27-3.36 (1H, m), 3.50-3.57 (1H, m), 3.91-4.10 (4H, m), 6.48 (1H, td, J = 9.0, 2.4 Hz), 6.63 (1H, td, J = 9.0, 2.2 Hz). |

TABLE 1-20

| REX | STR | RProp | DATA |
|---|---|---|---|
| 148 | 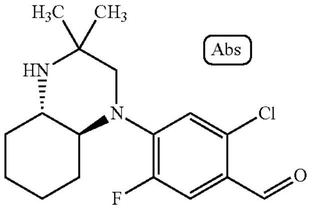 | 110 | NMR2: 1.00-1.13 (4H, m), 1.22-1.45 (7H, m), 1.69-1.80 (3H, m), 1.85-1.93 (1H, m), 2.51-2.61 (1H, m), 2.66 (1H, d, J = 11.5 Hz), 2.79-2.89 (1H, m), 2.97 (1H, d, J = 11.5 Hz), 7.04 (1H, d, J = 6.9 Hz), 7.58 (1H, d, J = 11.3 Hz), 10.27-10.33 (1H, m). |
| 149 | 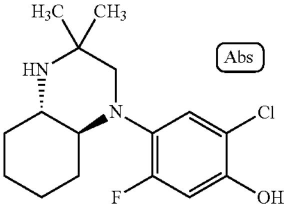 | 111 | NMR1: 0.83-1.01 (4H, m), 1.08-1.30 (7H, m), 1.36-1.47 (1H, m), 1.52-1.65 (3H, m), 2.18-2.34 (1H, m), 2.51-2.64 (3H, m), 6.70 (1H, d, J = 12.1 Hz), 7.13 (1H, d, J = 8.4 Hz) The Hydrogen of —OH could not be detected. |
| 150 | 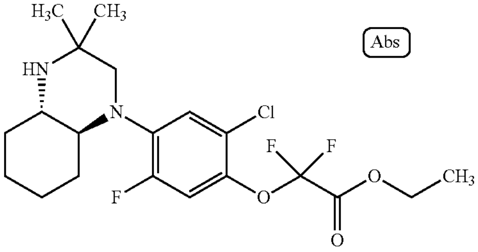 | 118 | NMR2: 1.02-1.17 (1H, m), 1.21-1.44 (8H, m), 1.57-1.86 (8H, m), 2.12-2.29 (1H, m), 2.96-3.31 (4H, m), 4.43 (2H, q, J = 7.1 Hz), 7.11 (1H, d, J = 10.4 Hz), 7.25-7.30 (1H, m). |
| 151 | 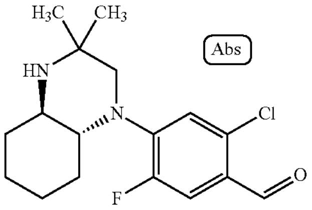 | 110 | NMR2: 1.00-1.13 (4H, m), 1.21-1.46 (7H, m), 1.67-1.81 (3H, m), 1.85-1.93 (1H, m), 2.51-2.61 (1H, m), 2.65 (1H, d, J = 11.5 Hz), 2.78-2.88 (1H, m), 2.97 (1H, d, J = 11.5 Hz), 7.04 (1H, d, J = 6.8 Hz), 7.57 (1H, d, J = 11.3 Hz), 10.27-10.32 (1H, m) |
| 152 | 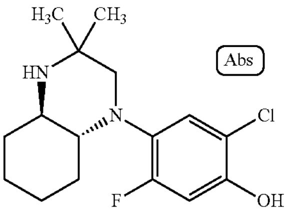 | 111 | NMR1: 0.81-0.98 (4H, m), 1.00-1.30 (7H, m), 1.38-1.49 (1H, m), 1.53-1.67 (3H, m), 2.19-2.31 (1H, m), 2.53-2.69 (3H, m), 6.71 (1H, d, J = 12.0 Hz), 7.13 (1H, d, J = 8.4 Hz) The hydrogen of —OH could not be detected. |
| 153 | 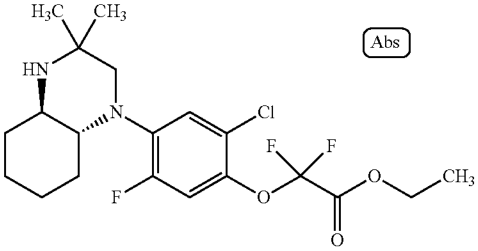 | 118 | NMR2: 1.01-1.13 (1H, m), 1.26 (3H, s), 1.28-1.43 (5H, m), 1.50 (3H, s), 1.57-1.79 (5H, m), 1.83-1.99 (1H, m), 2.54-3.05 (4H, m), 4.42 (2H, q, J = 7.1 Hz), 7.09 (1H, d, J = 10.7 Hz), 7.21 (1H, d, J = 7.9 Hz). |
| 154 | 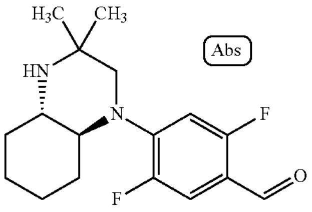 | 110 | NMR2: 0.98-1.18 (4H, m), 1.22-1.47 (7H, m), 1.67-1.86 (3H, m), 1.90-1.98 (1H, m), 2.60-2.64 (1H, m), 2.70 (1H, d, J = 11.7 Hz), 2.82-2.93 (1H, m), 3.00 (1H, d, J = 11.7 Hz), 6.79 (1H, dd, J = 11.5, 6.2 Hz), 7.49 (1H, dd, J = 11.0, 6.4 Hz), 10.18-10.23 (1H, m). |

TABLE 1-20-continued
| REX | STR | RProp | DATA |
|---|---|---|---|
| 155 | 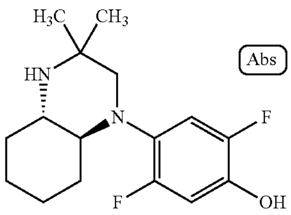 | 111 | NMR1: 0.83-1.01 (4H, m), 1.01-1.35 (7H, m), 1.37-1.48 (1H, m), 1.51-1.67 (3H, m), 2.15-2.28 (1H, m), 2.51-2.64 (3H, m), 6.68 (1H, dd, J = 11.8, 8.3 Hz), 6.99 (1H, dd, J = 12.2, 7.8 Hz), 10.05 (1H, brs). |
TABLE 1-21
| REX | STR | RProp | DATA |
|---|---|---|---|
| 156 | 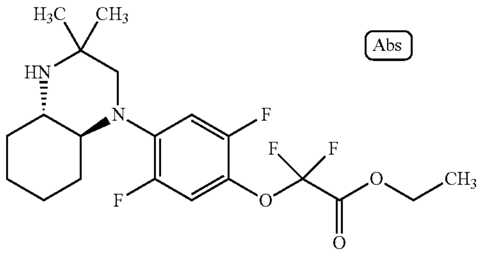 | 118 | NMR: 2 1.01-1.14 (1H, m), 1.21-1.43 (8H, m), 1.54-1.77 (8H, m), 1.87-1.98 (1H, m), 2.52-3.03 (4H, m), 4.42 (2H, q, J = 7.1 Hz), 6.93-7.01 (2H, m). |
| 157 | 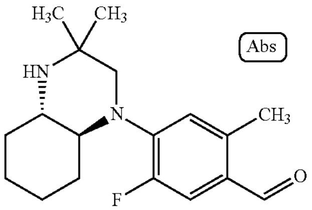 | 110 | NMR2: 0.96-1.10 (4H, m), 1.19-1.46 (7H, m), 1.66-1.79 (3H, m), 1.80-1.88 (1H, m), 2.46-2.68 (5H, m), 2.76-2.87 (1H, m), 2.91 (1H, d, J = 11.4 Hz), 6.88 (1H, d, J = 7.5 Hz), 7.46 (1H, d, J = 11.4 Hz), 10.12-10.16 (1H, m). |
| 158 | 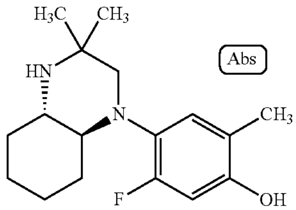 | 111 | NMR1: 0.79-0.96 (4H, m), 1.01-1.31 (7H, m), 1.32-1.46 (1H, m), 1.47-1.64 (3H, m), 2.03 (3H, s), 2.15-2.29 (1H, m), 2.50-2.65 (3H, m), 6.48 (1H, d, J = 12.5 Hz), 6.87 (1H, d, J = 9.3 Hz), 9.48 (1H, brs). |
| 159 | 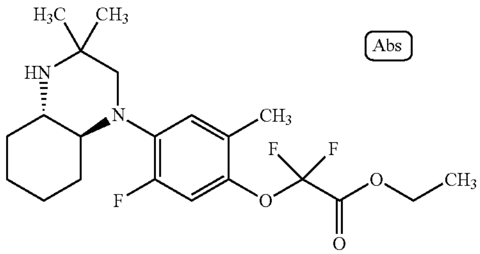 | 118 | NMR2: 0.99-1.14 (1H, m), 1.21-1.44 (8H, m), 1.65-2.02 (8H, m), 2.17-2.39 (4H, m), 3.00-3.47 (4H, m), 4.41 (2H, q, J = 7.1 Hz), 6.97 (1H, d, J = 10.6 Hz), 7.05 (1H, d, J = 8.5 Hz). |
| 160 | 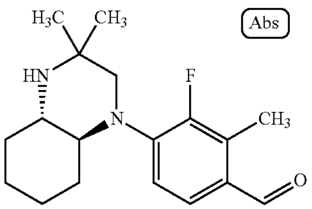 | 110 | NMR2: 0.97-1.10 (4H, m), 1.21-1.45 (7H, m), 1.65-1.79 (3H, m), 1.82-1.89 (1H, m), 2.47-2.65 (5H, m), 2.78-2.88 (1H, m), 2.92 (1H, d, J = 11.4 Hz), 7.03 (1H, t, J = 8.0 Hz), 7.53 (1H, dd, J = 8.0, 1.3 Hz), 10.11-10.16 (1H, m) |

TABLE 1-21-continued

| REX | STR | RProp | DATA |
|---|---|---|---|
| 161 | 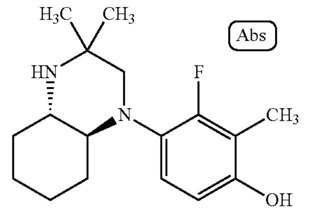 | 111 | NMR2: 0.89-1.12 (4H, m), 1.17-1.44 (7H, m), 1.53-1.75 (4H, m), 2.13 (3H, s), 2.20-2.50 (2H, m), 2.56-2.87 (3H, m), 6.49 (1H, d, J = 8.5 Hz), 6.78-6.88 (1H, m). |
| 162 | 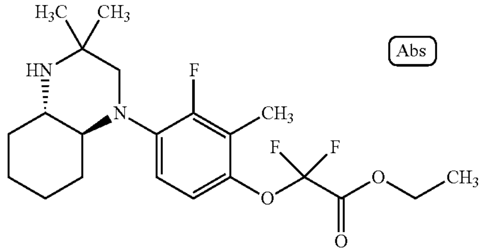 | 118 | NMR2: 0.97-1.12 (1H, m), 1.19-1.42 (8H, m), 1.64-2.03 (8H, m), 2.14-2.37 (4H, m), 3.01-3.59 (4H, m), 4.41 (2H, q, J = 7.1 Hz), 6.95-7.07 (2H, m). |
| 163 | 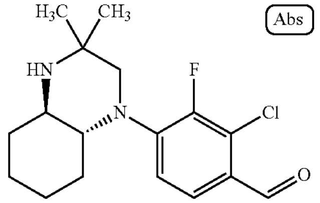 | 110 | NMR2: 0.95-1.12 (4H, m), 1.24-1.45 (7H, m), 1.67-1.79 (3H, m), 1.79-1.87 (1H, m), 2.53-2.68 (2H, m), 2.79-2.89 (1H, m), 2.95 (1H, d, J = 11.5 Hz), 7.01-7.10 (1H, m), 7.64-7.71 (1H, m), 10.32-10.37 (1H, m). |

TABLE 1-22

| REX | STR | RProp | DATA |
|---|---|---|---|
| 164 | 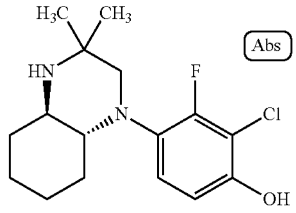 | 111 | NMR1: 0.84-1.05 (4H, m), 1.10-1.33 (7H, m), 1.36-1.48 (1H, m), 1.53-1.66 (3H, m), 2.28-2.37 (1H, m), 2.53-2.69 (3H, m), 6.69-6.76 (1H, m), 6.92-7.13 (1H, m) The hydrogen of —OH could not be detected. |
| 165 | 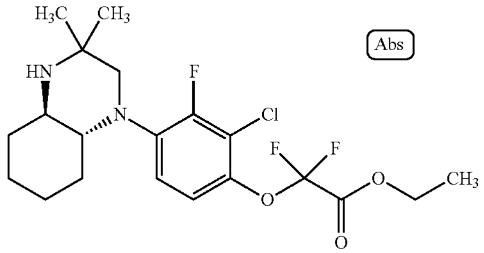 | 118 | NMR2: 1.04-1.13 (1H, m), 1.21-1.44 (8H, m), 1.64-1.94 (8H, m), 2.14-2.33 (1H, m), 3.00-3.36 (4H, m), 4.43 (2H, q, J = 7.2 Hz), 7.09-7.15 (2H, m). |

Example 1. Synthesis of 2-(2,6-difluoro-4-((4a'S, 8a'S)-hexahydro-1'H-spiro[cyclobutane-1,2'-quinoxaline]-4'(3'H)-yl)phenoxy)ethan-1-ol To a solution of (4a'S,8a'S)-4'-(4-(4-(2-((tert-butyldimethylsilyl)oxy)ethoxy)-3,5-difluorophenyl)octahydro-1'H-spiro[cyclobutane-1,2'-quinoxaline] (480 mg) in THF (6 mL) was added 1M-TBAF/THF solution (1029 μL) with stirring at room temperature. The reaction mixture was stirred at room temperature overnight and then concentrated. After that, the residue was purified by basic silica gel column chromatography (Hexane/AcOEt). The purified product was recrystallized from Hexane/AcOEt to obtain the object compound (312 mg).

Example 2. Synthesis of 2,2-difluoro-2-(4-((4a'S,8a'S)-hexahydro-1'H-spiro[cyclobutane-1,2'-quinoxaline]-4'(3'H)-yl)phenoxy)ethan-1-ol To a solution of (4a'S,8a'S)-4'-(4-(1,1-difluoro-2-((triisopropylsilyl)oxy)ethoxy)phenyl)octahydro-1'H-spiro[cyclobutane-1,2'-quinoxaline] (670 mg) in THF (6 mL) was added 1M-TBAF/THF solution (1317 μL) with stirring at room temperature. The reaction mixture was stirred at room temperature overnight and then concentrated under reduced pressure. After that, the residue was purified by basic silica gel column chromatography (Hexane/AcOEt). The purified product was recrystallized from AcOEt/Hexane to obtain the object compound (436 mg).

Example 17. Synthesis of 2-(2-chloro-6-fluoro-4-((3R,4aS,8aS)-3-methyloctahydroquinoxalin-1(2H)-yl)phenoxy)ethan-1-ol 1/2fumarate To a solution of (3R,4aS,8aS)-1-(3-chloro-5-fluoro-4-(2-((triisopropylsilyl)oxy)ethoxy)phenyl)-3-methyldecahydroquinoxaline (650 mg) in THF (5 mL) was added 1M-TBAF/THF solution (1302 μL), and the mixture was stirred at room temperature overnight. The reaction mixture was concentrated under reduced pressure, and the residue was then purified by basic silica gel column chromatography (Hexane/AcOEt). The purified product was dissolved in EtOH, thereto was added a solution of fumaric acid (156 mg) in EtOH, and the mixture was concentrated. The precipitated crystal was recrystallized from EtOH/AcOEt to obtain the object compound (420 mg).

Example 20. Synthesis of 2-(4-((4aS,8aS)-3,3-dimethyloctahydroquinoxalin-1(2H)-yl)phenoxy)-2,2-difluoroethan-1-ol To a solution of (4aS,8aS)-1-(4-(1,1-difluoro-2-((triisopropylsilyl)oxy)ethoxy)phenyl)-3,3-dimethyldecahydroquinoxaline (540 mg) in THF (5 mL) was added 1M-TBAF/THF solution (2.17 mL), and the mixture was stirred at room temperature for 1 hour. The reaction mixture was concentrated, and the residue was then purified by basic silica gel column chromatography (Hexane/AcOEt). The resulting product was recrystallized from AcOEt/Hexane to obtain the object compound (324 mg).

Example 22. Synthesis of 2-(4-((4aS,8aS)-3,3-dimethyloctahydroquinoxalin-1(2H)-yl)-2-fluorophenoxy)-2,2-difluoroethan-1-ol To a solution of (4aS,8aS)-1-(4-(1,1-difluoro-2-((triisopropylsilyl)oxy)ethoxy)-3-fluorophenyl)-3,3-dimethyldecahydroquinoxaline (560 mg) in THF (5 mL) was added 1M-TBAF/THF solution (2.18 mL), and the mixture was stirred at room temperature for 1 hour. The reaction mixture was concentrated, and the residue was then purified by basic silica gel column chromatography (Hexane/AcOEt). The resulting product was recrystallized from AcOEt/Hexane to obtain the object compound (347 mg).

Example 27. Synthesis of 2-(2-chloro-4-((4aS,8aS)-3,3-dimethyloctahydroquinoxalin-1(2H)-yl)phenoxy)ethan-1-ol To a solution of (4aS,8aS)-1-(3-chloro-4-(2-((triisopropylsilyl)oxy)ethoxy)phenyl)-3,3-dimethyldecahydroquinoxaline (1.95 g) in THF (20 mL) was added 1M-TBAF/THF solution (3.94 mL), and the mixture was stirred at room temperature for 1 hour. The reaction mixture was concentrated under reduced pressure, and the residue was then purified by basic silica gel column chromatography (Hexane/AcOEt). The resulting product was recrystallized from AcOEt/Hexane to obtain the object compound (1.33 g).

Example 34. Synthesis of 2-(4-((4aS,8aS)-3,3-dimethyloctahydroquinoxalin-1(2H)-yl)-2,6-difluorophenoxy)ethan-1-ol To a solution of (4aS,8aS)-1-(3,5-difluoro-4-(2-((triisopropylsilyl)oxy)ethoxy)phenyl)-3,3-dimethyldecahydroquinoxaline (500 mg) in THF (5 mL) was added 1M-TBAF/THF solution (2.01 mL), and the mixture was stirred at room temperature for 1 hour. The reaction mixture was concentrated, and the residue was then purified by basic silica gel column chromatography (Hexane/AcOEt). The resulting product was recrystallized from AcOEt/Hexane to obtain the object compound (281 mg).

Example 37. Synthesis of 2,2-difluoro-2-(4-((4aS,8aS)-3,3,4-trimethyloctahydroquinoxalin-1(2H)-yl)phenoxy)ethan-1-ol To a solution of (4aS,8aS)-4-(4-(1,1-difluoro-2-((triisopropylsilyll)oxy)ethoxy)phenyl)-1,2,2-trimethyldecahydroquinoxaline (480 mg) in THF (6 mL) was added 1M-TBAF/THF solution (940 μL) was added, and the mixture was stirred at room temperature for 1 hour. The reaction mixture was concentrated, and the residue was then purified by basic silica gel column chromatography (Hexane/AcOEt). The obtained solid was recrystallized from AcOEt/Hexane to obtain the object compound (296 mg).

Example 38. Synthesis of 2-(2-chloro-4-((4aS,8aS)-3,3,4-trimethyloctahydroquinoxalin-1(2H)-ylphenoxy)ethan-1-ol 2hydrochloride To a solution of (4aS,8aS)-4-(3-chloro-4-(2-((triisopropylsilyll)oxy)ethoxy)phenyl)-1,2,2-trimethyldecahydroquinoxaline (410 mg) in THF (6 mL) was added 1M-TBAF/THF solution (805 μL), and the mixture was stirred at room temperature for 1 hour. The reaction mixture was concentrated, and the residue was then purified by basic silica gel column chromatography (Hexane/AcOEt). The purification product was dissolved in EtOH, thereto was added 1N—HCl/EtOH, and the mixture was concentrated. The resulting product was recrystallized from EtOH/AcOEt to obtain the object compound (285 mg).

Example 44. Synthesis of 2-(2-chloro-4-((4aR,8aS)-3,3-dimethyloctahydroquinoxalin-1(2H)-yl)phenoxy)ethan-1-ol 1/2fumarate To a solution of (4aR,8aS)-1-(3-chloro-4-(2-((triisopropylsilyl)oxy)ethoxy)phenyl)-3,3-dimethyldecahydroquinoxaline (3.60 g) in THF (50 mL) was added 1M-TBAF/THF solution (7.27 mL), and the mixture was stirred at room temperature for 1 hour. The reaction mixture was concentrated, and the residue was then purified by basic silica gel column chromatography (Hexane/AcOEt). The purified product was dissolved in AcOEt/EtOH, thereto was added a solution of fumaric acid (0.43 g) in EtOH, and the mixture was concentrated. The resulting product was recrystallized from EtOH to obtain the object compound (2.5 g).

Example 47. Synthesis of 2-(2-chloro-4-((4aR,8aS)-3,3,4-trimethyloctahydroquinoxalin-1(2H)-yl)phenoxy)ethan-1-ol fumarate To a solution of (4aS,8aR)-4-(3-chloro-4-(2-((triisopropylsilyl)oxy)ethoxy)phenyl)-1,2,2-trimethyldecahydroquinoxaline (160 mg) in THF (4 mL) was added 1M-TBAF/THF solution (314 μL), and the mixture was stirred at room temperature for 1.5 hours. The reaction mixture was concentrated, and the residue was then purified by basic silica gel column chromatography (Hexane/AcOEt). The purified product was dissolved in AcOEt/EtOH, thereto was added a solution of fumaric acid (40 mg) in EtOH, and the mixture was concentrated. The resulting product was washed by dispersing it into DCM/Hexane to obtain the object compound (95 mg).

Example 56. Synthesis of 2-(4-((4aR,8aS)-3,3-dimethyloctahydroquinoxalin-1(2H)-yl)-3-methylphenoxy)-2,2-difluoroethan-1-ol To a solution of (4aR,8aS)-1-(4-(1,1-difluoro-2-((triisopropylsilyl)oxy)ethoxy)-2-methylphenyl)-3,3-dimethyldecahydroquinoxaline (290 mg) in THF (5 mL) was added 1M-TBAF/THF solution (568 μL), and the mixture was stirred at room temperature for 1 hour. The reaction mixture was concentrated, and the residue was then purified by basic silica gel column chromatography (Hexane/AcOEt). The resulting product was recrystallized from Hexane to obtain the object compound (130 mg).

Example 59. Synthesis of 2-(2-chloro-4-((4aR,8aS)-3,3-dimethyloctahydroquinoxalin-1(2H)-yl)-5-fluorophenoxy)ethan-1-ol 3/4fumarate To a solution of (4aR,8aS)-1-(4-(2-((tert-butyldimethylsilyl)oxy)ethoxy)-5-chloro-2-fluorophenyl)-3,3-dimethyldecahydroquinoxaline (200 mg) in THF (3 mL) was added 1M-TBAF/THF solution (425 μL), and the mixture was stirred at room temperature for 1 hour. The reaction mixture was concentrated, and the residue was then purified by basic silica gel column chromatography (Hexane/AcOEt). The purified product was dissolved in AcOEt/EtOH, thereto was added a solution of fumaric acid (54 mg) in EtOH, and the mixture was concentrated. The resulting product was recrystallized from EtOH/AcOEt to obtain the object compound (160 mg).

Example 60. Synthesis of 2-(2-chloro-4-((4aR,8aS)-3,3-dimethyloctahydroquinoxalin-1(2H)-yl)-3-fluorophenoxy)ethan-1-ol fumarate To a solution of (4aR,8aS)-1-(4-(4-(2-((tert-butyldimethylsilyl)oxy)ethoxy)-3-chloro-2-fluorophenyl)-3,3-dimethyldecahydroquinoxaline (195 mg) in THF (3 mL) was added 1M-TBAF/THF solution (414 μL), and the mixture was stirred at room temperature for 1 hour. The reaction mixture was concentrated, and the residue was purified by basic silica gel column chromatography (Hexane/AcOEt). The purified product was dissolved in EtOH, thereto was added a solution of fumaric acid (53.7 mg) in EtOH, and the mixture was concentrated. The resulting product was recrystallized from EtOH/AcOEt to obtain the object compound (150 mg).

Example 61. Synthesis of 2-(4-((4aR,8aS)-3,3-dimethyloctahydroquinoxalin-1(2H)-yl)-3-fluorophenoxy)-2,2-difluoroethan-1-ol 1/2fumarate To a solution of ethyl 2-(4-((4aR,8aS)-3,3-dimethyloctahydroquinoxalin-1(2H)-yl)-3-fluorophenoxy)-2,2-difluoroacetate (165 mg) in THF (5 mL) was added $LiBH_4$ (19.75 mg) with stirring under ice-cooling, and the mixture was stirred at room temperature for 20 hours. To the reaction mixture was added 5N—HCl/MeOH with stirring under ice-cooling until no foaming was occurred. After that, the reaction mixture was basified by adding 5N NaOH aq., and the mixture was extracted with AcOEt. The organic layer was concentrated, and the residue was then purified by basic silica gel column chromatography. The purified product was dissolved in AcOEt/EtOH, thereto was added a solution of fumaric acid (53 mg) in EtOH, and the mixture was concentrated. The resulting product was recrystallized from EtOH/AcOEt to obtain the object compound (120 mg).

Example 64. Synthesis of 2-(3-chloro-4-((4aR,8aS)-3,3-dimethyloctahydroquinoxalin-1(2H)-yl)phenoxy)ethan-1-ol 1/2fumarate To a solution of (4aR,8aS)-1-(4-(4-(2-((tert-butyldimethylsilyl)oxy)ethoxy)-2-chlorophenyl)-3,3-dimethyldecahydroquinoxaline (540 mg) in THF (8 mL) was added 1M-TBAF/THF solution (1192 μL), and the mixture was stirred at room temperature for 1 hour. The reaction mixture was concentrated under reduced pressure, and the residue was purified by basic silica gel column chromatography (Hexane/AcOEt). The purified product was dissolved in EtOH, thereto was added a solution of fumaric acid (94 mg) in EtOH, and the mixture was concentrated. The resulting product was recrystallized from EtOH/AcOEt to obtain the object compound (400 mg).

Example 69. Synthesis of 2-(4-((4aS,8aR)-3,3-dimethyloctahydroquinoxalin-1(2H)-yl)-3-fluoro-2-methylphenoxy)-2,2-difluoroethan-1-ol 1/2fumarate To a solution of ethyl 2-(4-((4aS,8aR)-3,3-dimethyloctahydroquinoxalin-1(2H)-yl)-3-fluoro-2-methylphenoxy)-2,2-difluoroacetate (460 mg) in THF (12 mL) was added $LiBH_4$ (53.2 mg) with stirring under ice-cooling, and the mixture was stirred at room temperature for 17 hours. To the reaction mixture was added 5N HCl/MeOH to quench the reaction, and then the mixture was neutralized by adding 5N NaOH aq. The product was extracted with AcOEt, and the organic layer was then concentrated. The residue was purified by basic silica gel column chromatography (Hexane/AcOEt). The purified product was dissolved in EtOH, thereto was added a solution of fumaric acid (70 mg) in EtOH, and the mixture was concentrated under reduced pressure. The resulting product was recrystallized from EtOH/AcOEt to obtain the object compound (340 mg).

Example 74. Synthesis of 2-(4-((4aR,8aS)-3,3-dimethyloctahydroquinoxalin-1(2H)-yl)-2,3-difluorophenoxy)ethan-1-ol 1/2fumarate To a solution of (4aR,8aS)-1-(4-(2-((tert-butyldimethylsilyl)oxy)ethoxy)-2,3-difluorophenyl)-3,3-dimethyldecahydroquinoxaline (440 mg) in THF (6 mL) was added 1M-TBAF/THF solution (968 μL), and the mixture was stirred at room temperature for 1 hour. The reaction mixture was concentrated, and the residue was then purified by basic silica gel column chromatography (Hexane/AcOEt). The purified product was dissolved in EtOH, thereto was added a solution of fumaric acid (124 mg) in EtOH, and the mixture was concentrated. The resulting product was recrystallized from EtOH/AcOEt to obtain the object compound (330 mg).

The compounds of Examples 3-16, 18-19, 21, 23-26, 28-33, 35-36, 39-43, 45-46, 48-55, 57-58, 62-63, 65-68, 70-73 and 75-80 were manufactured in the same manner as in Examples 1, 2, 17, 20, 22, 27, 34, 37, 38, 44, 47, 56, 59-61, 64, 69 and 74. Structural formulae and physicochemical data of the compounds of Examples 1 to 80 are shown in Tables 2-1 to 2-12.

TABLE 2-1

| EX | STR | Prop | DATA |
|---|---|---|---|
| 1 | 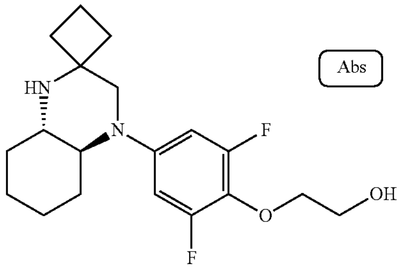 | 1 | NMR2: 0.89-1.04 (1H, m), 1.15-1.91 (13H, m), 2.21-2.36 (2H, m), 2.37-2.47 (1H, m), 2.50-2.60 (1H, m), 2.65 (1H, dd, J = 1.5, 11.1 Hz), 3.06 (1H, d, J = 11.0 Hz), 3.84-3.91 (2H, m), 4.17-4.23 (2H, m), 6.64-6.74 (2H, m). |
| 2 | 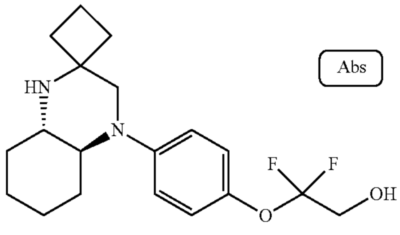 | 2 | NMR2: 0.84-1.03 (1H, m), 1.11-1.94 (13H, m), 2.13-2.64 (4H, m), 2.72 (1H, dd, J = 1.5, 11.2 Hz), 3.08 (1H, d, J = 11.1 Hz), 3.99 (2H, t, J = 8.8 Hz), 7.06-7.17 (4H, m). |
| 3 | 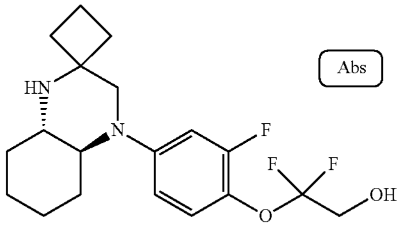 | 1 | NMR2: 0.84-1.04 (1H, m), 1.15-1.41 (3H, m), 1.43-1.95 (10H, m), 2.25-3.22 {total 6 H including 2.29-2.40 (1H, m), 2.40-2.50 (1H, m), 2.50-2.63 (1H, m), 2.70 (1H, dd, J = 1.6, 11.2 Hz), 3.10 (1H, d, J = 11.2 Hz)}, 4.03 (2H, t, J = 9.0 Hz), 6.83-6.90 (1H, m), 6.90-6.97 (1H, m), 7.17-7.25 (1H, m). |
| 4 | 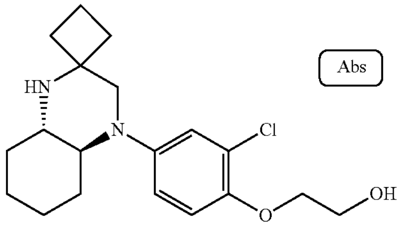 | 1 | NMR2: 0.87-1.03 (1H, m), 1.11-1.94 (13H, m), 2.24-2.60 (4H, m), 2.69 (1H, dd, J = 1.4, 11.0 Hz), 3.03 (1H, d, J = 11.0 Hz), 3.91-4.03 (2H, m), 4.08-4.17 (2H, m), 6.89 (1H, d, J = 8.7 Hz), 7.00 (1H, dd, J = 2.5, 8.7 Hz), 7.17 (1H, d, J = 2.5 Hz). |
| 5 | 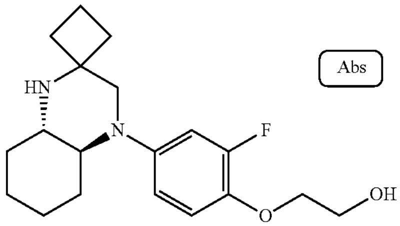 | 1 | NMR2: 0.88-1.02 (1H, m), 1.11-1.93 (13H, m), 2.09-2.41 (2H, m), 2.41-2.62 (2H, m), 2.67 (1H, dd, J = 1.4, 11.2 Hz), 3.04 (1H, d, J = 11.0 Hz), 3.89-4.02 (2H, m), 4.09-4.18 (2H, m), 6.81-6.87 (1H, m), 6.87-6.96 (2H, m). |

TABLE 2-1-continued

| EX | STR | Prop | DATA |
|---|---|---|---|
| 6 | 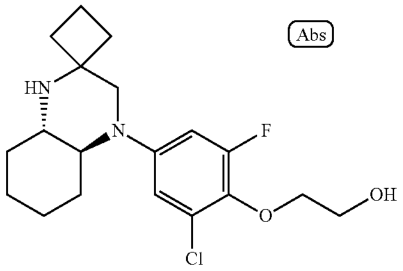 | 1 | NMR2: 0.89-1.04 (1H, m), 1.14-1.92 (13H, m), 2.28 (1H, ddd, J = 3.3, 8.7, 11.4 Hz), 2.34-2.48 (2H, m), 2.50-2.59 (1H, m), 2.66 (1H, dd, J = 1.5, 11.1 Hz), 3.06 (1H, d, J = 11.0 Hz), 3.86-3.93 (2H, m), 4.17-4.23 (2H, m), 6.82 (1H, dd, J = 2.5, 12.0 Hz), 6.91-6.97 (1H, m). |
| 7 | 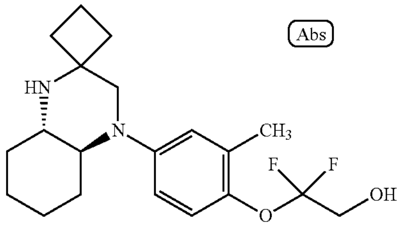 | 1 | NMR2: 0.83-1.04 (1H, m), 1.12-3.30 (total 22H including 1.12-1.44 (3H, m), 1.54-1.93 (10H, m), 2.24 (3H, s), 2.32-2.42 (1H, m), 2.43-2.62 (2H, m), 2.72 (1H, d, J = 11.2 Hz), 3.07 (1H, d, J = 11.2 Hz)}, 3.94-4.08 (2H, m), 6.89-6.99 (2H, m), 7.14 (1H, d, J = 8.4 Hz). |

TABLE 2-2

| EX | STR | Prop | DATA |
|---|---|---|---|
| 8 | 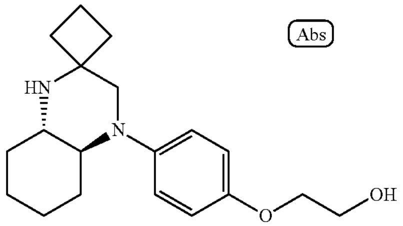 | 1 | NMR2: 0.86-1.02 (1H, m), 1.11-1.92 (13H, m), 2.12 (1H, brs), 2.29-2.38 (1H, m), 2.43-2.61 (2H, m), 2.71 (1H, dd, J = 1.6, 11.0 Hz), 3.03 (1H, d, J = 11.1 Hz), 3.91-3.99 (2H, m), 4.03-4.10 (2H, m), 6.82-6.90 (2H, m), 7.03-7.12 (2H, m). |
| 9 | 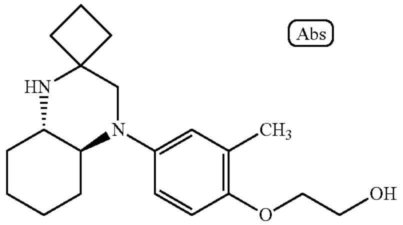 | 1 | NMR2: 0.85-1.03 (1H, m), 1.12-1.93 (13H, m), 2.07 (1H, brs), 2.22 (3H, s), 2.28-2.38 (1H, m), 2.44-2.61 (2H, m), 2.70 (1H, dd, J = 1.7, 11.1 Hz), 3.03 (1H, d, J = 11.0 Hz), 3.92-4.02 (2H, m), 4.03-4.10 (2H, m), 6.76 (1H, d, J = 8.3 Hz), 6.89-6.97 (2H, m). |
| 10 | 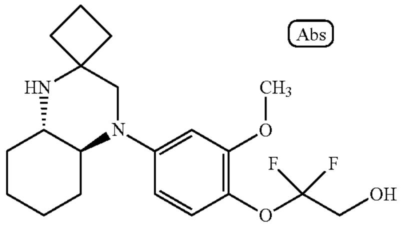 | 1 | NMR2: 0.90-1.06 (1H, m), 1.12-1.96 (13H, m), 2.30-2.41 (1H, m), 2.41-2.53 (1H, m), 2.53-2.64 (1H, m), 2.73 (1H, d, J = 11.0 Hz), 2.84-3.56 {total 2H, including 3.09 (1H, d, J = 11.1 Hz)}, 3.82-3.88 (3H, m), 3.92 (2H, t, J = 8.4 Hz), 6.68-6.80 (2H, m), 7.17 (1H, dd, J = 1.4, 8.5 Hz). |
| 11 | 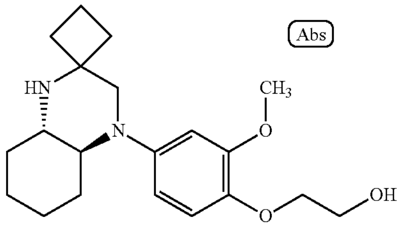 | 1 | NMR2: 0.89-1.04 (1H, m), 1.12-1.52 (4H, m), 1.52-1.94 (9H, m), 2.32 (1H, ddd, J = 3.4, 8.6, 11.6 Hz), 2.43-2.82 (4H, m), 3.06 (1H, d, J = 11.0 Hz), 3.85 (3H, s), 3.90 (2H, brs), 4.07-4.14 (2H, m), 6.67-6.76 (2H, m), 6.88 (1H, d, J = 8.1 Hz). |

TABLE 2-2-continued
| EX | STR | Prop | DATA |
|---|---|---|---|
| 12 | 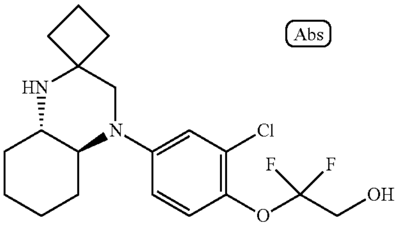 Abs | 1 | NMR2: 0.91-1.04 (1H, m), 1.15-1.92 (13H, m), 2.35 (1H, ddd, J = 3.3, 8.6, 11.6 Hz), 2.39-2.62 (3H, m), 2.71 (1H, dd, J = 1.6, 11.1 Hz), 3.09 (1H, d, J = 11.1 Hz), 4.05 (2H, t, J = 8.9 Hz), 7.01 (1H, dd, J = 2.5, 8.7 Hz), 7.18 (1H, d, J = 2.5 Hz), 7.24-7.30 (1H, m). |
| 13 | 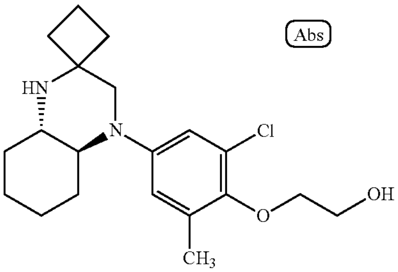 Abs | 1 | NMR2: 0.88-1.03 (1H, m), 1.15-1.93 (13H, m), 2.23-2.61 (7H, m), 2.67 (1H, dd, J = 1.4, 11.0 Hz), 3.04 (1H, d, J = 11.0 Hz), 3.95 (2H, dd, J = 3.6, 5.2 Hz), 4.03 (2H, dd, J = 3.6, 5.2 Hz), 6.82-6.87 (1H, m), 6.99 (1H, d, J = 2.6 Hz). |
| 14 | 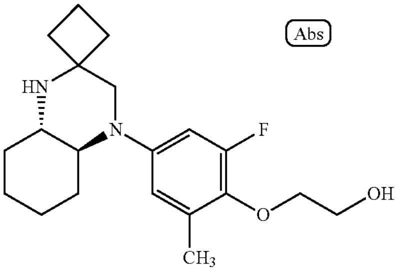 Abs | 1 | NMR2: 0.88-1.02 (1H, m), 1.13-1.91 (13H, m), 2.12-2.35 (5H, m), 2.39-2.60 (2H, m), 2.66 (1H, dd, J = 1.4, 11.2 Hz), 3.05 (1H, d, J = 11.0 Hz), 3.85-3.95 (2H, m), 4.05-4.13 (2H, m), 6.67-6.78 (2H, m). |
TABLE 2-3
| EX | STR | Prop | DATA |
|---|---|---|---|
| 15 | 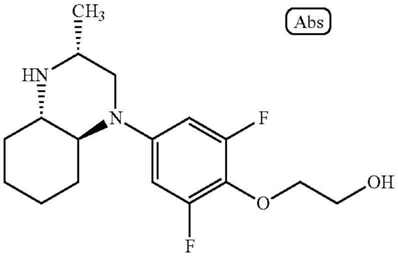 Abs | 1 | NMR2: 0.91-1.09 (4H, m), 1.12-1.43 (4H, m), 1.50-1.81 (4H, m), 2.13-2.36 (2H, m), 2.36-2.45 (1H, m), 2.51-2.61 (1H, m), 2.98 (1H, dd, J = 2.8, 11.1 Hz), 3.03-3.16 (1H, m), 3.84-3.91 (2H, m), 4.20 (2H, dd, J = 3.9, 4.9 Hz), 6.64-6.75 (2H, m). |
| 16 | 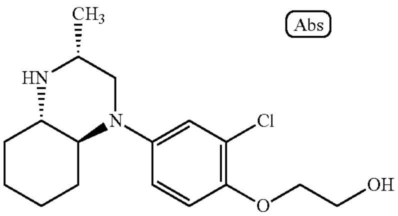 Abs | 1 | NMR2: 0.91-1.09 (4H, m), 1.13-1.81 (8H, m), 2.07-2.33 (2H, m), 2.46 (1H, dd, J = 10.1, 11.1 Hz), 2.57 (1H, ddd, J = 3.7, 8.6, 11.2 Hz), 2.96 (1H, dd, J = 2.8, 11.1 Hz), 3.04-3.16 (1H, m), 3.97 (2H, t, J = 4.5 Hz), 4.12 (2H, dd, J = 3.9, 5.1 Hz), 6.88 (1H, d, J = 8.7 Hz), 7.00 (1H, dd, J = 2.5, 8.7 Hz), 7.18 (1H, d, J = 2.5 Hz). |

TABLE 2-3-continued

| EX | STR | Prop | DATA |
|---|---|---|---|
| 17 | 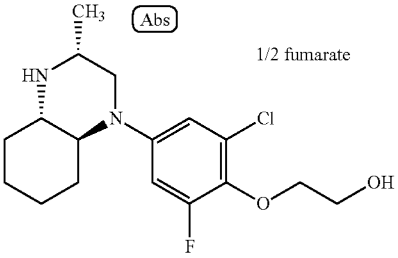 Abs 1/2 fumarate | 17 | NMR1: 0.81-1.11 (4H, m), 1.12-1.37 (3H, m), 1.51-1.86 (4H, m), 2.36-2.63 (3H, m), 2.95-3.14 (2H, m), 3.68 (2H, t, J = 5.2 Hz), 4.01 (2H, t, J = 5.2 Hz), 4.83 (1H, brs), 6.48 (1H, s), 6.99-7.08 (2H, m). Two hydrogens could not be detected. |
| 18 | 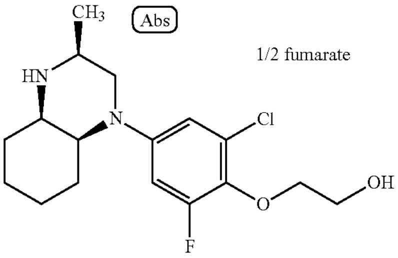 Abs 1/2 fumarate | 17 | NMR1: 0.84-1.10 (4H, m), 1.14-1.37 (3H, m), 1.52-1.62 (2H, m), 1.62-1.71 (1H, m), 1.72-1.84 (1H, m), 2.38-2.65 (3H, m), 3.02 (1H, dd, J = 2.8, 11.3 Hz), 3.04-3.15 (1H, m), 3.68 (2H, t, J = 5.2 Hz), 4.02 (2H, t, J = 5.2 Hz), 4.85 (1H, br), 6.48 (1H, s), 7.00-7.09 (2H, m). Two hydrogens could not be detected. |
| 19 | 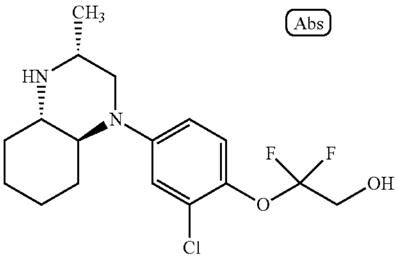 Abs | 1 | NMR2: 0.90-1.10 (4H, m), 1.14-1.83 (8H, m), 2.20-2.67 (total 4H including 2.33 (1H, ddd, J = 3.1, 8.6, 11.4 Hz), 2.47 (1H, dd, J = 10.2, 11.2 Hz), 2.53-2.64 (1H, m)}, 3.01 (1H, dd, J = 2.8, 11.2 Hz), 3.05-3.18 (1H, m), 4.05 (2H, t, J = 8.9 Hz), 7.01 (1H, dd, J = 2.5, 8.8 Hz), 7.19 (1H, d, J = 2.5 Hz), 7.24-7.31 (1H, m). |
| 20 | 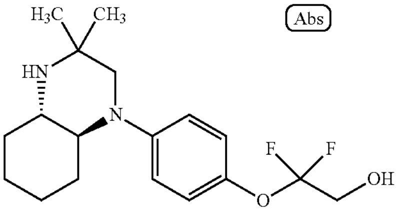 Abs | 20 | NMR1: 0.84-1.03 (4H, m), 1.08-1.36 (6H, m), 1.42-1.69 (5H, m), 2.18-2.29 (1H, m), 2.50-2.56 (1H, m), 2.57-2.71 (2H, m), 3.76-3.89 (2H, m), 5.84 (1H, t, J = 6.6 Hz), 7.02-7.13 (4H, m). |
| 21 | 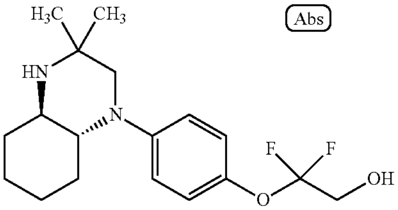 Abs | 1 | NMR1: 0.84-1.03 (4H, m), 1.08-1.36 (6H, m), 1.42-1.69 (5H, m), 2.18-2.29 (1H, m), 2.50-2.56 (1H, m), 2.57-2.71 (2H, m), 3.76-3.89 (2H, m), 5.84 (1H, t, J = 6.6 Hz), 7.02-7.13 (4H, m). |

TABLE 2-4

| EX | STR | Prop | DATA |
|---|---|---|---|
| 22 | 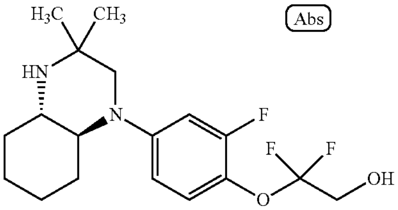 Abs | 22 | NMR1: 0.86-1.05 (4H, m), 1.06-1.37 (6H, m), 1.40-1.75 (5H, m), 2.26-2.37 (1H, m), 2.57-2.69 (2H, m), 2.77 (1H, d, J = 11.2 Hz), 3.78-3.92 (2H, m), 5.91 (1H, t, J = 6.6 Hz), 6.80-6.88 (1H, m), 6.93-7.02 (1H, m), 7.18-7.28 (1H, m). |

TABLE 2-4-continued

| EX | STR | Prop | DATA |
|---|---|---|---|
| 23 | 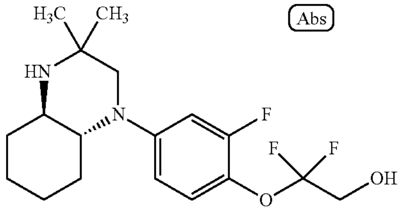 | 1 | NMR1: 0.86-1.05 (4H, m), 1.06-1.37 (6H, m), 1.40-1.75 (5H, m), 2.26-2.37 (1H, m), 2.57-2.69 (2H, m), 2.77 (1H, d, J = 11.2 Hz), 3.78-3.92 (2H, m), 5.91 (1H, t, J = 6.6 Hz), 6.80-6.88 (1H, m), 6.93-7.02 (1H, m), 7.18-7.28 (1H, m). |
| 24 | 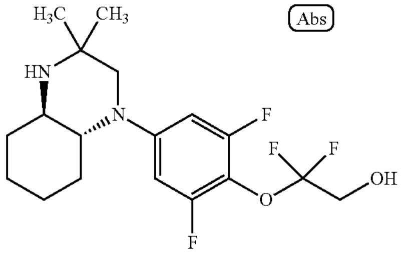 | 1 | NMR2: 0.58-2.46 {total 16H including 0.96-1.12 (4H, m), 1.15-1.43 (6H, m), 1.60-1.91 (4H, m)}, 2.32 (1H, ddd, J = 3.2, 9.1, 11.9 Hz), 2.66 (1H, d, J = 11.7 Hz), 2.76 (1H, ddd, J = 3.1, 9.0, 11.8 Hz), 2.82-2.89 (1H, m), 4.02-4.11 (2H, m), 6.57-6.66 (2H, m). |
| 25 | 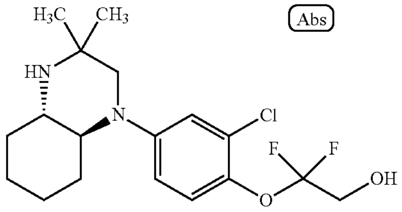 | 1 | NMR2: 0.94-1.12 (4H, m), 1.14-2.16 {total 12H including 1.13-1.42 (6H, m), 1.58-1.83 (4H, m)}, 2.24 (1H, ddd, J = 3.0, 8.8, 11.5 Hz), 2.61 (1H, d, J = 11.3 Hz), 2.71-2.82 (2H, m), 4.05 (2H, t, J = 8.9 Hz), 6.95 (1H, dd, J = 2.5, 8.8 Hz), 7.13 (1H, d, J = 2.5 Hz), 7.22-7.29 (1H, m). |
| 26 | 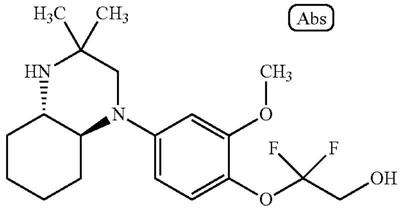 | 1 | NMR2: 0.68-1.44 {total 11 H including 0.94-1.11 (4H, m), 1.15-1.42 (6H, m)}, 1.58-1.80 (4H, m), 2.24 (1H, ddd, J = 3.0, 8.8, 11.5 Hz), 2.62 (1H, d, J = 11.2 Hz), 2.71-2.82 (2H, m), 3.04 (1H, brs), 3.85 (3H, d, J = 1.9 Hz), 3.92 (2H, t, J = 8.4 Hz), 6.64-6.73 (2H, m), 7.12-7.19 (1H, m). |
| 27 | 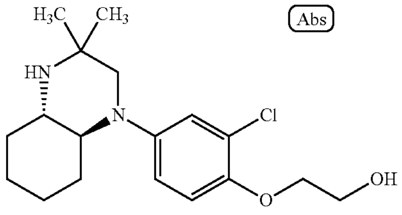 | 27 | NMR1: 0.78-1.03 (4H, m), 1.05-1.34 (6H, m), 1.37-1.70 (5H, m), 2.10-2.20 (1H, m), 2.47-2.54 (1H, m), 2.54-2.68 (2H, m), 3.67-3.77 (2H, m), 4.02 (2H, t, J = 5.1 Hz), 4.85 (1H, t, J = 5.4 Hz), 6.98 (1H, dd, J = 2.5, 8.8 Hz), 7.03-7.10 (2H, m). |
| 28 | 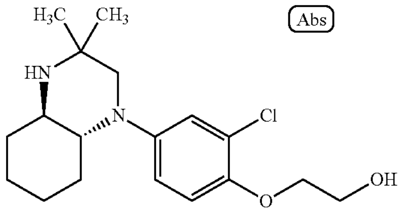 | 1 | NMR1: 0.78-1.03 (4H, m), 1.05-1.34 (6H, m), 1.37-1.70 (5H, m), 2.15 (1H, ddd, J = 3.2, 8.7, 11.5 Hz), 2.47-2.54 (1H, m), 2.54-2.68 (2H, m), 3.72 (2H, q, J = 5.0 Hz), 4.02 (2H, t, J = 5.1 Hz), 4.85 (1H, t, J = 5.2 Hz), 6.98 (1H, dd, J = 2.5, 8.8 Hz), 7.03-7.10 (2H, m). |

TABLE 2-4-continued
| EX | STR | Prop | DATA |
|---|---|---|---|
| 29 | 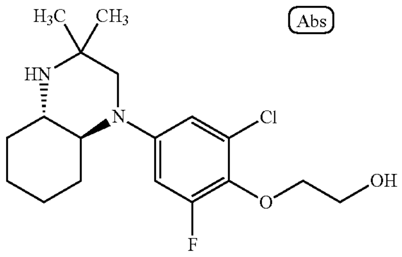 | 1 | NMR2: 0.60-1.12 (5H, m), 1.13-1.46 (6H, m), 1.60-1.81 (4H, m), 2.19 (1H, ddd, J = 3.0, 8.8, 11.5 Hz), 2.31-2.65 (2H, m), 2.67-2.85 (2H, m), 3.81-3.96 (2H, m), 4.13-4.25 (2H, m), 6.76 (1H, dd, J = 2.5, 12.2 Hz), 6.88 (1H, t, J = 2.2 Hz). |
TABLE 2-5
| EX | STR | Prop | DATA |
|---|---|---|---|
| 30 | 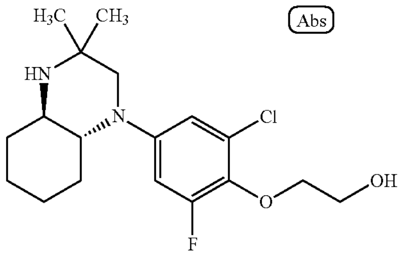 | 1 | NMR2: 0.64-1.14 (5H, m), 1.14-1.43 (6H, m), 1.58-1.80 (4H, m), 2.19 (1H, ddd, J = 3.1, 8.8, 11.5 Hz), 2.31-2.65 (2H, m), 2.67-2.82 (2H, m), 3.83-3.94 (2H, m), 4.15-4.22 (2H, m), 6.76 (1H, dd, J = 2.5, 12.2 Hz), 6.88 (1H, t, J = 2.1 Hz). |
| 31 | 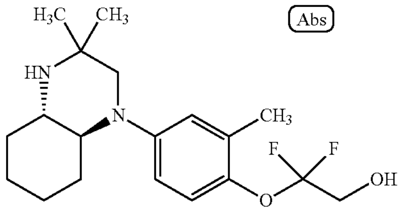 | 1 | NMR2: 0.62-1.45 {total 11H including 0.91-1.12 (4H, m), 1.14-1.44 (6H, m)}, 1.58-1.79 (4H, m), 1.99-3.00 (total 8H including 2.17-2.28 (4H, m), 2.59 (1H, d, J = 11.3 Hz), 2.70-2.81 (2H, m)}, 4.01 (2H, t, J = 8.9 Hz), 6.85-6.95 (2H, m), 7.10-7.15 (1H, m). |
| 32 | 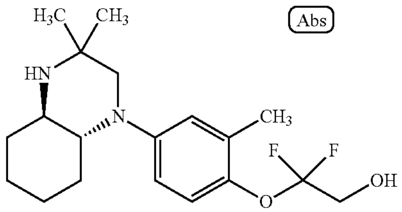 | 1 | NMR2: 0.62-1.11 (5H, m), 1.13-1.43 (6H, m), 1.57-1.78 (4H, m), 2.16-2.30 (4H, m), 2.30-3.13 {total 4H including 2.59 (1H, d, J = 11.3 Hz), 2.70-2.81 (2H, m)}, 4.01 (2H, t, J = 8.9 Hz), 6.86-6.94 (2H, m), 7.09-7.16 (1H, m). |
| 33 | 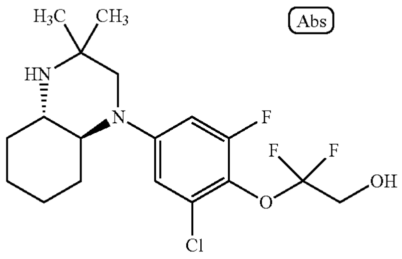 | 1 | NMR2: 0.71-1.13 (5H, m), 1.16-1.44 (6H, m), 1.64-1.81 (4H, m), 2.29 (1H, ddd, J = 3.1, 8.9, 11.8 Hz), 2.35-2.60 (1H, m), 2.65 (1H, d, J = 11.6 Hz), 2.70-2.80 (1H, m), 2.84 (1H, d, J = 11.6 Hz), 4.09 (2H, t, J = 9.0 Hz), 6.75 (1H, dd, J = 2.6, 11.5 Hz), 6.88 (1H, dd, J = 1.8, 2.6 Hz). |

TABLE 2-5-continued
| EX | STR | Prop | DATA |
|---|---|---|---|
| 34 | 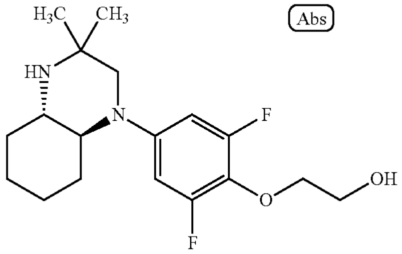 | 34 | NMR1: 0.85-1.04 (4H, m), 1.04-1.38 (6H, m), 1.38-1.74 (5H, m), 2.21-2.32 (1H, m), 2.55-2.66 (2H, m), 2.72 (1H, d, J = 11.2 Hz), 3.58-3.73 (2H, m), 4.01 (2H, t, J = 5.1 Hz), 4.81 (1H, t, J = 5.4 Hz), 6.67-6.81 (2H, m). |
| 35 | 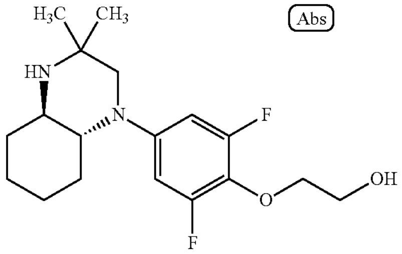 | 1 | NMR1: 0.85-1.04 (4H, m), 1.04-1.36 (6H, m), 1.38-1.74 (5H, m), 2.21-2.32 (1H, m), 2.55-2.66 (2H, m), 2.72 (1H, d, J = 11.2 Hz), 3.64 (2H, q, J = 5.1 Hz), 4.01 (2H, t, J = 5.1 Hz), 4.81 (1H, t, J = 5.4 Hz), 6.68-6.79 (2H, m). |
| 36 | 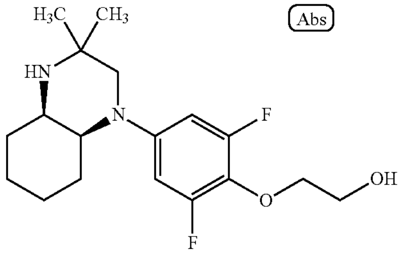 | 1 | NMR1: 0.92-1.17 (7H, m), 1.18-1.37 (2H, m), 1.37-1.72 (5H, m), 1.72-1.89 (1H, m), 2.54 (1H, d, J = 11.9 Hz), 3.01 (1H, d, J = 11.9 Hz), 3.19-3.26 (1H, m), 3.57-3.70 (3H, m), 3.91 (2H, t, J = 5.2 Hz), 4.77 (1H, t, J = 5.5 Hz), 6.49-6.61 (2H, m). |
TABLE 2-6
| EX | STR | Prop | DATA |
|---|---|---|---|
| 37 | 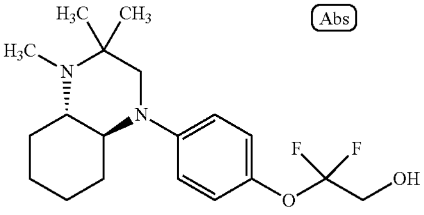 | 37 | NMR2: 0.96-1.34 (10H, m), 1.48-1.83 (3H, m), 2.06-2.15 (1H, m), 2.23 (3H, s), 2.25-2.34 (1H, m), 2.43 (1H, brs), 2.49-2.58 (1H, m), 2.65 (1H, d, J = 11.2 Hz), 2.81 (1H, dd, J = 0.9, 11.2 Hz), 3.99 (2H, t, J = 8.9 Hz), 7.03-7.15 (4H, m). |
| 38 | 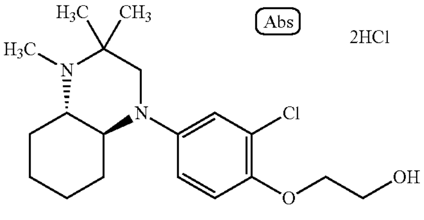 2HCl | 38 | NMR2: 1.21-1.47 (2H, m), 1.55-1.76 (5H, m), 1.77-1.99 (5H, m), 2.01-2.16 (1H, m), 2.17-2.26 (1H, m), 2.77 (3H, d, J = 4.9 Hz), 3.17 (1H, d, J = 13.2 Hz), 3.65 (1H, brs), 4.02 (2H, dd, J = 3.8, 5.1 Hz), 4.17 (2H, dd, J = 3.9, 5.1 Hz), 4.22-4.42 (2H, m), 6.99 (1H, d, J = 8.9 Hz), 7.78 (1H, brs), 7.93 (1H, brs), 12.79 (1H, brs). Two hydrogens could not be detected. |

TABLE 2-6-continued

| EX | STR | Prop | DATA |
|---|---|---|---|
| 39 | 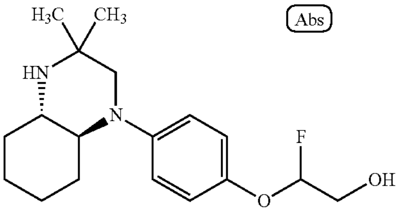 Abs | 1 | NMR2: 0.65-1.13 (5H, m), 1.13-1.46 (6H, m), 1.52-1.80 (4H, m), 1.95-2.31 (2H, m), 2.59 (1H, d, J = 1.1, 11.2 Hz), 2.70-2.81 (2H, m), 3.80-3.97 (2H, m), 5.80 (1H, tdd, J = 3.3, 4.6, 62.5 Hz), 6.97-7.10 (4H, m). |
| 40 | 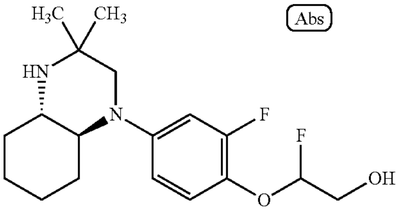 Abs | 1 | NMR2: 0.61-1.14 (5H, m), 1.14-1.42 (6H, m), 1.45-1.86 (4H, m), 1.95-2.42 (2H, m), 2.58 (1H, d, J = 11.2 Hz), 2.70-2.81 (2H, m), 3.92 (2H, dd, J = 4.6, 12.0 Hz), 5.71 (1H, tdd, J = 1.4, 4.6, 61.9 Hz), 6.82 (1H, ddd, J = 1.3, 2.5, 8.7 Hz), 6.87 (1H, dd, J = 2.5, 12.3 Hz), 7.08-7.17 (1H, m). |
| 41 | 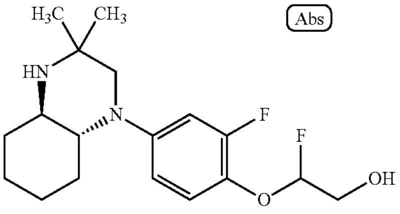 Abs | 1 | NMR2: 0.66-1.14 (5H, m), 1.14-1.44 (6H, m), 1.50-1.79 (4H, m), 2.04-2.34 (2H, m), 2.58 (1H, d, J = 11.2 Hz), 2.70-2.81 (2H, m), 3.92 (2H, dd, J = 4.6, 12.0 Hz), 5.71 (1H, tdd, J = 1.4, 4.6, 62.0 Hz), 6.82 (1H, ddd, J = 1.3, 2.5, 8.7 Hz), 6.87 (1H, dd, J = 2.5, 12.3 Hz), 7.09-7.17 (1H, m). |
| 42 | 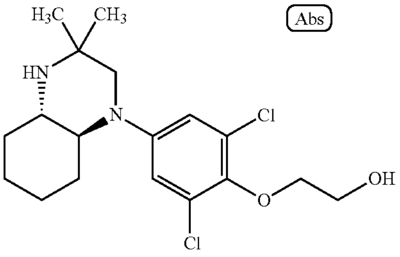 Abs | 1 | NMR2: 0.66-1.14 (5H, m), 1.16-1.43 (6H, m), 1.48-1.86 (4H, m), 2.20 (1H, ddd, J = 3.2, 8.8, 11.5 Hz), 2.44 (1H, brs), 2.58 (1H, d, J = 11.2 Hz), 2.69-2.82 (2H, m), 3.88-4.01 (2H, m), 4.10-4.23 (2H, m), 7.01 (2H, s). |
| 42 | 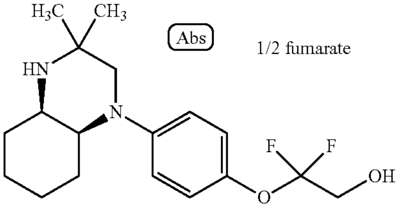 Abs 1/2 fumarate | 17 | NMR1: 1.07-1.34 (8H, m), 1.36-1.90 (6H, m), 2.66 (1H, d, J = 12.0 Hz), 3.03 (1H, d, J = 12.0 Hz), 3.29-3.35 (1H, m), 3.65-3.69 (1H, m), 3.78 (2H, t, J = 10.0 Hz), 6.80 (1H, brs), 6.49 (1H, s), 6.79-6.89 (2H, m), 6.96-7.02 (2H, m). Two hydrogens could not be detected. |

TABLE 2-7

| EX | STR | Prop | DATA |
|---|---|---|---|
| 44 | 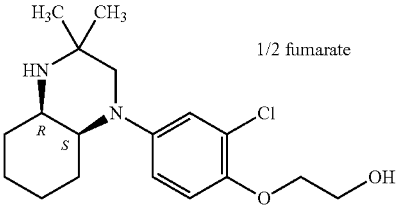 1/2 fumarate | 44 | NMR1: 0.93-1.39 (9H, m), 1.41-1.85 (5H, m), 2.66 (1H, d, J = 12.0 Hz), 2.94 (1H, d, J = 12.0 Hz), 3.38-3.43 (1H, m), 3.61-3.72 (3H, m), 3.95 (2H, t, J = 5.2 Hz), 4.82 (1H, brs), 6.48 (1H, s), 6.79 (1H, dd, J = 9.1, 3.0 Hz), 6.90 (1H, d, J = 3.0 Hz), 7.00 (1H, d, J = 9.1 Hz). Two hydrogens could not be detected. |

TABLE 2-7-continued

| EX | STR | Prop | DATA |
|---|---|---|---|
| 45 | 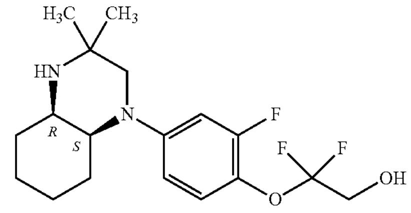 | 1 | NMR2: 1.09-1.50 (11H, m), 1.62-1.83 (4H, m), 2.28 (1H, s), 2.70 (1H, d, J = 11.9 Hz), 2.96 (1H, d, J = 11.9 Hz), 3.37-3.44 (1H, m), 3.52-3.61 (1H, m), 4.01 (2H, t, J = 8.8 Hz), 6.49-6.62 (2H, m), 7.06-7.15 (1H, m) |
| 46 | 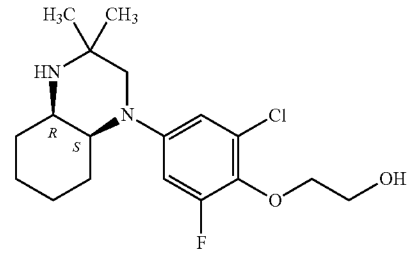 | 1 | NMR2: 1.14-1.31 (8H, m), 1.32-1.48 (3H, m), 1.63-1.83 (4H, m), 2.39 (1H, s), 2.67 (1H, d, J = 11.8 Hz), 2.88 (1H, d, J = 11.8 Hz), 3.36-3.42 (1H, m), 3.45-3.53 (1H, m), 3.84-3.89 (2H, m), 4.09-4.16 (2H, m), 6.45-6.54 (1H, m), 6.55-6.60 (1H, m) |
| 47 | 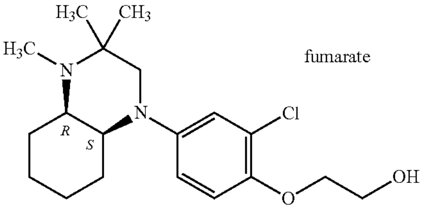 fumarate | 47 | NMR1: 0.96 (3H, s), 1.01-1.10 (1H, m), 1.14 (3H, s), 1.20-1.43 (4H, m), 1.61-1.68 (1H, m), 1.89-2.04 (2H, m), 2.10 (3H, s), 2.77-2.84 (2H, m), 2.90 (1H, d, J = 11.8 Hz), 3.62-3.72 (3H, m), 3.94 (2H, t, J = 5.2 Hz), 4.85 (1H, brs), 6.57 (2H, s), 6.77 (1H, dd, J = 9.0, 3.0 Hz), 6.88 (1H, d, J = 3.0 Hz), 6.99 (1H, d, J = 9.0 Hz). Two hydrogens could not be detected. |
| 48 | 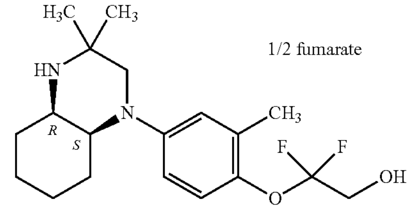 1/2 fumarate | 17 | NMR1: 0.97-1.37 (9H, m), 1.40-1.72 (4H, m), 1.73-1.87 (1H, m), 2.15 (3H, s), 2.69 (1H, d, J = 12.1 Hz), 3.05 (1H, d, J = 12.1 Hz), 3.38-3.44 (1H, m), 3.68-3.75 (1H, m), 3.82 (2H, t, J = 9.9 Hz), 5.82 (1H, brs), 6.49 (1H, s), 6.62-6.80 (2H, m), 6.96 (1H, dd, J = 8.9, 1.6 Hz). Two hydrogens could not be detected. |
| 49 | 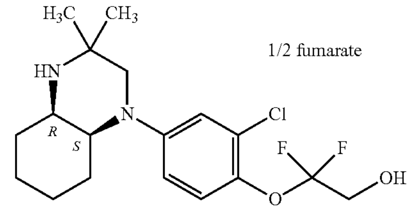 1/2 fumarate | 17 | NMR1: 1.04-1.37 (9H, m), 1.41-1.73 (4H, m), 1.76-1.89 (1H, m), 2.68 (1H, d, J = 12.3 Hz), 3.13 (1H, d, J = 12.3 Hz), 3.34-3.39 (1H, m), 3.71-3.79 (1H, m), 3.84 (2H, t, J = 10.6 Hz), 5.88 (1H, brs), 6.51 (1H, s), 6.85 (1H, dd, J = 9.1, 3.0 Hz), 6.96 (1H, d, J = 3.0 Hz), 7.15 (1H, d, J = 9.1 Hz). |

TABLE 2-8

| EX | STR | Prop | DATA |
|---|---|---|---|
| 50 | 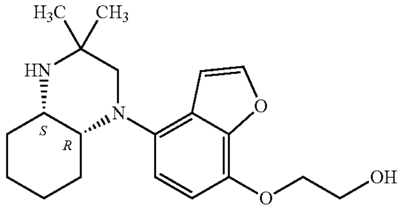 | 1 | NMR2: 1.07 (2H, dd, J = 10.3, 3.5 Hz), 1.20 (3H, s), 1.30-1.43 (5H, m), 1.50-1.92 {total 5H including 1.59-1.92 (4H, m)}, 2.30 (1H, s), 2.69 (1H, d, J = 11.3 Hz), 3.04 (1H, d, J = 11.3 Hz), 3.43-3.53 (1H, m), 3.59-3.64 (1H, m), 3.96-4.03 (2H, m), 4.22-4.29 (2H, m), 6.50 (1H, d, J = 8.4 Hz), 6.73 (1H, d, J = 8.4 Hz), 6.82 (1H, d, J = 2.1 Hz), 7.58 (1H, d, J = 2.1 Hz). |

TABLE 2-8-continued

| EX | STR | Prop | DATA |
|---|---|---|---|
| 51 | 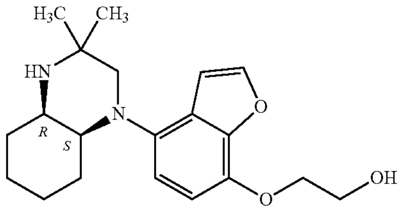 | 1 | NMR2: 0.96-1.15 (2H, m), 1.20 (3H, s), 1.25-1.50 (4H, m), 1.52-1.94 {total 6H including 1.58-1.92 (4H, m)}, 2.33 (1H, s), 2.69 (1H, d, J = 11.3 Hz), 3.04 (1H, d, J = 11.3 Hz), 3.43-3.53 (1H, m), 3.59-3.64 (1H, m), 3.96-4.03 (2H, m), 4.22-4.29 (2H, m), 6.50 (1H, d, J = 8.4 Hz), 6.73 (1H, d, J = 8.4 Hz), 6.82 (1H, d, J = 2.1 Hz), 7.58 (1H, d, J = 2.1 Hz). |
| 52 | 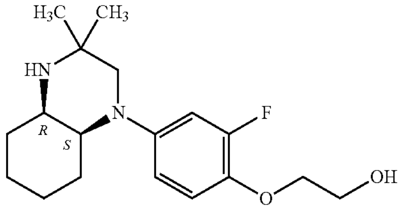 | 1 | NMR2: 1.02-1.48 (9H, m), 1.50-1.83 {total 6H including 1.58-1.83 (4H, m)}, 2.17 (1H, s), 2.67 (1H, d, J = 11.7 Hz), 2.86 (1H, d, J = 11.7 Hz), 3.39-3.45 (1H, m), 3.46-3.55 (1H, m), 3.87-3.94 (2H, m), 4.04-4.11 (2H, m), 6.47-6.55 (1H, m), 6.61 (1H, dd, J = 14.6, 2.9 Hz), 6.90 (1H, dd, J = 9.7, 9.0 Hz). |
| 53 | 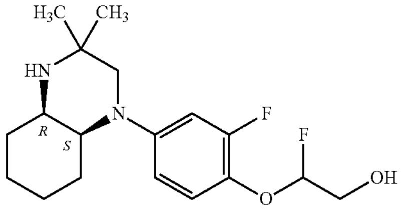 | 1 | NMR2: 0.99-1.49 (8H, m), 1.40-1.82 {total 7H including 1.58-1.82 (4H, m)}, 1.99 (1H, s), 2.69 (1H, d, J = 11.8 Hz), 2.92 (1H, dd, J = 11.8, 2.0 Hz), 3.39-3.44 (1H, m), 3.50-3.59 (1H, m), 3.85-3.93 (2H, m), 5.46-5.80 (1H, m), 6.49-6.64 (2H, m), 7.02-7.12 (1H, m). |
| 54 | 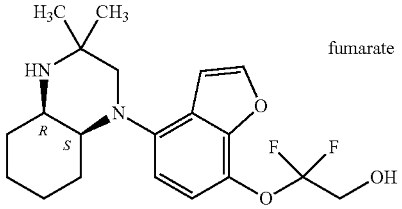 fumarate | 17 | NMR1: 0.83-1.13 (2H, m), 1.28 (3H, s), 1.33 (3H, s), 1.43-1.82 (5H, m), 1.87-2.01 (1H, m), 2.85 (1H, d, J = 12.1 Hz), 3.13 (1H, d, J = 12.1 Hz), 3.40-3.45 (1H, m), 3.65-3.79 (2H, m), 3.90 (2H, t, J = 10.3 Hz), 5.95 (1H, s), 6.52 (2H, s), 6.60 (1H, d, J = 8.5 Hz), 7.05 (1H, d, J = 8.5 Hz), 7.15 (1H, d, J = 2.1 Hz), 7.97 (1H, d, J = 2.1 Hz). Three hydrogens could not be detected. |
| 55 | 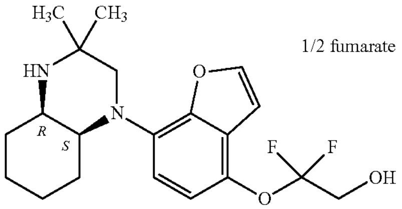 1/2 fumarate | 17 | NMR1: 0.90-1.37 (9H, m), 1.41-1.76 (4H, m), 1.89-2.04 (1H, m), 2.91-3.05 (2H, m), 3.53-3.58 (1H, m), 3.84-3.99 (3H, m), 5.90 (1H, s), 6.48 (1H, s), 6.67 (1H, d, J = 8.5 Hz), 6.89 (1H, d, J = 2.2 Hz), 6.95 (1H, d, J = 8.5 Hz), 7.98 (1H, d, J = 2.2 Hz). Two hydrogens could not be detected. |

TABLE 2-9

| EX | STR | Prop | DATA |
|---|---|---|---|
| 56 | 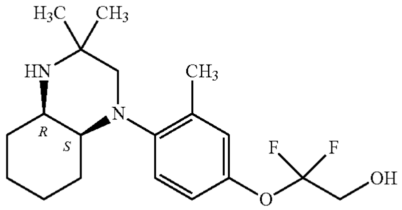 | 56 | NMR2: 0.95-1.10 (2H, m), 1.16 (3H, s), 1.28-1.41 (5H, m), 1.54-1.76 (4H, m), 1.78-1.93 (1H, m), 2.10 (1H, brs), 2.32 (3H, s), 2.39 (1H, d, J = 11.0 Hz), 2.82-2.91 (1H, m), 3.10 (1H, d, J = 11.0 Hz), 3.49-3.54 (1H, m), 3.97 (2H, t, J = 8.8 Hz), 6.83 (1H, d, J = 8.6 Hz), 6.91-6.98 (1H, m), 6.98-7.04 (1H, m). |

TABLE 2-9-continued

| EX | STR | Prop | DATA |
|---|---|---|---|
| 57 | 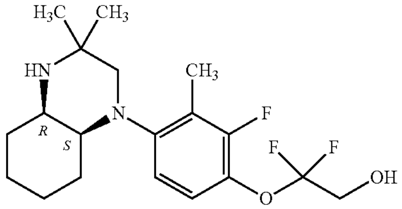 | 1 | NMR2: 0.94-1.12 (2H, m), 1.16 (3H, s), 1.30 (5H, s), 1.54-1.77 (4H, m), 1.85 (1H, qd, J = 13.1, 3.4 Hz), 2.25 (4H, d, J = 2.8 Hz), 2.41 (1H, d, J = 11.0 Hz), 2.83-2.92 (1H, m), 3.08 (1H, d, J = 11.1 Hz), 3.50-3.56 (1H, m), 4.02 (2H, t, J = 8.8 Hz), 6.61 (1H, dd, J = 8.8, 1.8 Hz), 7.03 (1H, t, J = 8.8 Hz). |
| 58 | 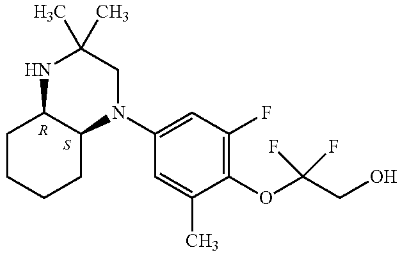 | 1 | NMR2: 0.82-1.94 {total 15H including 0.93-1.14 (4H, m), 1.16-1.44 (6H, m), 1.59-1.84 (4H, m)}, 2.09-3.02 (total 8H including 2.22 (1H, ddd, J = 3.0, 8.8, 11.7 Hz), 2.28 (3H, s), 2.59 (1H, d, J = 11.3 Hz), 2.69-2.82 (2H, m)}, 4.06 (2H, t, J = 9.0 Hz), 6.62-6.78 (2H, m). |
| 59 | 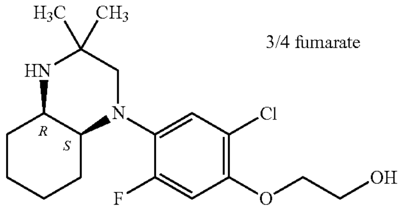 3/4 fumarate | 59 | NMR1: 0.94-1.15 (2H, m), 1.15-1.33 (7H, m), 1.39-1.78 (4H, m), 1.83-1.97 (1H, m), 2.56 (1H, d, J = 11.8 Hz), 3.05 (1H, d, J = 11.8 Hz), 3.27-3.36 (1H, m), 3.51-3.58 (1H, m), 3.70 (2H, t, J = 5.0 Hz), 4.02 (2H, t, J = 5.0 Hz), 4.77 (1H, brs), 6.52 (1.5H, s), 7.02 (1H, d, J = 9.0 Hz), 7.09 (1H, d, J = 14.0 Hz). Two point five hydrogens could not be detected. |
| 60 | 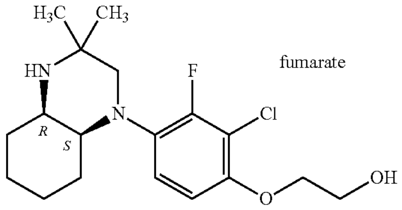 fumarate | 60 | NMR1: 0.91-1.35 (9H, m), 1.37-1.76 (4H, m), 1.84-1.98 (1H, m), 2.57 (1H, d, J = 11.9 Hz), 3.10 (1H, d, J = 11.9 Hz), 3.25-3.34 (1H, m), 3.54-3.60 (1H, m), 3.68-3.75 (2H, m), 3.98-4.09 (2H, m), 4.88 (1H, brs), 6.53 (2H, s), 6.86-6.98 (2H, m). Three hydrogens could not be detected. |
| 61 | 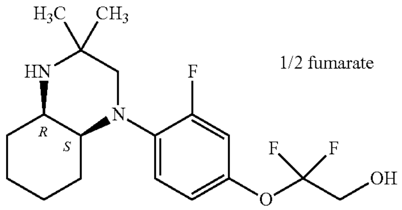 1/2 fumarate | 61 | NMR1: 0.77-1.33 (9H, m), 1.45-1.85 (4H, m), 1.87-2.01 (1H, m), 2.66 (1H, d, J = 11.9 Hz), 3.06 (1H, d, J = 11.9 Hz), 3.42-3.53 (2H, m), 3.81 (2H, t, J = 10.1 Hz), 5.70 (1H, brs), 6.52 (1.5H, s), 6.91-7.05 (3H, m). Two point fice hydrogens could not be detected. |
| 62 | 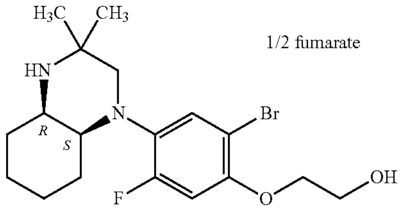 1/2 fumarate | 59 | NMR1: 0.88-1.31 (9H, m), 1.57 (4H, dq, J = 40.2, 13.4, 12.8 Hz), 1.83-1.97 (1H, m), 2.50-2.53 (1H, m), 3.00 (1H, d, J = 11.6 Hz), 3.22-3.32 (1H, m), 3.47-3.51 (1H, m), 3.70 (2H, t, J = 5.0 Hz), 4.01 (2H, t, J = 5.1 Hz), 4.86 (1H, brs), 6.51 (1H, s), 7.06 (1H, d, J = 14.2 Hz), 7.11 (1H, d, J = 9.2 Hz). Two hydrogens could not be detected. |

TABLE 2-10

| EX | STR | Prop | DATA |
|---|---|---|---|
| 63 | 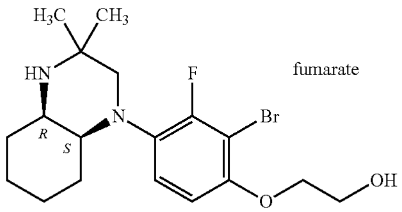 fumarate | 59 | NMR1: 0.91-1.15 (2H, m), 1.20 (3H, s), 1.23-1.33 (4H, m), 1.37-1.74 (4H, m), 1.84-1.98 (1H, m), 2.51-2.57 (1H, m), 3.07 (1H, d, J = 11.7 Hz), 3.22-3.30 (1H, m), 3.50-3.57 (1H, m), 3.68-3.75 (2H, m), 3.96-4.07 (2H, m), 4.87 (1H, brs), 6.53 (2H, s), 6.86 (1H, dd, J = 9.0, 1.6 Hz), 6.96 (1H, t, J = 9.0 Hz). Three hydrogens could not be detected. |
| 64 | 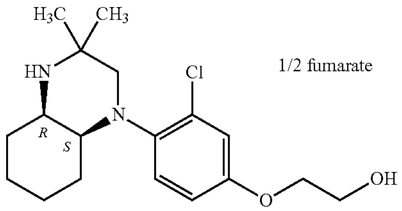 1/2 fumarate | 64 | NMR1: 0.85-1.09 (2H, m), 1.19 (3H, s), 1.23-1.38 (4H, m), 1.43-1.74 (4H, m), 1.86-2.01 (1H, m), 2.36 (1H, d, J = 11.4 Hz), 3.07-3.23 (2H, m), 3.52-3.57 (1H, m), 3.64-3.72 (2H, m), 3.91-3.98 (2H, m), 4.91 (1H, brs), 6.48 (1H, s), 6.85 (1H, dd, J = 8.8, 2.9 Hz), 6.95-7.02 (2H, m). Two hydrogens could not be detected. |
| 65 | 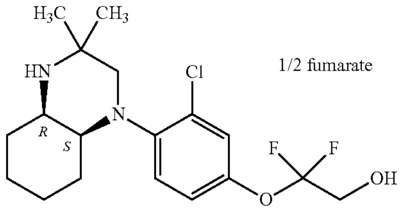 1/2 fumarate | 61 | NMR1: δ 0.84-0.90 (1H, m), 0.98-1.09 (1H, m), 1.14 (3H, s), 1.20-1.30 (4H, m), 1.43-1.67 (4H, m), 1.91-2.03 (1H, m), 2.40 (1H, d, J = 11.2 Hz), 3.14 (1H, d, J = 11.2 Hz), 3.31-3.34 (1H, m), 3.49-3.52 (1H, m), 3.82 (2H, t, J = 10.1 Hz), 5.88 (1H, brs), 6.49 (1H, s), 7.07 (1H, d, J = 8.8 Hz), 7.12 (1H, dd, J = 8.8, 2.7 Hz), 7.23 (1H, d, J = 2.7 Hz). Two hydrogens could not be detected. |
| 66 | 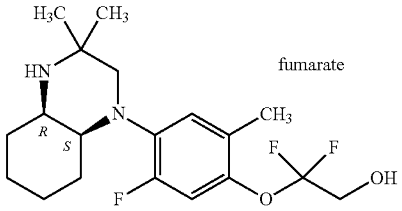 fumarate | 61 | NMR1: 0.80-1.34 (9H, m), 1.42-1.79 (4H, m), 1.87-1.99 (1H, m), 2.15 (3H, s), 2.67 (1H, d, J = 11.9 Hz), 3.07 (1H, d, J = 11.9 Hz), 3.36-3.46 (1H, m), 3.54-3.58 (1H, m), 3.85 (2H, t, J = 10.0 Hz), 5.89 (1H, brs), 6.53 (2H, s), 6.88 (1H, d, J = 9.8 Hz), 6.95 (1H, d, J = 13.1 Hz). Three hydrogens could not be detected. |
| 67 | 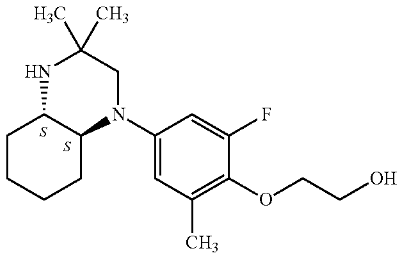 | 1 | NMR2: 0.68-1.14 (5H, m), 1.14-1.43 (6H, m), 1.58-1.77 (4H, m), 2.09-2.24 (2H, m), 2.27 (3H, s), 2.54 (1H, d, J = 11.2 Hz), 2.68-2.79 (2H, m), 3.85-3.97 (2H, m), 4.05-4.14 (2H, m), 6.64-6.74 (2H, m). |
| 68 | 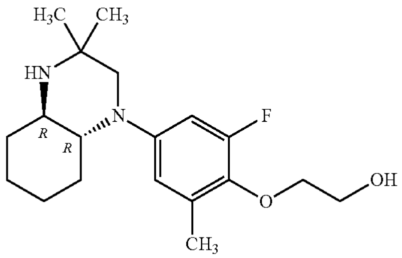 | 1 | NMR2: 0.68-1.14 (5H, m), 1.14-1.43 (6H, m), 1.58-1.77 (4H, m), 2.09-2.24 (2H, m), 2.27 (3H, s), 2.54 (1H, d, J = 11.2 Hz), 2.68-2.79 (2H, m), 3.85-3.97 (2H, m), 4.05-4.14 (2H, m), 6.64-6.74 (2H, m). |

TABLE 2-11

| EX | STR | Prop | DATA |
|---|---|---|---|
| 69 | 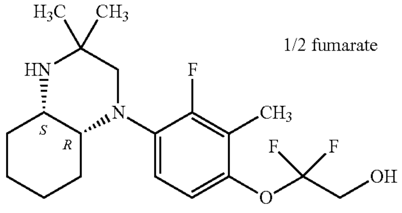 1/2 fumarate | 69 | NMR1: 0.86-1.15 (2H, m), 1.18 (3H, s), 1.22-1.31 (4H, m), 1.46-1.71 (4H, m), 1.91-1.98 (1H, m), 2.04-2.17 (3H, m), 2.58 (1H, d, J = 11.7 Hz), 3.03 (1H, d, J = 11.7 Hz), 3.33-3.42 (1H, m), 3.47-3.55 (1H, m), 3.86 (2H, t, J = 9.8 Hz), 5.90 (1H, brs), 6.50 (1H, s), 6.82 (1H, t, J = 9.0 Hz), 6.93 (1H, d, J = 9.0 Hz). Two hydrogens could not be detected. |
| 70 | 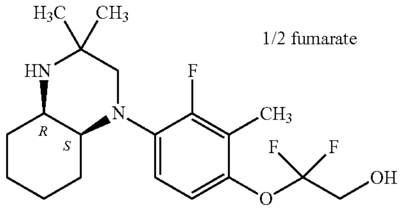 1/2 fumarate | 61 | NMR1: 0.92-1.00 (1H, m), 1.05-1.12 (1H, m), 1.17 (3H, s), 1.22-1.34 (4H, m), 1.38-1.72 (4H, m), 1.89-2.02 (1H, m), 2.06-2.14 (3H, m), 2.58-(1H, d, J = 11.6 Hz), 3.03 (1H, d, J = 11.6 Hz), 3.32-3.41 (1H, m), 3.47-3.54 (1H, m), 3.86 (2H, t, J = 9.8 Hz), 5.91 (1H, brs), 6.50 (1H, s), 6.81 (1H, t, J = 9.0 Hz), 6.93 (1H, d, J = 9.0 Hz). Two hydrogens could not be detected. |
| 71 | 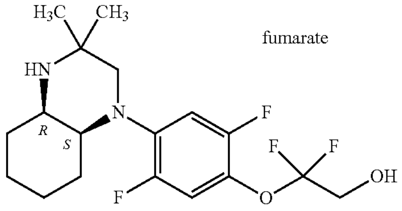 fumarate | 61 | NMR1: 0.85-1.33 (9H, m), 1.37-1.74 (4H, m), 1.89-2.01 (1H, m), 2.71 (1H, d, J = 12.0 Hz), 3.01 (1H, d, J = 12.0 Hz), 3.44-3.55 (2H, m), 3.85 (2H, t, J = 10.4 Hz), 5.97 (1H, brs), 6.55 (2H, s), 6.99 (1H, dd, J = 12.4, 8.2 Hz), 7.20 (1H, dd, J = 12.8, 7.4 Hz). Three hydrogens could not be detected. |
| 72 | 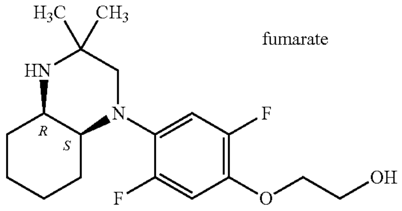 fumarate | 59 | NMR1: 0.84-1.35 (9H, m), 1.40-1.79 (4H, m), 1.83-1.97 (1H, m), 2.58 (1H, d, J = 12.0 Hz), 3.05 (1H, d, J = 12.0 Hz), 3.31-3.39 (1H, m), 3.51-3.61 (1H, m), 3.69 (2H, t, J = 4.9 Hz), 4.00 (2H, t, J = 4.9 Hz), 4.99 (1H, brs), 6.53 (2H, s), 6.91 (1H, dd, J = 13.1, 8.3 Hz), 7.08 (1H, dd, J = 13.8, 8.2 Hz). Three hydrogens could not be detected. |
| 73 | 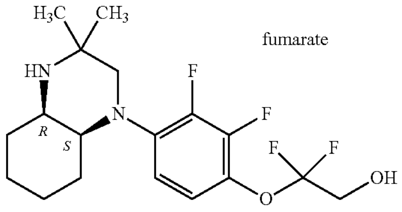 fumarate | 61 | NMR1: 0.94-1.34 (9H, m), 1.38-1.72 (4H, m), 1.90-2.04 (1H, m), 2.73 (1H, d, J = 12.0 Hz), 3.04 (1H, d, J = 12.0 Hz), 3.42-3.50 (1H, m), 3.50-3.56 (1H, m), 3.87 (2H, t, J = 10.3 Hz), 5.95 (1H, brs), 6.56 (2H, s), 6.76-6.86 (1H, m), 7.07 (1H, t, J = 8.9 Hz). Three hydrogens could not be detected. |
| 74 | 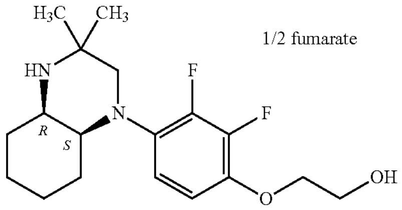 1/2 fumarate | 74 | NMR1: 0.97-1.05 (2H, m), 1.20 (3H, s), 1.26-1.29 (4H, m), 1.35-1.70 (4H, m), 1.84-1.98 (1H, m), 2.50-2.56 (1H, m), 2.99 (1H, d, J = 11.6 Hz), 3.21-3.32 (1H, m), 3.46-3.51 (1H, m), 3.70 (2H, t, J = 4.9 Hz), 4.01 (2H, t), 4.90 (1H, brs), 6.51 (1H, s), 6.63-6.73 (1H, m), 6.82-6.92 (1H, m). Two hydrogens could not be detected. |

TABLE 2-12

| EX | STR | Prop | DATA |
|---|---|---|---|
| 75 | 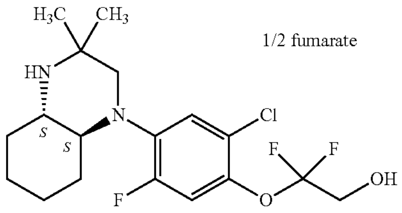 1/2 fumarate | 61 | NMR1: 0.85-1.14 (5H, m), 1.21-1.43 (5H, m), 1.43-1.80 (4H, m), 2.53-2.89 (4H, m), 3.90 (2H, t, J = 10.7 Hz), 5.98 (1H, brs), 6.46 (1H, s), 7.31 (1H, d, J = 11.0 Hz), 7.46 (1H, d, J = 8.1 Hz). Two hydrogens could not be detected. |
| 76 | 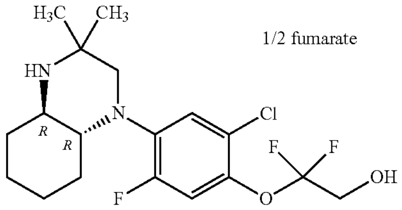 1/2 fumarate | 61 | NMR1: 0.90-1.43 (9H, m), 1.47-1.78 (5H, m), 2.55-2.89 (4H, m), 3.90 (2H, t, J = 10.6 Hz), 6.01 (1H, brs), 6.44 (1H, s), 7.31 (1H, d, J = 11.0 Hz), 7.46 (1H, d, J = 8.3 Hz). Two hydrogens could not be detected. |
| 77 | 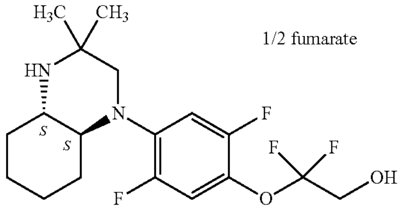 1/2 fumarate | 61 | NMR1: 0.78-1.12 (4H, m), 1.17-1.42 (6H, m), 1.50-1.74 (4H, m), 2.55-2.83 (4H, m), 3.87 (2H, t, J = 10.6 Hz), 5.96 (1H, brs), 6.43 (1H, s), 7.24-7.36 (2H, m). Two hydrogens could not be detected. |
| 78 | 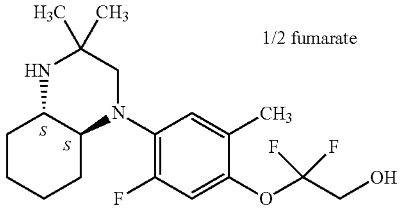 1/2 fumarate | 61 | NMR1: 0.90-1.11 (4H, m), 1.12-1.41 (6H, m), 1.48-1.74 (4H, m), 2.17 (3H, s), 2.53-2.85 (4H, m), 3.86 (2H, t, J = 10.0 Hz), 5.92 (1H, brs), 6.44 (1H, s), 7.00 (1H, d, J = 11.3 Hz), 7.15 (1H, d, J = 9.0 Hz). Two hydrogens could not be detected. |
| 79 | 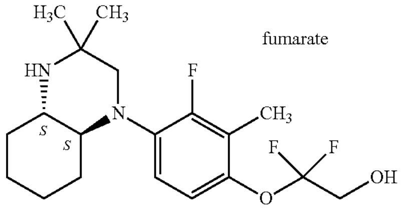 fumarate | 61 | NMR1: 0.92-1.03 (1H, m), 1.13 (3H, s), 1.16-1.36 (3H, m), 1.42 (3H, s), 1.49-1.79 (4H, m), 2.10-2.14 (3H, m), 2.55-2.95 (4H, m), 3.88 (2H, t, J - 9.8 Hz), 5.93 (1H, brs), 6.48 (2H, s), 7.02 (1H, d, J = 8.7 Hz), 7.11 (1H, t, J = 8.7 Hz). Three hydrogens could not be detected. |
| 80 | 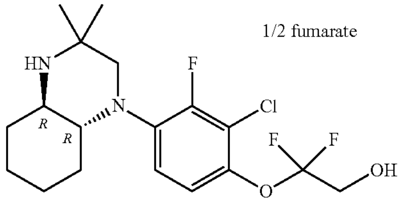 1/2 fumarate | 61 | NMR1: 0.91-1.03 (1H, m), 1.08 (3H, s), 1.14-1.33 (3H, m), 1.37 (3H, s), 1.50-1.74 (4H, m), 2.56-2.88 (4H, m), 3.91 (2H, t, J = 10.6 Hz), 5.99 (1H, brs), 6.46 (1H, s), 7.16-7.34 (2H, m). Two hydrogens could not be detected. |

TEST EXAMPLES

The following shows the results of pharmacological test and the like for the repre-sentative compounds of the present invention and describes pharmacological effects of the compounds, but the present invention is not limited to these test examples.

Test Example 1 (Measurement of Serotonin (5-HT) Uptake Inhibitory Activity of Test Compound in Rat Brain Synaptosome)

Male Wistar rats were decapitated, each brain was removed, and the frontal cortex was cut out. The isolated frontal cortex was placed in a 0.32 molar (M) sucrose solution at 20 times its weight and homogenized with a Potter homogenizer. The homogenate was centrifuged at 1000 g at 4° C. for 10 minutes, and the supernatant was further centrifuged at 20000 g at 4° C. for 20 minutes. The pellet was suspended in an incubation buffer (20 mM Hepes buffer (pH 7.4) containing 10 mM glucose, 145 mM sodium chloride, 4.5 mM potassium chloride, 1.2 mM magnesium chloride and 1.5 mM calcium chloride) and used as crude synaptosomal fraction.

Each well of a 96-well round-bottom plate was used for the uptake reaction in a total volume of 200 μL solution containing purgurin (final concentration 10 μM) and ascorbic acid (final concentration 0.2 mg/mL).

In other words, solvent, unlabeled 5-HT or step-diluted test compound was added to each well, and one-tenth of the final volume of the synaptosomal fraction was added to each well, followed by pre-incubation at 37° C. for 10 minutes, and then tritium-labeled 5-HT solution (final concentration 8 nM) was added and the uptake reaction was initiated at 37° C. After 10 minutes, the uptake reaction was terminated by suction filtration onto a 96-well glass fiber filter plate. The filters were rinsed with cold physi-ological saline solution, dried thoroughly, and micro scintillation 0 (Perkin-Elmer) was added thereto. Then, the residual radioactivity on the filters was measured.

The uptake value when only solvent was added was set as 100%, the uptake value when unlabeled 5-HT (final concentration 10 μM) was added as 0% (nonspecific uptake value), and the 50% inhibitory concentration was calculated from the concentration of the test compound and its inhibitory activity. The results are shown in Table 3.

TABLE 3

| Ex. | IC50 (nM) | Ex. | IC50 (nM) | Ex. | IC50 (nM) | Ex. | IC50 (nM) |
|---|---|---|---|---|---|---|---|
| 1 | 6.1 | 2 | 5.5 | 3 | 6.1 | 4 | 6.0 |
| 5 | 7.9 | 6 | 6.1 | 7 | 6.7 | 8 | 10.0 |
| 9 | 8.6 | 10 | 19.7 | 11 | 39.6 | 12 | 6.2 |
| 13 | 8.8 | 14 | 5.8 | 15 | 44.2 | 16 | 54.0 |
| 17 | 7.3 | 18 | 73.1 | 19 | 62.7 | 20 | 4.7 |
| 21 | 89.9 | 22 | 8.4 | 23 | 79.2 | 24 | 8.6 |
| 25 | 7.6 | 26 | 18.1 | 27 | 7.6 | 28 | 55.1 |
| 29 | 6.3 | 30 | 30.8 | 31 | 26.6 | 32 | 98.3 |
| 33 | 11.0 | 34 | 8.9 | 35 | 71.0 | 36 | 60.1 |
| 37 | 87.4 | 38 | 75.3 | 39 | 7.2 | 40 | 7.7 |
| 41 | 76.4 | 42 | 6.1 | 43 | 42.5 | 44 | 15.3 |
| 45 | 48.1 | 46 | 8.6 | 47 | 49.9 | 48 | 57.4 |
| 49 | 27.2 | 50 | 7.7 | 51 | 17.0 | 52 | 55.0 |
| 53 | 34.3 | 54 | 7.7 | 55 | 9.8 | 56 | 13.2 |
| 57 | 30.3 | 58 | 22.9 | 59 | 9.2 | 60 | 7.0 |
| 61 | 9.0 | 62 | 8.6 | 63 | 5.1 | 64 | 8.8 |
| 65 | 7.8 | 66 | 20.8 | 67 | 7.1 | 68 | 74.0 |
| 69 | 5.7 | 70 | 7.0 | 71 | 57.0 | 72 | 55.4 |
| 73 | 8.7 | 74 | 17.7 | 75 | 9.4 | 76 | 98.3 |
| 77 | 42.3 | 78 | 31.4 | 79 | 37.3 | 80 | 62.8 |

Test Example 2 (Measurement of Norepinephrine (NE) Uptake Inhibitory Activity of Test Compound Using Rat Brain Synaptosome)

Male Wistar rats were decapitated, each brain was removed, and the hippocampus was cut out. The isolated hippocampus was placed in a 0.32 molar (M) sucrose solution at 20 times its weight and homogenized with a Potter homogenizer. The homogenate was centrifuged at 1000 g at 4° C. for 10 minutes, and the supernatant was further centrifuged at 20000 g at 4° C. for 20 minutes. The pellet was suspended in an incubation buffer (20 mM Hepes buffer (pH 7.4) containing 10 mM glucose, 145 mM sodium chloride, 4.5 mM potassium chloride, 1.2 mM magnesium chloride and 1.5 mM calcium chloride) and used as crude synaptosomal fraction.

Each well of a 96-well round-bottom plate was used for the uptake reaction in a total volume of 200 μL solution containing purgurin (final concentration 10 μM) and ascorbic acid (final concentration 0.2 mg/mL).

In other words, solvent, unlabeled NE or step-diluted test compound was added to each well, and one-tenth of the final volume of the synaptosomal fraction was added to each well, followed by pre-incubation at 37° C. for 10 minutes, and then tritium-labeled NE solution (final concentration 12 nM) was added and the uptake reaction was initiated at 37° C. After 10 minutes, the uptake reaction was terminated by suction filtration onto a 96-well glass fiber filter plate. The filters were rinsed with cold physi-ological saline solution, dried thoroughly, and micro scintillation 0 (Perkin-Elmer) was added thereto. Then, the residual radioactivity on the filters was measured.

The uptake value when only solvent was added was set as 100%, the uptake value when unlabeled NE (final concentration 10 μM) was added as 0% (nonspecific uptake value), and the 50% inhibitory concentration was calculated from the concentration of the test compound and its inhibitory activity. The results are shown in Table 4.

TABLE 4

| Ex. | IC50 (nM) | Ex. | IC50 (nM) | Ex. | IC50 (nM) | Ex. | IC50 (nM) |
|---|---|---|---|---|---|---|---|
| 1 | 7.2 | 2 | 5.2 | 3 | 6.0 | 4 | 15.2 |
| 5 | 17.6 | 6 | 8.4 | 7 | 6.5 | 8 | 37.2 |
| 9 | 45.6 | 10 | 37.5 | 11 | 91.0 | 12 | 5.8 |
| 13 | 35.4 | 14 | 8.5 | 15 | 4.0 | 16 | 5.6 |
| 17 | 2.7 | 18 | 13.3 | 19 | 2.4 | 20 | 4.4 |
| 21 | 69.0 | 22 | 4.8 | 23 | 10.3 | 24 | 7.3 |
| 25 | 7.2 | 26 | 21.3 | 27 | 7.7 | 28 | 9.7 |
| 29 | 5.9 | 30 | 6.7 | 31 | 5.5 | 32 | 7.5 |
| 33 | 5.7 | 34 | 5.9 | 35 | 6.8 | 36 | 5.1 |
| 37 | 34.5 | 38 | 30.3 | 39 | 9.8 | 40 | 8.5 |
| 41 | 27.8 | 42 | 9.2 | 43 | 35.1 | 44 | 5.2 |
| 45 | 8.0 | 46 | 3.8 | 47 | 6.8 | 48 | 6.6 |
| 49 | 1.1 | 50 | 5.8 | 51 | 4.3 | 52 | 8.3 |
| 53 | 5.5 | 54 | 2.9 | 55 | 0.8 | 56 | 3.9 |
| 57 | 4.9 | 58 | 6.4 | 59 | 7.4 | 60 | 3.9 |
| 61 | 6.1 | 62 | 6.9 | 63 | 3.6 | 64 | 5.4 |
| 65 | 1.4 | 66 | 5.8 | 67 | 7.8 | 68 | 41.7 |
| 69 | 3.4 | 70 | 1.0 | 71 | 6.3 | 72 | 7.9 |
| 73 | 2.4 | 74 | 5.4 | 75 | 9.7 | 76 | 8.8 |
| 77 | 7.1 | 78 | 8.4 | 79 | 5.8 | 80 | 12.4 |

Test Example 3 (Measurement of Dopamine (DA) Uptake Inhibitory Activity of Test Compound Using Rat Brain Synaptosome)

Male Wistar rats were decapitated, each brain was removed, and the striatum was cut out. The isolated striatum was placed in a 0.32 molar (M) sucrose solution at 20 times its weight and homogenized with a Potter homogenizer. The homogenate was centrifuged at 1000 g at 4° C. for 10 minutes, and the supernatant was further centrifuged at 20000 g at 4° C. for 20 minutes. The pellet was suspended in an incubation buffer (20 mM Hepes buffer (pH 7.4) containing 10 mM glucose, 145 mM sodium chloride, 4.5 mM potassium chloride, 1.2 mM magnesium chloride and 1.5 mM calcium chloride) and used as crude synaptosomal fraction.

Each well of a 96-well round-bottom plate was used for the uptake reaction in a total volume of 200 μl solution containing purgurin (final concentration 10 μM) and ascorbic acid (final concentration 0.2 mg/mL).

In other words, solvent, unlabeled DA or step-diluted test compound was added to each well, and one-tenth of the final volume of the synaptosomal fraction was added to each well, followed by pre-incubation at 37° C. for 10 minutes, and then tritium-labeled DA solution (final concentration 2 nM) was added and the uptake reaction was initiated at 37° C. After 10 minutes, the uptake reaction was terminated by suction filtration onto a 96-well glass fiber filter plate. The filters were rinsed with cold physi-ological saline solution, dried thoroughly, and micro scintillation 0 (Perkin-Elmer) was added thereto. Then, the residual radioactivity on the filters was measured.

The uptake value when only solvent was added was set as 100%, the uptake value when unlabeled DA (final concentration 10 μM) was added as 0% (nonspecific uptake value), and the 50% inhibitory concentration was calculated from the concentration of the test compound and its inhibitory activity. The results are shown in Table 5.

TABLE 5

| Ex. | IC50 (nM) | Ex. | IC50 (nM) | Ex. | IC50 (nM) | Ex. | IC50 (nM) |
|---|---|---|---|---|---|---|---|
| 1 | 4.5 | 2 | 6.3 | 3 | 6.2 | 4 | 6.1 |
| 5 | 9.9 | 6 | 5.8 | 7 | 7.1 | 8 | 49.5 |
| 9 | 33.3 | 10 | 41.3 | 11 | 97.9 | 12 | 5.2 |
| 13 | 53.6 | 14 | 5.5 | 15 | 89.2 | 16 | 80.0 |
| 17 | 7.6 | 18 | 42.9 | 19 | 47.4 | 20 | 90.9 |
| 21 | 198.7 | 22 | 75.3 | 23 | 86.0 | 24 | 80.5 |
| 25 | 9.8 | 26 | 212.8 | 27 | 99.0 | 28 | 76.5 |
| 29 | 33.6 | 30 | 9.4 | 31 | 56.4 | 32 | 60.7 |
| 33 | 49.7 | 34 | 73.2 | 35 | 59.7 | 36 | 25.6 |
| 37 | 81.9 | 38 | 52.1 | 39 | 183.3 | 40 | 70.8 |
| 41 | 72.1 | 42 | 95.3 | 43 | 76.0 | 44 | 37.5 |
| 45 | 78.8 | 46 | 9.6 | 47 | 9.4 | 48 | 68.6 |
| 49 | 30.2 | 50 | 214.0 | 51 | 41.1 | 52 | 74.4 |
| 53 | 9.4 | 54 | 6.0 | 55 | 52.7 | 56 | 87.1 |
| 57 | 88.0 | 58 | 58.4 | 59 | 88.1 | 60 | 84.9 |
| 61 | 60.2 | 62 | 272.7 | 63 | 85.1 | 64 | 78.9 |
| 65 | 53.0 | 66 | 53.9 | 67 | 87.7 | 68 | 75.9 |
| 69 | 91.4 | 70 | 44.5 | 71 | 81.4 | 72 | 240.8 |
| 73 | 68.7 | 74 | 124.3 | 75 | 35.3 | 76 | 60.5 |
| 77 | 205.0 | 78 | 63.6 | 79 | 223.8 | 80 | 90.0 |

Test Example 4 (Metabolic Stability Test)

A metabolic reaction was initiated by adding and mixing a test compound solution (final concentration 0.001 mmol/L) and a NADH/NADPH solution (final concentration 1 mmol/L) to a human liver microsome solution (final concentration 100 mmol/L potassium phosphate buffer solution (pH 7.4), 5 mmol/L magnesium chloride, 0.2 mg/ml, human liver microsome). A solution of the internal standard in methanol was prepared and used as a quenching solution.

Specifically, a metabolic reaction was initiated by adding and mixing 2.5 μL of a solution of a test compound in acetonitrile to 222.5 μL of a human liver microsome solution in ice water, followed by preincubation at 37° C. for 1 minute, and then adding 25 μL of a NADH/NADPH solution thereto. After incubation at 37° C. for 0, 10 and 20 minutes, 25 μL of the reaction mixture was taken for each reaction time, and then it was added and mixed to 500 μL of a quenching solution to quench the reaction.

The mixture was centrifuged (6130 g, 4° C., 10 minutes) and the supernatant was used as a sample for LC-MS/MS.

Peak area ratio ([peak area of test compound]/[peak area of internal standard]) was calculated for the test compound and the internal standard.

The residual ratio of the test compound was calculated from ([Ratio of peak areas at each reaction time]/[Ratio of peak areas at 0 minute reaction time]).

Non-linear least-squares analysis was performed for the residual ratio and the incubation time to determine the disappearance rate constant ([0.693]/[Half-life]), and then the hepatic intrinsic clearance (μL/min/mg) was calculated from ([Disappearance rate constant]/[Microsomal concentration]). The results are shown in Table 6.

TABLE 6

| Ex. | μL/min/ mg | Ex. | μL/min/ mg | Ex. | μL/min/ mg | Ex. | μL/min/ mg |
|---|---|---|---|---|---|---|---|
| 1 | <50 | 2 | <50 | 3 | <50 | 4 | <50 |
| 5 | <50 | 6 | <50 | 7 | <50 | 8 | <50 |
| 9 | <50 | 10 | <50 | 11 | <50 | 12 | <50 |
| 13 | <50 | 14 | <50 | 15 | <50 | 16 | <50 |
| 17 | <50 | 18 | <50 | 19 | <50 | 20 | <50 |
| 21 | <50 | 22 | <50 | 23 | <50 | 24 | <50 |
| 25 | <50 | 26 | <50 | 27 | <50 | 28 | <50 |
| 29 | <50 | 30 | <50 | 31 | <50 | 32 | <50 |
| 33 | 55.3 | 34 | <50 | 35 | <50 | 36 | <50 |
| 37 | <50 | 38 | <50 | 39 | <50 | 40 | <50 |
| 41 | <50 | 42 | <50 | 43 | <50 | 44 | <50 |
| 45 | <50 | 46 | <50 | 47 | <50 | 48 | <50 |
| 49 | 52.0 | 50 | <50 | 51 | <50 | 52 | <50 |
| 53 | <50 | 54 | 68.0 | 55 | 86.0 | 56 | <50 |
| 57 | 58.0 | 58 | <50 | 59 | <50 | 60 | <50 |
| 61 | <50 | 62 | <50 | 63 | 84.0 | 64 | <50 |
| 65 | 81.0 | 66 | 58.0 | 67 | <50 | 68 | <50 |
| 69 | <50 | 70 | <50 | 71 | <50 | 72 | <50 |
| 73 | <50 | 74 | <50 | 75 | <50 | 76 | <50 |
| 77 | <50 | 78 | <50 | 79 | <50 | 80 | 57 |

Test Example 5 (CYP Inhibition Test (1): Inhibition Rate (%) in Evaluation of Con-Centratin)

A metabolic reaction was initiated by adding and mixing a test compound solution (final concentration 0.01 mmol/L) and a NADH/NADPH solution (final concentration 1 mmol/L) to a human liver microsome solution containing three CYP-specific substrates (final concentration 100 mmol/L potassium phosphate buffer solution (pH 7.4), 5 mmol/L magnesium chloride, 0.1 mg/mL human liver microsome, 0.005 mmol/L diclofenac (for CYP2C9), 0.01 mmol/L bufuralol (for CYP21D6), 0.005 mmol/L midazolam (for CYP3A4)). As an internal standard solution, a solution of each of stable isotopes of the metabolites (50 ng/mL [13C6] hydroxy diclofenac, 5 ng/mL [2H9] hydroxy bufuralol, and 5 ng/mL [13C6] hydroxy midazolam (all stable isotopes)) in methanol was prepared and used as a quenching solution.

Specifically, a metabolic reaction was initiated by adding and mixing 2 μL of a solution of a test compound in acetonitrile (or acetonitrile as a control) to 178 μL of a human liver microsome solution in ice water, followed by preincubation at 37° C. for 1 minute, and then adding 20 μL of a NADH/NADPH solution thereto. After incubation at 37° C. for 10 minutes, 50 μL of the reaction mixture was taken, and then it was added and mixed to 500 μL of a quenching solution to quech the reaction.

The mixture was centrifuged (6130 g, 4° C., 10 minutes) and the supernatant was used as a sample for LC-MS/MS.

Peak area ratio ([peak area of metabolite]/[peak area of corresponding stable isotope]) was calculated for a metabolite and a stable isotope of the metabolite as measurement object. By comparing the peak area ratio of each test compound solution with that of the control, the inhibition rate (%) of each CYP species for each test compound was calculated from (1-[peak area ratio of each test compound solution]/[peak area ratio of control])×100. The results are shown in Table 7.

TABLE 7

| (%) | | | | | | | |
|---|---|---|---|---|---|---|---|
| Ex. | 2C9 | 2D6 | 3A4 | Ex | 2C9 | 2D6 | 3A4 |
| 1 | −6.1 | 18.1 | 7.4 | 53 | 3.0 | 42.7 | −13.7 |
| 2 | −8.7 | 10.5 | 16.7 | 54 | 7.1 | 19.8 | 13.5 |
| 3 | −10.5 | 12.9 | 21.2 | 55 | 11.2 | 28.0 | 13.3 |
| 4 | −9.1 | 15.0 | 7.1 | 56 | 11.3 | 18.0 | 11.2 |
| 5 | −3.9 | 17.0 | −0.8 | 57 | 9.3 | 14.9 | 8.6 |
| 6 | −6.4 | 15.0 | 23.3 | 58 | 2.8 | 16.1 | 13.1 |
| 7 | 1.3 | 17.5 | 37.9 | 59 | 5.6 | 14.0 | −0.2 |
| 8 | 8.1 | 20.1 | 7.1 | 60 | −0.5 | 18.1 | 3.5 |
| 9 | 5.7 | 17.7 | 6.3 | 61 | 6.8 | 16.1 | −2.7 |
| 10 | 4.3 | 9.1 | 16.2 | 62 | 4.6 | 17.8 | −1.6 |
| 11 | 7.5 | 14.2 | −1.3 | 63 | 1.1 | 19.2 | 6.1 |
| 12 | 8.6 | 16.5 | 48.8 | 64 | 10.2 | 21.6 | 3.9 |
| 13 | 14.1 | 23.1 | 34.0 | 65 | 12.1 | 30.5 | 15.0 |
| 14 | 13.6 | 20.5 | 14.4 | 66 | 13.3 | 25.1 | 14.8 |
| 19 | 5.8 | 5.9 | 16.1 | 67 | 15.5 | 20.7 | −2.2 |
| 39 | 1.3 | 3.2 | 3.7 | 68 | 14.2 | 24.6 | 1.8 |
| 40 | −13.8 | 15.7 | −15.2 | 69 | 14.8 | 45.6 | 19.7 |
| 41 | −11.0 | 25.3 | −11.0 | 70 | 15.8 | 28.4 | 17.6 |
| 42 | −9.3 | 9.8 | −4.7 | 71 | 0.6 | 28.8 | −3.4 |
| 43 | −10.8 | 7.8 | −13.7 | 72 | 1.7 | 17.9 | −2.4 |
| 44 | −11.4 | 10.2 | −10.7 | 73 | 4.8 | 21.5 | 5.9 |
| 45 | −5.2 | 23.2 | −2.6 | 74 | 0.7 | 17.8 | −10.8 |
| 46 | −3.8 | 9.5 | −7.4 | 75 | 9.1 | 19.3 | 9.9 |
| 47 | −9.7 | 12.2 | −14.3 | 76 | 12.6 | 21.9 | 12.4 |
| 48 | −0.7 | −7.8 | −9.2 | 77 | 7.9 | 18.1 | −1.9 |
| 49 | −1.1 | 28.3 | 3.8 | 78 | 5.8 | 46.0 | 15.1 |
| 50 | −7.6 | 41.8 | 2.0 | 79 | 8.9 | 38.8 | 17.1 |
| 51 | −8.3 | 17.0 | 1.1 | 80 | 2.0 | 20.9 | 17.6 |
| 52 | 9.2 | 23.0 | 0.1 | | | | |

Test Example 6 (CYP Inhibition Test (2): 50% Inhibitory Concentration W Calculated from the Evaluation Results of 3 Concentrations)

A metabolic reaction was initiated by adding and mixing a test compound solution (final concentration 0.01, 0.03 and 0.1 mmol/L) and a NADH/NADPH solution (final concentration 1 mmol/L) to a human liver microsome solution containing three CYP-specific substrates (final concentration 100 mmol/L potassium phosphate buffer solution (pH 7.4), 5 mmol/L magnesium chloride, 0.1 mg/mL human liver microsome, 0.005 mmol/L diclofenac (for CYP2C9), 0.01 mmol/L bufuralol (for CYP2D6), 0.005 mmol/L midazolam (for CYP3A4)). As an internal standard solution, a solution of each of stable isotopes of the metabolites (50 ng/mL [13C6] hydroxy diclofenac, 5 ng/mL [2H9] hydroxy bufuralol, and 5 ng/mL [13C6] hydroxy midazolam (all stable isotopes)) in methanol was prepared and used as a quenching solution.

Specifically, a metabolic reaction was initiated by adding and mixing 2 μL of a solution of a test compound in acetonitrile (or acetonitrile as a control) to 178 μL of a human liver microsome solution in ice water, followed by preincubation at 37° C. for 1 minute, and then adding 20 μL of a NADH/NADPH solution thereto. After incubation at 37° C. for 10 minutes, 50 μL of the reaction mixture was taken, and then it was added and mixed to 500 μL of a quenching solution to quech the reaction.

The mixture was centrifuged (6130 g, 4° C., 10 minutes) and the supernatant was used as a sample for LC-MS/MS.

Peak area ratio ([peak area of metabolite]/[peak area of corresponding stable isotope]) was calculated for a metabolite and a stable isotope of the metabolite as measurement object. By comparing the peak area ratio of each test compound solution with that of the control, the inhibition rate (%) of each CYP species for each test compound was calculated from (1−[peak area ratio of each test compound solution]/[peak area ratio of control])×100.

The slope and intercept of a linear regression of the logarithm of the final concentration (0.01, 0.03 and 0.1 mmol/L) of the test compound for each CYP species against the inhibition rate (%) at each concentration were calculated. Then, the concentration at which the inhibition rate (%) for each CYP species reached 50% was calculated, and it was defined as 50% inhibitory concentration. The results are shown in Table 8.

TABLE 8

| Ex. | 2C9 | 2D6 | 3A4 (μM) |
|---|---|---|---|
| 15 | >100 | >100 | >100 |
| 16 | >100 | >100 | >100 |
| 17 | >100 | >100 | >100 |
| 18 | >100 | 59.1 | >100 |
| 20 | >100 | >100 | 94.9 |
| 21 | >100 | >100 | >100 |
| 22 | >100 | >100 | >100 |
| 23 | >100 | >100 | >100 |
| 24 | >100 | 62.5 | 96.1 |
| 25 | >100 | >100 | 70.6 |
| 26 | >100 | >100 | >100 |
| 27 | >100 | >100 | >100 |
| 28 | >100 | >100 | >100 |
| 29 | 100.0 | 99.4 | >100 |
| 30 | >100 | >100 | 78.6 |
| 31 | >100 | >100 | 62.5 |
| 32 | >100 | >100 | 62.8 |
| 33 | >100 | 57.4 | 53.5 |
| 34 | >100 | >100 | >100 |
| 35 | >100 | 55.5 | >100 |
| 36 | 100.0 | 87.6 | >100 |
| 37 | >100 | >100 | 86.7 |
| 38 | >100 | >100 | >100 |

Test Example 7 (Protein Binding Rate Test)

A serum sample was prepared by adding a test compound solution to a human serum (final concentration of the test compound: 0.001 mmol/L). The serum sample and Dulbecco's Phosphate-Buffered Saline (D-PBS(−)) were added to the wells separated by a dialysis membrane to start the reaction. A solution of the internal standard in methanol was prepared and used as a quenching solution.

Specifically, the dialysis membrane (cut-off molecular weight 12000-14000) was pre-conditioned by immersing it in distilled water, followed by 20% ethanol. Then, the membrane was washed with D-PBS(−) and set in an equilibrium dialysis kit. Then, 150 μL of D-PBS(−) was added to one part of each well divided by the dialysis membrane, and 150 μL of serum sample was added to the other part. After sealing all wells and incubation at 37° C. for 6 hours, 30 μL from the serum side and 90 μL from the PBS side of each well were collected and mixed with 90 μL of D-PBS(−) or 30 μL of blank serum and 480 μL of a quenching solution to quench the reaction.

The mixture was centrifuged (6130 g, 4° C., 10 minutes) and the supernatant was used as a sample for LC-MS/MS.

Peak area ratio ([peak area of test compound]/[peak area of internal standard]) was calculated for the test compound and the internal standard. By comparing the peak area ratio of the PBS side for each test compound with that of the serum side, the protein binding rate (%) of each test compound was calculated from (1-[peak area ratio of PBS side]/[peak area ratio of serum side])×100. The results are shown in Table 9.

TABLE 9

| Ex. | % | Ex. | % | Ex. | % | Ex. | % |
|---|---|---|---|---|---|---|---|
| 1 | 41.5 | 2 | 55.6 | 3 | 67.2 | 4 | 71.3 |
| 5 | 43.0 | 6 | 59.9 | 7 | 66.7 | 8 | 31.4 |
| 9 | 54.5 | 10 | 54.9 | 11 | 23.3 | 12 | 79.6 |
| 13 | 60.3 | 14 | 38.5 | 15 | 18.3 | 16 | 24.9 |
| 17 | 27.3 | 18 | 25.9 | 19 | 52.9 | 20 | 43.1 |
| 21 | 41.5 | 22 | 49.5 | 23 | 45.4 | 24 | 58.8 |
| 25 | 66.5 | 26 | 42.0 | 27 | 41.5 | 28 | 38.4 |
| 29 | 39.8 | 30 | 41.7 | 31 | 50.3 | 32 | 51.8 |
| 33 | 71.4 | 34 | 20.4 | 35 | 22.4 | 36 | 36.2 |
| 37 | 47.1 | 38 | 45.3 | 39 | 35.7 | 40 | 36.5 |
| 41 | 31.5 | 42 | 58.2 | 43 | 45.6 | 44 | 43.4 |
| 45 | 64.8 | 46 | 61.4 | 47 | 63.4 | 48 | 58.7 |
| 49 | 76.9 | 50 | 44.9 | 51 | 44.7 | 52 | 27.0 |
| 53 | 43.8 | 54 | 69.3 | 55 | 73.8 | 56 | 61.8 |
| 57 | 70.6 | 58 | 64.2 | 59 | 50.2 | 60 | 65.8 |
| 61 | 66.3 | 62 | 59.6 | 63 | 73.9 | 64 | 50.1 |
| 65 | 79.6 | 66 | 77.1 | 67 | 31.5 | 68 | 31.8 |
| 69 | 78.9 | 70 | 80.5 | 71 | 71.5 | 72 | 23.4 |
| 73 | 73.3 | 74 | 28.0 | 75 | 72.3 | 76 | 69.2 |
| 77 | 58.9 | 78 | 67.7 | 79 | 71.1 | 80 | 79.0 |

Industrial Availability

The compound of the present invention or a salt thereof has a broad therapeutic spectrum.

The invention claimed is:

1. A compound represented by formula [I]:

[I]

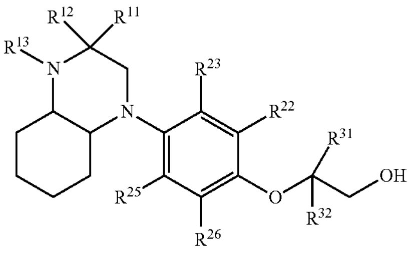

wherein $R^{11}$, $R^{12}$ and $R^{13}$ are the same or different and each independently represents hydrogen or $C_{1-6}$ alkyl, or $R^{11}$ and $R^{12}$ together with the adjacent carbon atom form a 3- to 8-membered cycloalkane;

$R^{22}$, $R^{23}$, $R^{25}$ and $R^{26}$ are the same or different and each independently represents hydrogen, halogen, $C_{1-6}$ alkyl or $C_{1-6}$ alkoxy, or $R^{22}$ and $R^{23}$ form a 9- to 10-membered bicyclic ring system containing oxygen atom as ring-constituting atom together with a benzene ring adjacent to them;

$R^{31}$ and $R^{32}$ are the same or different and each independently represents hydrogen or halogen, or a salt thereof.

2. The compound according to claim 1, wherein the formula [I] is selected from the following formula [Ia], formula [Ib], formula [Ic] or formula [Id]:

[Ia]

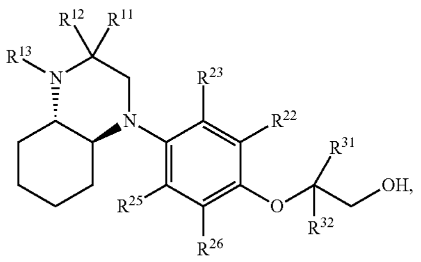

[Ib]

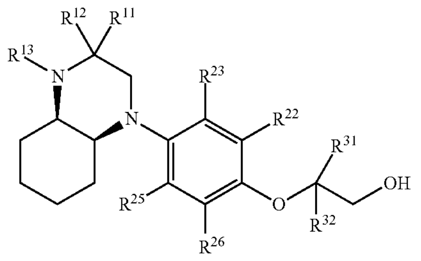

[Ic]

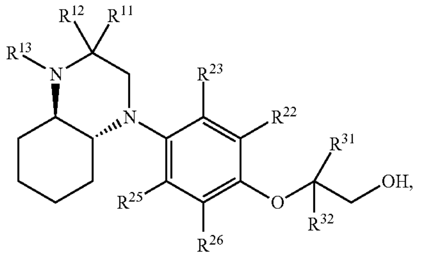

[Id]

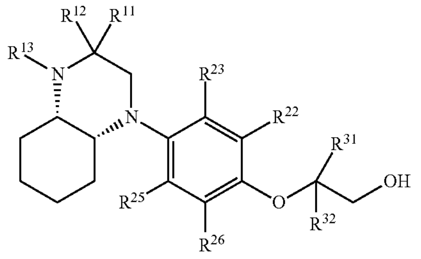

wherein each symbol is as defined above, or a salt thereof.

3. The compound according to claim 1, wherein in the formula [I], $R^{11}$, $R^{12}$ and $R^{13}$ are the same or different and each independently represents hydrogen or methyl, or $R^{11}$ and $R^{12}$ together with the adjacent carbon atom form cyclobutyl;

$R^{22}$, $R^{23}$, $R^{25}$ and $R^{26}$ are the same or different and each independently represents hydrogen, fluorine, chlorine, methyl or methoxy, or $R^{22}$ and $R^{23}$ together with the adjacent benzene ring form a benzofuran; and $R^{31}$ and $R^{32}$ are the same or different and each independently represents hydrogen or fluorine;

or a salt thereof.

4. The compound according to claim 1, wherein in the formula [I], two or more of $R^{22}$, $R^{23}$, $R^{25}$ and $R^{26}$ are hydrogen, or a salt thereof.

5. The compound according to claim 1, which is selected from the group consisting of the following compounds:

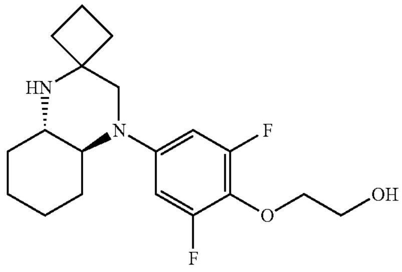
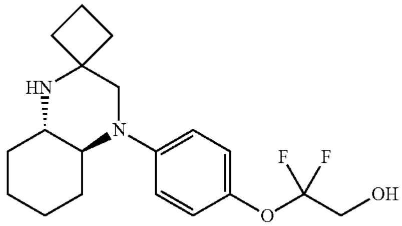
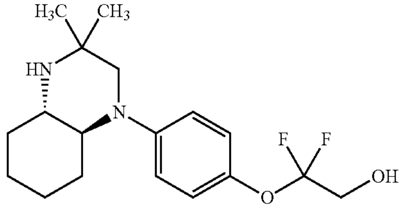
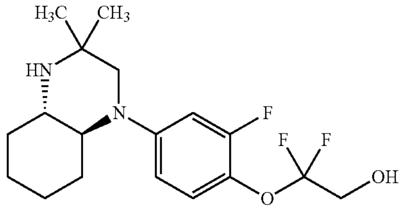
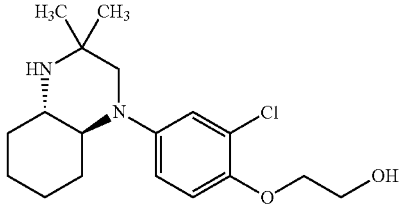
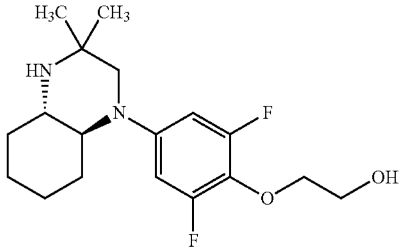
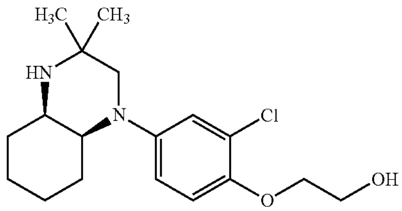
-continued
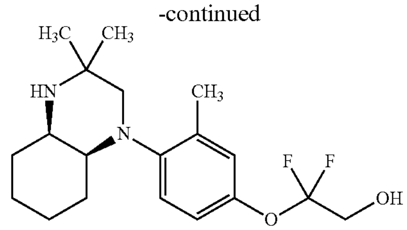
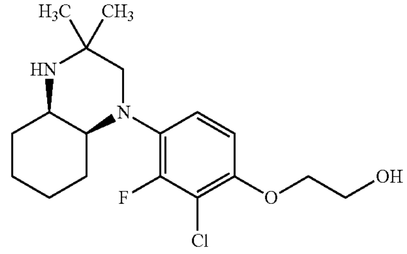
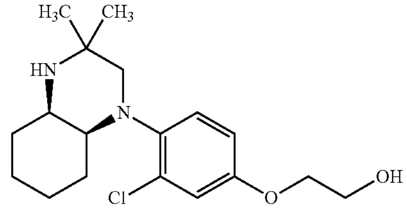
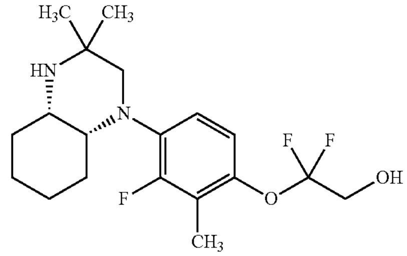
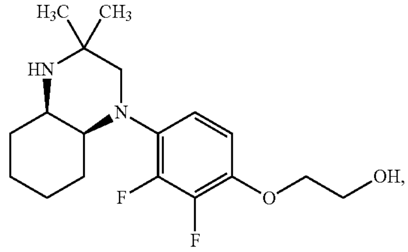
,
or a salt thereof.
6. A pharmaceutical composition comprising the compound according to claim 1 or a salt thereof as active ingredient, and a pharmaceutically acceptable carrier.
7. The compound according to claim 5, wherein the compound is:
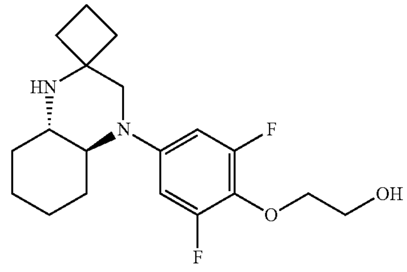 [SMILES: OCCOc1c(F)cc(N2CC3(CCC3)N[C@H]3CCCC[C@@H]32)cc1F]
or a salt thereof.

8. The compound according to claim 5, wherein the compound is:

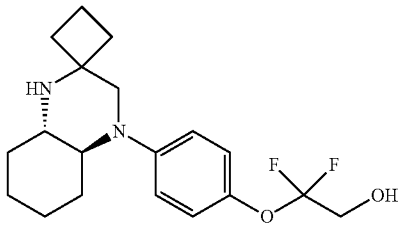 [SMILES: OCC(F)(F)Oc1ccc(N2CC3(CCC3)N[C@H]3CCCC[C@@H]32)cc1]

or a salt thereof.

9. The compound according to claim 5, wherein the compound is:

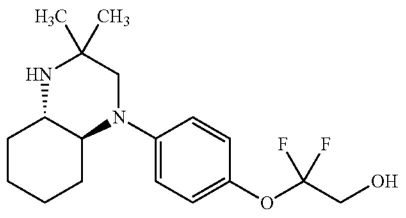 [SMILES: CC1(C)CN(c2ccc(OC(F)(F)CO)cc2)[C@H]2CCCC[C@@H]2N1]

or a salt thereof.

10. The compound according to claim 5, wherein the compound is:

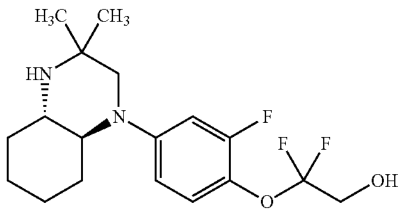 [SMILES: CC1(C)CN(c2ccc(OC(F)(F)CO)c(F)c2)[C@H]2CCCC[C@@H]2N1]

or a salt thereof.

11. The compound according to claim 5, wherein the compound is:

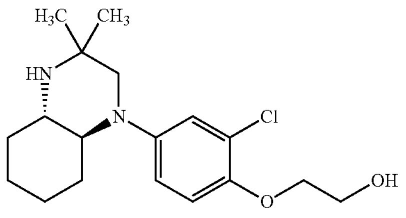 [SMILES: CC1(C)CN(c2ccc(OCCO)c(Cl)c2)[C@H]2CCCC[C@@H]2N1]

or a salt thereof.

12. The compound according to claim 5, wherein the compound is:

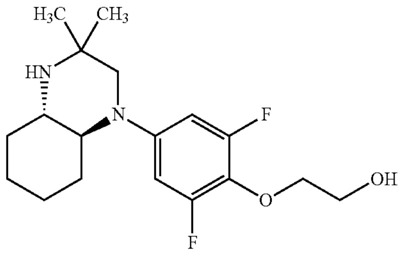 [SMILES: CC1(C)CN(c2cc(F)c(OCCO)c(F)c2)[C@H]2CCCC[C@@H]2N1]

or a salt thereof.

13. The compound according to claim 5, wherein the compound is:

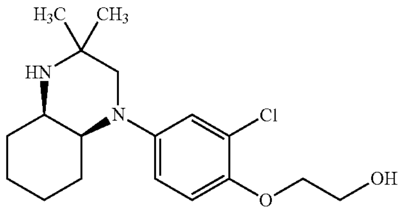 [SMILES: CC1(C)CN(c2ccc(OCCO)c(Cl)c2)[C@H]2CCCC[C@H]2N1]

or a salt thereof.

14. The compound according to claim 5, wherein the compound is:

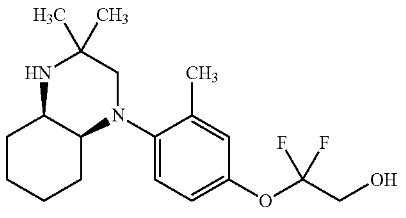 [SMILES: Cc1cc(OC(F)(F)CO)ccc1N1CC(C)(C)N[C@@H]2CCCC[C@@H]21]

or a salt thereof.

15. The compound according to claim 5, wherein the compound is:

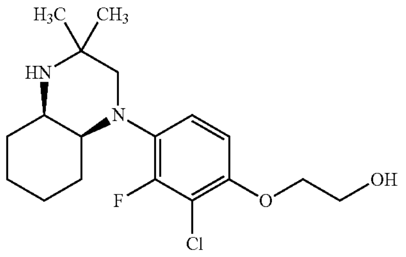 [SMILES: CC1(C)CN(c2ccc(OCCO)c(Cl)c2F)[C@H]2CCCC[C@H]2N1]

or a salt thereof.

16. The compound according to claim 5, wherein the compound is:

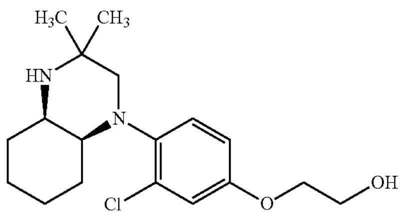 [SMILES: CC1(C)CN(c2ccc(OCCO)cc2Cl)[C@H]2CCCC[C@H]2N1]

or a salt thereof.

17. The compound according to claim 5, wherein the compound is:

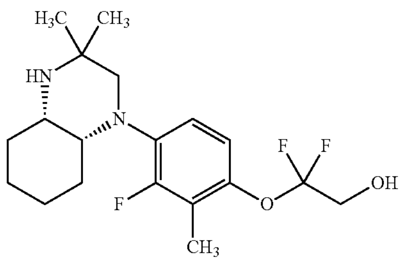 [SMILES: Cc1c(OC(F)(F)CO)ccc(N2CC(C)(C)N[C@H]3CCCC[C@H]32)c1F]

or a salt thereof.

18. The compound according to claim 5, wherein the compound is:

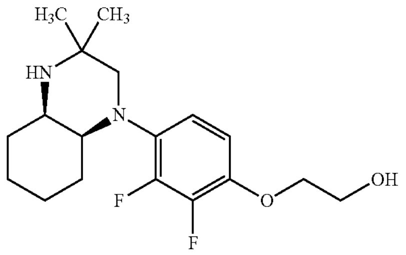 [SMILES: CC1(C)CN(c2ccc(OCCO)c(F)c2F)[C@H]2CCCC[C@H]2N1]

or a salt thereof.

19. The compound according to claim 5, wherein the compound is:

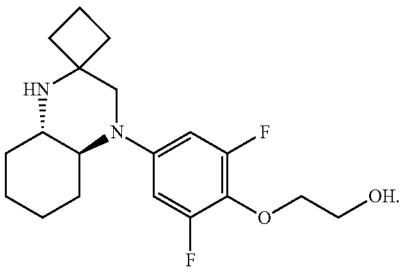 [SMILES: OCCOc1c(F)cc(N2CC3(CCC3)N[C@H]3CCCC[C@@H]32)cc1F]

20. The compound according to claim 5, wherein the compound is:

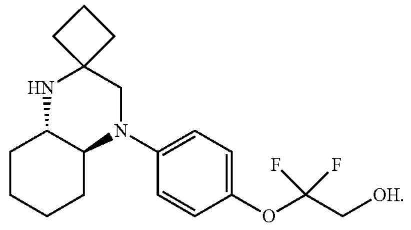 [SMILES: OCC(F)(F)Oc1ccc(N2CC3(CCC3)N[C@H]3CCCC[C@@H]32)cc1]

21. The compound according to claim 5, wherein the compound is:

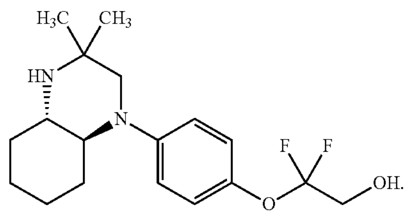 [SMILES: CC1(C)CN(c2ccc(OC(F)(F)CO)cc2)[C@H]2CCCC[C@@H]2N1]

22. The compound according to claim 5, wherein the compound is:

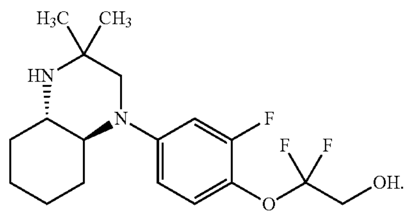 [SMILES: CC1(C)CN(c2ccc(OC(F)(F)CO)c(F)c2)[C@H]2CCCC[C@@H]2N1]

23. The compound according to claim 5, wherein the compound is:

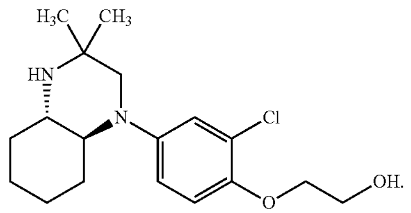 [SMILES: CC1(C)CN(c2ccc(OCCO)c(Cl)c2)[C@H]2CCCC[C@@H]2N1]

24. The compound according to claim 5, wherein the compound is:

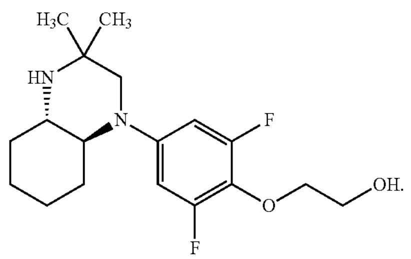 [SMILES: CC1(C)CN(c2cc(F)c(OCCO)c(F)c2)[C@H]2CCCC[C@@H]2N1]

25. A salt of the compound according to claim 5, wherein the compound is:

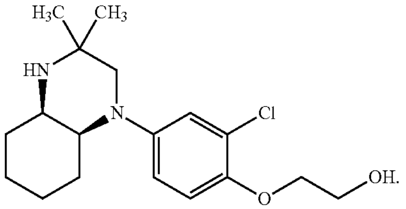 [SMILES: CC1(C)CN(c2ccc(OCCO)c(Cl)c2)[C@H]2CCCC[C@H]2N1]

26. A hemi fumarate salt of the compound according to claim 5, wherein the compound is:

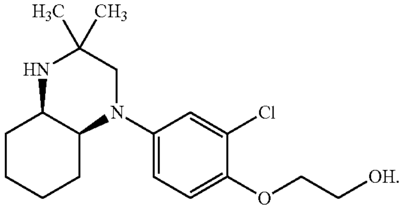 [SMILES: CC1(C)CN(c2ccc(OCCO)c(Cl)c2)[C@H]2CCCC[C@H]2N1]

27. The compound according to claim 5, wherein the compound is:

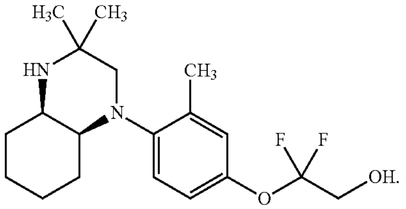 [SMILES: Cc1cc(OC(F)(F)CO)ccc1N1CC(C)(C)N[C@@H]2CCCC[C@@H]21]

28. A salt of the compound according to claim 5, wherein the compound is:

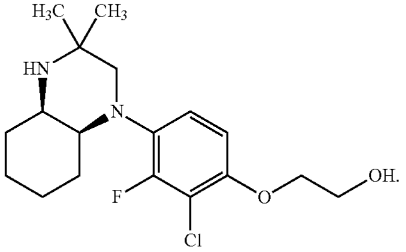 [SMILES: CC1(C)CN(c2ccc(OCCO)c(Cl)c2F)[C@H]2CCCC[C@H]2N1]

29. A fumarate salt of the compound according to claim 5, wherein the compound is:

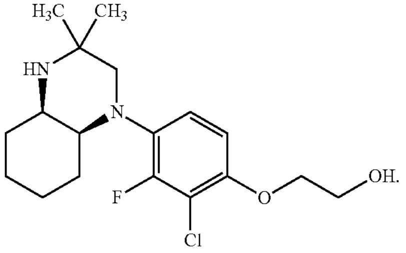

30. A salt of the compound according to claim 5, wherein the compound is:

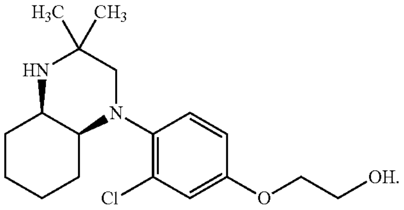 [SMILES: CC1(C)CN(c2ccc(OCCO)cc2Cl)[C@H]2CCCC[C@H]2N1]

31. A hemi fumarate salt of the compound according to claim 5, wherein the compound is:

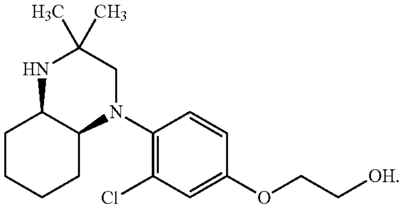 [SMILES: CC1(C)CN(c2ccc(OCCO)cc2Cl)[C@H]2CCCC[C@H]2N1]

32. A salt of the compound according to claim 5, wherein the compound is:

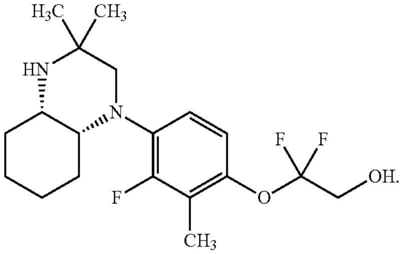

33. A hemi fumarate salt of the compound according to claim 5, wherein the compound is:

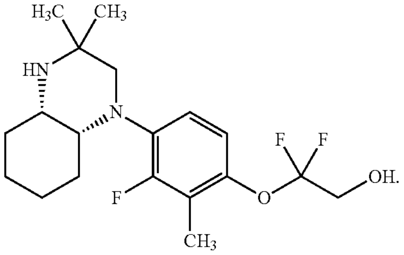 [SMILES: Cc1c(OC(F)(F)CO)ccc(N2CC(C)(C)N[C@H]3CCCC[C@H]32)c1F]

34. A salt of the compound according to claim 5, wherein the compound is:
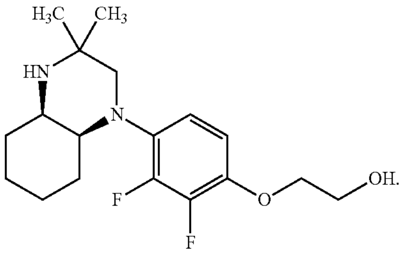 [SMILES: CC1(C)CN(c2ccc(OCCO)c(F)c2F)[C@H]2CCCC[C@H]2N1]
35. A hemi fumarate salt of the compound according to claim 5, wherein the compound is:
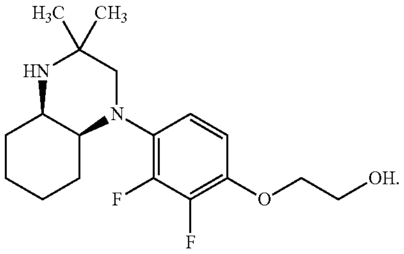 [SMILES: CC1(C)CN(c2ccc(OCCO)c(F)c2F)[C@H]2CCCC[C@H]2N1]
* * * * *